United States Patent
Kreymann et al.

(10) Patent No.: US 11,583,620 B2
(45) Date of Patent: Feb. 21, 2023

(54) METHOD FOR EXTRACORPOREAL LUNG SUPPORT

(71) Applicant: Advitos GmbH, Munich (DE)

(72) Inventors: Bernhard Kreymann, Munich (DE); Christoph Hüßtege, Munich (DE)

(73) Assignee: Advitos GmbH, Munich (DE)

( * ) Notice: Subject to any disclaimer, the term of this patent is extended or adjusted under 35 U.S.C. 154(b) by 1196 days.

(21) Appl. No.: 15/777,639

(22) PCT Filed: Nov. 18, 2016

(86) PCT No.: PCT/EP2016/078198
§ 371 (c)(1),
(2) Date: May 18, 2018

(87) PCT Pub. No.: WO2017/085292
PCT Pub. Date: May 26, 2017

(65) Prior Publication Data
US 2019/0030232 A1    Jan. 31, 2019

(30) Foreign Application Priority Data
Nov. 20, 2015   (EP) .................. PCT/EP2015/002331

(51) Int. Cl.
| | |
|---|---|
| *A61M 1/16* | (2006.01) |
| *A61M 1/36* | (2006.01) |
| *A61M 1/32* | (2006.01) |

(52) U.S. Cl.
CPC ........ *A61M 1/1698* (2013.01); *A61M 1/1676* (2014.02); *A61M 1/1696* (2013.01);
(Continued)

(58) Field of Classification Search
CPC .............. A61M 1/1698; A61M 1/1676; A61M 1/1696; A61M 1/31; A61M 1/3666;
(Continued)

(56) References Cited

U.S. PATENT DOCUMENTS 3,846,236 A * 11/1974 Updike ............... A61M 1/1629
435/2
3,953,329 A * 4/1976 Updike ............... A61M 1/1698
210/638

(Continued)

FOREIGN PATENT DOCUMENTS

| CN | 1120439 A | 4/1996 |
|---|---|---|
| CN | 101883594 A | 11/2010 |

(Continued)

OTHER PUBLICATIONS

International Search Report issued for International Application No. PCT/EP2016/078198 dated Sep. 1, 2017.

(Continued)

*Primary Examiner* — Andrew J Mensh
(74) *Attorney, Agent, or Firm* — Medler Ferro Woodhouse & Mills

(57) ABSTRACT

The present invention generally relates to a process suitable for extracorporeal lung support. The process comprises contacting blood with a dialysis liquid separated by a semipermeable membrane. Oxygen is introduced into blood and/or into the dialysis liquid prior to contacting blood and dialysis liquid being separated by the semipermeable membrane. The process is versatile and allows for blood oxygenation as well as removal of at least one undesired substance occurring in the blood, selected from carbon dioxide, bicarbonate and hydrogen cations, from blood. Thereby, the present invention takes advantage of the Haldane effect in the extracorporeal contacting step. The undesired substance can be efficiently transported across a semipermeable membrane to the dialysis liquid. In contrast to extracorporeal carbon dioxide removal methods of the prior art (ECCCbR), the present invention employs a versatile dialysis liquid that allows to adjust the pH and buffering capacity of the dialysis liquid, to add fluids to the (Continued)

dialysis liquid and/or to the blood and to remove substances from the blood in the extracorporeal circuit, depending on the conditions and needs. The present invention also provides regeneration and recycling of the dialysis liquid, and thus for its repeated use. The present invention is suitable for treating human or animal subjects suffering from lung failure or lung disorders.

29 Claims, 7 Drawing Sheets

(52) U.S. Cl.
 CPC .............. *A61M 1/32* (2013.01); *A61M 1/369* (2013.01); *A61M 1/3666* (2013.01); *A61M 2202/0208* (2013.01); *A61M 2202/0225* (2013.01); *A61M 2202/03* (2013.01); *A61M 2202/0476* (2013.01); *A61M 2202/06* (2013.01); *A61M 2230/202* (2013.01); *A61M 2230/205* (2013.01); *A61M 2230/208* (2013.01)

(58) Field of Classification Search
 CPC .......... A61M 1/369; A61M 2202/0208; A61M 2202/0225; A61M 2202/03; A61M 2202/0476; A61M 2202/06; A61M 2230/202; A61M 2230/205; A61M 2230/208
 USPC ........................................................ 604/6.14
 See application file for complete search history.

(56) References Cited

U.S. PATENT DOCUMENTS

| | | | |
|---|---|---|---|
| 4,375,414 A | 3/1983 | Strahilevitz | |
| 4,663,049 A | 5/1987 | Kolff et al. | |
| 4,769,132 A | 9/1988 | Patono | |
| 5,561,115 A | 10/1996 | Tenold | |
| 5,744,042 A | 4/1998 | Stange et al. | |
| 6,264,680 B1 | 7/2001 | Ash | |
| 6,569,112 B2 | 5/2003 | Strahilevitz | |
| 6,602,502 B1 | 8/2003 | Strahilevitz | |
| 6,821,431 B2 | 11/2004 | Collins et al. | |
| 7,112,273 B2 | 9/2006 | Weigel et al. | |
| 7,435,342 B2 | 10/2008 | Tsukamoto | |
| 7,455,771 B2 | 11/2008 | Kreymann | |
| 7,670,491 B2 | 3/2010 | Callan et al. | |
| 8,377,308 B2 | 2/2013 | Kreymann et al. | |
| 8,480,899 B2 | 7/2013 | Kreymann | |
| 8,574,438 B2 | 11/2013 | Kreymann et al. | |
| 9,039,896 B2 | 5/2015 | Kreymann | |
| 9,248,112 B2 | 2/2016 | Moddel et al. | |
| 10,245,364 B2 | 4/2019 | Brandl et al. | |
| 2002/0019603 A1 | 2/2002 | Strahilevitz | |
| 2002/0158019 A1 | 10/2002 | Collins et al. | |
| 2002/0187940 A1 | 12/2002 | Masuda et al. | |
| 2003/0105424 A1 | 6/2003 | Karoor et al. | |
| 2005/0006296 A1 | 1/2005 | Sullivan et al. | |
| 2005/0082225 A1* | 4/2005 | Kreymann | A61M 1/1696 210/639 |
| 2009/0018484 A1* | 1/2009 | Levitov | A61M 1/1698 604/6.14 |
| 2010/0258503 A1 | 10/2010 | Kreymann et al. | |
| 2012/0080377 A1* | 4/2012 | Jensen | B01D 69/02 210/643 |
| 2012/0190103 A1* | 7/2012 | Maurer | B01D 63/026 435/283.1 |
| 2013/0087210 A1 | 4/2013 | Brandl et al. | |
| 2013/0118979 A1 | 5/2013 | Kreymann et al. | |
| 2015/0086969 A1* | 3/2015 | Evans | A61M 1/369 435/2 |
| 2015/0335807 A1 | 11/2015 | Kellum, Jr. et al. | |

FOREIGN PATENT DOCUMENTS

| | | |
|---|---|---|
| CN | 102138932 A | 8/2011 |
| CN | 102421431 A | 4/2012 |
| CN | 102940886 A | 2/2013 |
| CN | 104394902 A | 3/2015 |
| EP | 0615780 A1 | 9/1994 |
| EP | 0976759 A2 | 2/2000 |
| EP | 1649883 A1 | 4/2006 |
| EP | 1867354 A2 | 12/2007 |
| EP | 2019296 A1 | 1/2009 |
| EP | 2214752 A1 | 8/2010 |
| FR | 2651438 A1 | 3/1991 |
| GB | 1484642 A | 9/1977 |
| JP | 2000-038348 A | 2/2000 |
| JP | 2000-72658 A | 7/2000 |
| JP | 2011-505209 A | 2/2011 |
| JP | 2012-228285 A | 11/2012 |
| WO | 8400689 A1 | 3/1984 |
| WO | 9421363 A1 | 9/1994 |
| WO | 01/51185 A1 | 7/2001 |
| WO | 2002/049693 A2 | 6/2002 |
| WO | 2003/094998 A1 | 11/2003 |
| WO | 2004/066121 A2 | 8/2004 |
| WO | 2004/069311 A1 | 8/2004 |
| WO | 2005/035023 A1 | 4/2005 |
| WO | 2009/071103 A1 | 6/2009 |
| WO | 2013/144793 A1 | 10/2013 |
| WO | 2014/113740 A1 | 7/2014 |
| WO | 2014/160370 A1 | 10/2014 |
| WO | 2015/074973 A1 | 5/2015 |
| WO | 2017/084683 A1 | 5/2017 |
| WO | 2017/085291 A1 | 5/2017 |
| WO | 2018/215918 A1 | 11/2018 |

OTHER PUBLICATIONS

Japanese Office Action for JP App. No. JP2016538118A, dated Nov. 24, 2020.
A guide for the preparation and use of buffers in biological systems by Calbiochem, Date unknown.
Al-Chalabi, Ahmed et al., "Evaluation of the Hepa Wash Treatment in Pigs with Acute Liver Failure," BMC Gastroenterology, Biomed Central Ltd., London, GB, vol. 13, No. 1, May 13, 2013 (May 13, 2013), 10 pages.
Benjamin Struecker et al: "Liver support strategies: cutting-edge technologies", Nature Reviews / Gastroenterology & Hepatology, vol. 11, No. 3, Oct. 29, 2013 (Oct. 29, 2013), pp. 166-176, XP055323390, US ISSN: 1759-5045, DOI: 10.1038/nrgastro.2013. 204 the whole document figure 1.
Daugirdas, et al., Handbook of Dialysis, 4th Ed., pp. 59-79.
Fasano et al., "The Extraordinary Ligand Binding Properties of Human Serum Albumin", Life Dec. 2005; 57(12):787-796.
Huber et al., "First clinical experience in 14 patients treated with ADVOS: a study on feasibility, safety and efficacy of a new type of albumin dialysis", BMC Gastoenterology, vol. 17, No. 1, Feb. 16, 2017 (Feb. 16, 2017), pp. 1-11.
Jan Stange et al., Artificial Organs, 26 (2), International Society for Arlilicial Organs, "The Molecular Adsorbents Recycling System as a Liver Support System Based on Albumin Dialysis: A Summary of Preclinical Investigations, Prospective, Randomized, Controlled Clinical Trial, and Clinical Experience from 19 Centers" pp. 103-110, 2002.
J. G. O'Grady et al, Liver, Pancreas, and Biliary Tract, "Controlled Trials of Charcoal Hemoperfusion and Prognostic Factors in Fulminant Hepatic Failure", Gastroenterology 94: pp. 1186-1192, 1988.
Karla C. L. Lee et al: "Extracorporeal liver support devices for listed patients", Liver Transplantation, vol. 22, No. 6, May 26, 2016 (May 26, 2016), pp. 839-848, XP055323376, US ISSN: 1527-6465, DOI: 10.1002/lt.24396 the whole document.
Laleman et al., "Acute-on-chronic liver failure: current concepts on definition, pathogenesis, clinical manifestations and potential therapeutic interventions", Expert Review of Gastroenterology & Hepatology, vol. 5, No. 4, Aug. 2011 (Aug. 4, 2011), pp. 523-537.

(56) References Cited

OTHER PUBLICATIONS

Misra, "The Basics of Hemodialysis Equipment," Hemodialysis International 2005; 9: 30-36.
Nahas et al. (Guidelines for the Treatment of acidaemia with THAM, Drugs, pp. 191-224, Feb. 1998). (Year: 1998).
Nolte, Stephan H. et al., "Hemodialysis for Extracorporeal Bicarbonate/ $CO_2$ Removal (ECBicCO2R) and Apneic Oxygenation for Respiratory Failure in the Newborn," Asaio Transactions, vol. 35, No. 1, Jan. 1, 1989 (Jan. 1, 1989), 5 pages.
Peters, T. "All About Albumin: Biochemistry, Genetics, and Medical Applications," Dec. 8, 1995; New York: Academic Press, Chapter 3.
Polaschegg, et al., "Hemodialysis machines and monitors, in: Replacement of Renal Function by Dialysis", 5th Ed., eds. Hol, Koch, Lindsay, Ronco, Winchester, pp. 325-449.
Russ, Martin et al., "Experimental High-Volume Hemofiltration With Predilutional Tris-Hydroxymethylaminomethane for Correction of Low Tidal Volume Ventilation-Induced Acidosis," Artificial Organs, vol. 35, No. 6, May 30, 2011 (May 30, 2011), 11 pages.
Schwarzbeck, et al., Clin Nephrol, 1977 7(3): 125-7.
Sponholz et al., "Molecular adsorbent recirculating system and single-pass albumin dialysis in liver failure—a prospective, randomised crossover studfy", Critical Care (London, England), vol. 20, Jan. 4, 2016 (Jan. 4, 2016), pp. 1-13.
Table of Acids with Kas and pKas (1 page). (Year: 2002).
Vanholder et al., "A Bench to Bedside View of Uremic Toxins," A Soc Nephrol May 2008: 19: 863-87.
Worthley (Hydrogen Ion Metabolism, Anaeth. Intens. Care, 1977 5, pp. 347-360). (Year: 1977).

\* cited by examiner

METHOD FOR EXTRACORPOREAL LUNG SUPPORT

CROSS REFERENCE TO RELATED APPLICATIONS

This application is a U.S. National Phase application under 35 USC § 371 of International Application No. PCT/EP2016/078198 filed 18 Nov. 2016, which claims priority to International Application No. PCT/EP2015/002331 filed 20 Nov. 2015. The entire contents of these applications are hereby incorporated herein by reference.

The present invention generally relates to a process suitable for extracorporeal lung support. The process comprises contacting blood with a dialysis liquid via a semipermeable membrane. Either the blood or the dialysis liquid, or both, become oxygen-enriched, prior, after or simultaneously to said contacting step. For oxygen-enrichment of the dialysis liquid, a net transfer of oxygen from the dialysis liquid to blood occurs across the semipermeable membrane. The step of contacting further allows for removal of undesired substances from blood directly to the dialysis liquid across the semipermeable membrane. Thereby, an efficient extracorporeal lung support is provided.

INTRODUCTION

Metabolite Transport in the Blood

For the survival of a human or animal, adequate oxygenation of the whole organism is important. Molecular dioxygen, $O_2$, is essential for cellular respiration in all aerobic organisms. Red blood cells (erythrocytes) take up oxygen in the lungs and are responsible for carrying oxygen throughout the body. The chemical entity in red blood cells that binds oxygen in the lungs is the protein hemoglobin, particularly the heme moieties of hemoglobin.

As a result of metabolic activity, the human or animal body produces carbon dioxide, $H^+$ ions and other metabolites. In general, in the vertebrate (human or animal) body, carbon dioxide is produced in peripheral tissues as a result of metabolic activity. In the capillaries of peripheral tissues, carbon dioxide produced in the tissues diffuses down its partial pressure gradient into the blood, mainly into the erythrocyte. In the vertebrate body, there are three major ways in which carbon dioxide is transported in the blood: (a) dissolved $CO_2$ (carbon dioxide is much more soluble in blood than oxygen), (b) bound to blood proteins, such as hemoglobin and plasma proteins, and (c) in the form of the ion pair: bicarbonate ions and $H^+$ ions. In a resting adult human being, approximately 10 mmol $CO_2$ are produced per minute. Further, every minute approximately 8 mmol $H^+$ ions are produced in the erythrocytes (appr. 15000 mmol/day). Calculated based on the amount of blood in an adult human being (5 l), 10 mmol $CO_2$ are loaded per minute into 5 l of blood, i.e. 2 mmol $H^+$ ions per l of blood.

The kidney typically accounts for a removal of approximately 100 mmol $H^+$ ions/day.

On molecular level, protein-bound carbon dioxide (b) reversibly binds to blood proteins, such as hemoglobin and plasma proteins, by associating with amino groups of blood proteins, e.g. hemoglobin, to form carbamino proteins, e.g. carbaminohemoglobin. Thus, carbon dioxide does not typically bind to iron, as oxygen does, but to amino groups of the hemoglobin protein and to amino groups on the polypeptide chains of other blood proteins, particularly plasma proteins. Bicarbonate ions (c), originate from carbon dioxide which, following its entry into red blood cells (erythrocytes), combines with water to form carbonic acid ($H_2CO_3$). This reaction is mainly catalyzed by the enzyme carbonic anhydrase, which is found inter alia in red blood cells. The enzyme is also found in the lung endothelium and at other sites of the body. Carbonic acid then dissociates to form bicarbonate ions ($HCO_3^-$) and hydrogen cations:

$$CO_2 + H_2O \leftrightarrows H_2CO_3 \leftrightarrows HCO_3^- + H^+$$

The reactants (educts and products) of this reaction are present in dynamic equilibrium—as qualitatively indicated by the arrows ($\leftrightarrows$) in the above equation. Addition or removal of one or more reactants (be it in vivo or in vitro) causes, by Le Chatelier's principle, a shift of the reaction, in accordance with the equilibrium. Carbonic anhydrase is not strictly required for this reaction to occur as such; however, it is important for efficient conversion.

Oxygen, carbon dioxide and $H^+$ ions are mainly transported in the blood, and the gas exchange (oxygen, carbon dioxide, water) with the surrounding air occurs in the lungs.

Within the human or animal body, fluids such as blood must be maintained within the narrow pH range, e.g. in the human body preferably in the range of pH 7.35 to 7.45, i.e. slightly alkaline. The metabolites transported in the blood, such as carbon dioxide ($CO_2$), can influence the blood pH.

As a result of metabolic activity, the human or animal body also produces not only carbon dioxide, but also acidic organic molecules. The acidic organic molecules are a further source of $H^+$ ions. The presence of $H^+$ ions influences the blood pH. However, within the human or animal body, fluids such as blood must be maintained within the narrow pH range, e.g. in the human body in the range of pH 7.35 to 7.45, i.e. slightly alkaline. Buffering of the blood is therefore important. When a subject suffers from a condition associated with excess amounts of $H^+$ ions, the buffering capacity of the blood is usually insufficient to maintain the blood within that pH range.

In general, the hydrogen cations which are formed when carbonic acid dissociates into hydrogen cations and bicarbonate ions, can bind to proteins in the blood, particularly in the erythrocyte. The major intracellular hydrogen cation acceptor, or buffer for binding of hydrogen cations is the protein hemoglobin. Hemoglobin, and to a lesser extent plasma proteins, are capable of buffering the pH of the blood, e.g. an excess of hydrogen cations. The buffering of hydrogen cations minimizes the pH change of the blood as the blood traverses the tissue capillaries. However, the buffering capacity is not unlimited, and thus, acidosis can occur. The hydrogen cations primarily bind to the histidine side chains of hemoglobin.

Bicarbonate serves a crucial biochemical role in the physiological pH buffering system. In the healthy vertebrate (human or animal) body, (a) about 5% of carbon dioxide is transported unchanged, dissolved in the plasma; (b) about 10% of carbon dioxide is transported bound to blood proteins, particularly hemoglobin and plasma proteins; and (c) the majority of carbon dioxide is transported in the form of bicarbonate ions and hydrogen cations; the hydrogen cations are mainly bound to proteins.

In the respiratory organs of the healthy human or animal body, the lungs, carbon dioxide is released; thereby the partial pressure of $CO_2$ ($pCO_2$) is decreased. Normal values of $pCO_2$ in a (human) subject's arterial blood are in the range 35-45 mmHg. A $pCO_2$ of more than 45 mmHg is referred to herein as "high $pCO_2$" or "increased $pCO_2$". Hypoventilation is one possible cause of high $pCO_2$. If the $pCO_2$ in a subject's arterial blood is higher than 45 mmHg, the subject may need a treatment in order to reduce $pCO_2$.

The term acidosis refers to an increased acidity in the mammalian body. Acidosis can be determined by measuring the pH of a subject's bodily fluids, particularly blood plasma, more particularly arterial blood plasma. In mammals, particularly humans, acidosis is characterized by a pH of arterial blood plasma of below 7.35. Blood pH values of below 6.8 are usually not tolerated by a human or animal body since a pH outside this range usually results in irreversible cell damage. Thus, acidosis is characterized by a pH of arterial blood plasma of 6.8 to less than 7.35.

In general, subjects suffering from acidosis can be grouped into two major subgroups, based on the molecular causes of acidity in the blood plasma: respiratory acidosis and metabolic acidosis. Metabolic acidosis, on a molecular level, is caused by an increased amount of acidic organic molecules, caused by increased production of organic acids (e.g. lactic acid) as a result of increased metabolic activity and/or by disturbances in the ability to excrete acid via the kidneys. Respiratory acidosis, on a molecular level, results from a build-up of carbon dioxide in the blood due to decreased ventilation (hypoventilation). It is usually caused by malfunction of the lungs.

Head injuries, drugs (especially anesthetics and sedatives), and abnormalities of the central nervous system, such as brain tumors, can be causative for this condition as well. It can also occur as a compensatory response to chronic metabolic alkalosis. If respiratory acidosis persists, e.g. in case of diseases compromising pulmonary function, such as late-stage emphysema and muscular dystrophy, such compensatory mechanisms, i.e. extraneous bicarbonate infusion, cannot efficiently reverse the accumulation of carbon dioxide associated with uncompensated respiratory acidosis. Under such circumstances, the use of a lung support may be indicated.

In practice, patients exhibiting symptoms of both conditions exist. A given subject may suffer from any one of (i) metabolic acidosis, or (ii) respiratory acidosis, or (iii) a combination of metabolic and respiratory acidosis.

Prior Art Systems for Lung Support

One of the major breakthroughs in medicine was the invention—and later use—of mechanical ventilation for subjects suffering from respiratory failure. In Germany each year more than 240.000 subjects are mechanically ventilated with an average treatment period of 10 days. The average mortality of these subjects is 35%. If another organ dysfunction occurs together with respiratory failure, the mortality can increase up to 75%.

Mechanical ventilation is a method to mechanically assist or replace spontaneous breathing, i.e. a method of lung support. Mechanical ventilation may involve a machine (ventilator), or the breathing may be assisted by a healthcare professional, such as a nurse or a physician. In either case, mechanical ventilation may involve a device penetrating into the subject's body ("invasive mechanical ventilation"), i.e. either penetrating through the mouth (such as an endotracheal tube) or penetrating through the skin (such as a tracheostomy tube). There are two main modes of mechanical ventilation: positive pressure ventilation, where a gas (e.g. air) is pushed into the trachea, and negative pressure ventilation, e.g. by placing the patient's chest into a low pressure chamber, which causes extension of the chest, and thus sucking of air into the patient's lungs. Besides all the positive effects of mechanical ventilation there are also undesired disadvantages: undesired consequences can include, without limitation, the following: reduction in blood perfusion of internal organs, e.g. liver, by up to 30%, decrease in blood pressure, increase in intra-abdominal pressure, decrease in the excretory renal function, ventilator-induced lung injury (VILI), barotrauma, volutrauma, atelectrauma, and biotrauma, acute respiratory distress syndrome (ARDS), pneumonia, dyspnea of sedated subjects treated in an intensive care unit (ICU), weaning after about 48 h ventilation (see e.g. Larsen and Ziegenfuß, Beatmung, Springer, Berlin Heidelberg, 2013; and Schmidt et al., Intensive Care Med., vol. 40, pp. 1-10, 2014).

Some of the undesired consequences of mechanical ventilation can be addressed by extracorporeal lung support systems. These systems aim at extracorporeal blood oxygenation, or at extracorporeal blood carbon dioxide removal. Today extracorporeal membrane oxygenation (ECMO) is one of the most common treatments for extracorporeal lung support used to assist or lung replace the function of the lungs. Blood is removed from the body and introduced into a device having a membrane (porous membrane for short term treatments or a non-porous membrane for long term treatments) separating the blood from a gas phase (oxygen, or gas mixture comprising oxygen), which allows for oxygenation of the blood. Since the extracorporeal blood flow rates during ECMO are similar to the cardiac output of up to about 7 l/min, it is possible to combine ECMO with heart support, by including a pump in the system (ECLS, extracorporeal life support). As an alternative to membrane oxygenation, oxygen can be introduced directly into extracorporeal blood, e.g. by means of an oxygen (super)saturated liquid, as described in U.S. Pat. No. 6,344,489 B1 (Wayne State University) and U.S. Pat. No. 6,607,698 B1 (Therox/Wayne State University). However, the extracorporeal introduction of a liquid typically increases the volume of the blood; therefore volume reduction prior to re-introduction of the gas-enriched blood into the human or animal body is required. Introduction of a gas-saturated or gas-supersaturated liquid increases the risk of bubble formation. However, in general, the presence of bubbles, particularly oxygen bubbles, can cause undesired denaturation of blood proteins, and therefore, application of these methods and systems requires utmost care in order to minimize bubble formation. Alternatively, blood may be oxygenated directly, i.e. without a gas exchange membrane, e.g. by injecting oxygen into the blood by means of a bubble oxygenator. This method is associated with undesired foam formation and with the risk of gas embolism. This method is not suitable to treat acidosis.

Some prior art methods rely on high blood flow rates and especially high sweep gas flows; however, this can cause gas embolism on the blood side. As a remedy, an arterial filter can be foreseen; however, this increases the risk of a foreign body reaction.

The treatment of subjects with impaired lung function by oxygenation alone does not fully substitute the function of the lung. Systems and methods, mainly for extracorporeal carbon dioxide removal ($ECCO_2R$) have been developed. Such treatment can be indicated e.g. in case of respiratory acidosis. As reviewed by Baker et al., J. Intens. Care Soc., 13: 232-236 (2012), $ECCO_2R$ systems typically rely on the use of a gas exchange membrane, across which carbon dioxide diffuses from the extracorporeal blood into a gas chamber. According to that article, the AV-$ECCO_2R$ system (Novalung, Germany) is by far the most widely used $ECCO_2R$ technique. This system relies on contacting blood in an extracorporeal circuit with a gas-permeable membrane, having a gas (oxygen, or gas mixture comprising oxygen) as a "sweep gas" on the other side of the membrane, thereby allowing carbon dioxide gas to cross the membrane and to remove it from the gas chamber by the flow of sweep gas.

For example, WO 2010/091867 A1 (Novalung) describes an apparatus for treatment of a biological liquid in a three-chamber-system. A first chamber is suitable for receiving a biological liquid such as blood, and a second chamber, separated from the first chamber by a gas-permeable but liquid-impermeable membrane, is capable of optionally receiving a gas such as oxygen. Owing to the gas-permeability of the membrane, carbon dioxide gas can diffuse from the first chamber into the second chamber (thus providing $ECCO_2R$), and, optionally, oxygen gas can diffuse from the second chamber into the first chamber, and thus an extracorporeal lung support is provided. Small molecules, such as water, can be removed from the first chamber across a liquid-permeable membrane into a third chamber. This three-chamber system is relatively complicated, and can be associated with a disadvantageously high flow resistance. Further, Respiratory Dialysis® (ALung Technologies), is being offered commercially. This method relies on a sweep gas instead of a dialysis liquid. This method is unsuitable for adjusting the acid-base balance and/or electrolyte homeostasis of the blood, and is not suitable for traditional dialysis devices (Cove et al. Critical Care 2012, 16:232).

In general, the efficiency of both blood oxygenation and blood carbon dioxide removal is dependent on the blood flow rate, and the following holds: the higher the blood flow rate, the better the oxygenation for the whole subject (e.g. patient), and the lower the blood flow rate, the better the carbon dioxide removal from the blood ($ECCO_2R$). Typically, high-flow (suitable for ECMO) refers to >2400 ml/min; mid-flow (suitable for both ECMO and $ECCO_2R$) refers to 800-2400 ml/min, and low flow (suitable for $ECCO_2R$) refers to <800 ml/min. For state of the art $ECCO_2R$, a lower blood flow rate than for ECMO (i.e. about 2 l/min or less) is suitable. Such blood flow rates are realized e.g. in the commonly used pECLA (pump-less extracorporeal lung assist).

Liquid breathing is an alternative form of lung support in the state of the art. In this method, an organism (e.g. human) breathes an oxygen-rich liquid (such as a perfluorocarbon), instead of breathing air, in methods of TLV (total liquid ventilation) or PLV (partial liquid ventilation), whereby PFC (perfluorocarbon) containing liquid is flooded into the lungs by a mechanical ventilator for transporting breathing gases such as oxygen and carbon dioxide (Lachmann et al., Intensivmed. und Notfallmed., vol. 34, pp. 513-526 (1997). A standard mode of application for liquid breathing has not been established yet.

In the state of the art, the withdrawal of a subject's blood into an extracorporeal circuit is practiced not only for the purposes of lung support (oxygenation and/or $CO_2$ removal), but alternatively for the purpose of supporting other organs, such as liver or kidney. Such methods typically involve the contacting of blood with a dialysis liquid across a semipermeable membrane, thus allowing the transfer of the undesired substances from the blood along the concentration gradient to the dialysis liquid, and optionally of desired substances in the opposite direction. These prior art systems are directed at other purposes, i.e. kidney support and/or liver support. For example, dialysis for kidney support can be indicated in case of acidosis, which can result from chronic renal failure (CRF). WO 03/094998 A1 (Hepa Wash) describes an apparatus and a method for the removal of protein-bound substances (particularly toxins) from blood, which relies on an absorber liquid which is suitable as dialysis liquid for liver dialysis, wherein the dialysis liquid comprises albumin, and may optionally comprise caffeine, both for the purpose of binding of toxins to albumin. These prior art methods are, however, not directed at an efficient removal of carbon dioxide ($CO_2$), hydrogen cation ($H^+$) and hydrogen carbonate ($HCO_3^-$), nor at oxygenating blood. Thus, such methods are not adapted for substituting malfunction of the lungs; in particular, they are not adapted for oxygenating blood and for removing carbon dioxide from blood.

Problem to be Solved

The object of the present invention is to provide a novel method suitable for extracorporeal lung support, which provides for oxygenation as well as carbon dioxide removal ($ECCO_2R$). It is also desired to overcome the disadvantages associated with blood air contact in traditional membrane gas exchange devices (e.g. $ECCO_2R$ and ECMO). It is also an object of the invention to provide a lung support with superior quantitative capabilities: for lung support, the removal of $CO_2$ (or alternatively or additionally the removal of the $H^+$/bicarbonate ion pair) has to be in the mmol range. It is thus an object to achieve combined removal of $H^+$ ions and bicarbonate in superior quantities, i.e. in that range. It is yet a further object to provide a single device capable of solving these objects. The inventors found that these and further objects can be achieved by the features defined in the claims.

As a solution to these objects and to problems associated with the prior art, the present invention provides a superior method for extracorporeal lung support. Further advantages of the present invention are associated with elements of the invention which are described in the detailed description below.

Terms and Definitions

Whenever the term "comprising" is used herein, this allows that more than more items than the ones actually listed can be present. However, in some embodiments "comprising", as used herein, is to be read more narrowly, so that it is synonymous to the terms "consisting essentially of" or "consisting of".

Acidosis refers to an increased acidity (i.e. an increased hydrogen cation concentration) in the blood and other body tissue. If not further specified, it typically refers to increased acidity of the blood plasma. Increased acidity typically means that the pH of arterial blood plasma is lower than 7.35, typically 6.8 to less than 7.35.

Bicarbonate equilibrium refers to the equilibrium of carbonic acid and bicarbonate/hydrogen cation:

$$H_2CO_3 \leftrightharpoons H^+ + HCO_3^-.$$

The equilibrium is dynamic and the dissociation occurs spontaneously (i.e. without depending on catalysis by an enzyme such as carboanhydrase).

Bohr effect: In general, the binding affinity of oxygen to hemoglobin is influenced by the pH (and thus by the concentration of hydrogen cations) and by the partial pressure of carbon dioxide ($pCO_2$). Thus, oxygenation of hemoglobin and carbon dioxide removal from hemoglobin mutually influence each other. This phenomenon is referred to as Bohr effect. For reference, as well as for further aspects of the Bohr effect, see R. F. Schmidt, F. Lang, and M. Heckmann, Eds., Physiologie des Menschen. Berlin, Heidelberg: Springer Berlin Heidelberg, 2011; and J. B. West, Respiratory Physiology: The Essentials. Lippincott Williams & Wilkins, 2012.

Buffering agent is used herein to refer to a weak acid or base which is suitable to maintain the acidity (pH) of a solution near a certain value (e.g. near the pKa value of the weak acid or base, e.g. pH=pKa±1), even if an acidic or basic compound is added. The term buffering agent can be used for solid or dissolved compounds alike. Buffering agents are typically soluble in solution, preferably aqueous solution. The function of a buffering agent is to prevent an undesired change in pH when an acidic or basic compound is added to said solution. Salts of the weak acid or base which is suitable to maintain the acidity (pH) of a solution near a certain value can also be referred to as buffering agents.

Carboanhydrase refers to an enzyme which catalyzes the reversible conversion of dissolved carbon dioxide to carbonic acid:

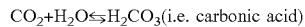

$CO_2 + H_2O \leftrightarrows H_2CO_3$ (i.e. carbonic acid)

Carboanhydrase is naturally present in red blood cells (erythrocytes) and at other sites of the human or animal body.

Dialysis liquid and dialysis liquid are used interchangeably herein.

Erythrocytes or red blood cells or RBCs refer synonymously to blood cells of the vertebrate organism characterized by presence of hemoglobin in the cytoplasm. RBCs take up oxygen in the lungs and release it into peripheral tissues, and take up undesired substances such as hydrogen cations and carbon dioxide in peripheral tissues and release them in the lungs. The release/uptake in peripheral tissues mainly occurs while erythrocytes pass through the capillaries of these tissues.

Extracorporeal refers to any process, activity, substance or device which is present or performed outside the body of a human or animal. If a process, activity, substance or device which is present or performed partially outside the body of a human or animal, the term refers to the part outside the body.

Fluid generally refers to a non-solid state of matter. Typically, a fluid is either a liquid or a gas.

Haldane effect: In general, deoxygenated hemoglobin has the capacity to bind more $H^+$ ions than oxygenated hemoglobin. This aspect pertains to a phenomenon that can be referred to as Haldane effect. The significance of the Haldane effect resides in the fact that oxygenation of hemoglobin (typically in the lungs) promotes dissociation of $H^+$ from hemoglobin (Hb), which shifts the bicarbonate equilibrium towards $CO_2$ formation; therefore, $CO_2$ is released from erythrocytes at the site of oxygenation of hemoglobin. For reference, as well as for further aspects of the Haldane effect, see R. F. Schmidt, F. Lang, and M. Heckmann, Eds., Physiologie des Menschen. Berlin, Heidelberg: Springer Berlin Heidelberg, 2011; and J. B. West, Respiratory Physiology: The Essentials. Lippincott Williams & Wilkins, 2012. Further aspects of the Haldane effect are described in the detailed description of the present invention.

Heme. or Haem, refers to a porphyrin moiety (heterocyclic organic ring) comprising a $Fe^{2+}$ (ferrous) ion contained in its center of a heterocyclic organic ring system (porphyrin). Heme is comprised in hemoglobin.

Hemoglobin or short Hb, is a protein typically present in red blood cells of the vertebrate organism. The peptide chains of hemoglobin contain numerous amino and carboxyl groups. Typically, the hemoglobin molecule is comprised of four globular protein subunits. Each subunit is composed of a protein chain (globin) which is associated with a non-protein heme group. Hemoglobin is capable of reversibly binding small molecules such as metabolites, most notably oxygen ($O_2$), hydrogen cations ($H^+$) and carbon dioxide ($CO_2$) or solvates of any of these. Typically, oxygen can reversibly bind to the heme group. In contrast, carbon dioxide can typically reversibly bind to amino groups (typically at the N-terminals and at side-chains of arginine and lysine residues in hemoglobin), which leads to the formation of carbamino groups. Hemoglobin having one or more carbamino groups is termed carbaminohemoglobin. Carbaminohemoglobin is the major contributor to the Haldane effect. Typically, carbaminohemoglobin is thought to account for about 10% of carbon dioxide transport in mammals. Finally, the carboxyl groups of hemoglobin are capable of binding, and hence buffering, hydrogen cations (such hydrogen cations are formed typically as a result of $CO_2$ dissociation and the bicarbonate equilibrium). Over the normal physiological pH range, much of the binding of hydrogen cations by hemoglobin occurs at the imidazole group of the amino acid histidine, present in the globin chain. Deoxygenated hemoglobin is a better acceptor for hydrogen cations than oxygenated hemoglobin.

Hydrogen carbonate or bicarbonate are used interchangeably to refer to an anion with the chemical formula $HCO_3^-$. Hydrogen carbonate is an intermediate form in the deprotonation of carbonic acid. It is a polyatomic anion. Unless the context dictates otherwise, the term is used herein to the hydrogen anion ($HCO_3^-$), and to any salt of bicarbonate, such as e.g. sodium bicarbonate.

Hydrogen cation or hydrogen ion or $H^+$ are used interchangeably herein to refer to a cationic form of atomic hydrogen. All these terms include collectively cations of all isotopes of hydrogen, particularly proton, deuteron, and triton. In aqueous solution hydrogen cations typically form solvates by addition of one or more water molecules. Such solvates are called hydroxonium ions and can be described by the general formula $H^+(H_2O)_n$; n being an integer such as 0, 1, 2, 3, 4, or more than 4; most typically 1 or 4. The term hydrogen cation can also be used herein to refer to a hydrogen cation in solution or to solvated states of a hydrogen cation.

Metabolite, as used herein, refers to any intermediate or product of the human or animal metabolism. Particular metabolites of importance in the present invention are carbon dioxide, hydrogen carbonate and hydrogen cation.

Oxygen refers herein to molecular dioxygen ($O_2$), unless the context dictates otherwise. Oxygen is essential for cellular respiration in all aerobic organisms, including mammals.

Oxygenated/deoxygenated hemoglobin refer to the oxygenation state of hemoglobin. Since hemoglobin is typically comprised of four hemoglobin protein subunits, each of which can be oxygenated/deoxygenated reversibly, five states of oxygenation are possible: the fully deoxygenated form (all four subunits deoxygenated) is always referred to as "deoxygenated"; the fully oxygenated form (all four subunits oxygenated) is always referred to as "oxygenated". The terms "oxygenated" and "deoxygenated" are also used as relative terms herein: for example, relative to a form of hemoglobin having one subunit oxygenated, the forms having two or three or four subunits oxygenated can all be referred to as "oxygenated" hemoglobin. Conversely, the same form having one subunit oxygenated can be referred to as "oxygenated" hemoglobin relative to a form having no subunit oxygenated (i.e. all subunits deoxygenated). Deoxygenated hemoglobin is also referred to as deoxyhemoglobin. Oxygenated hemoglobin is also referred to as oxyhemoglobin. Herein, the term hemoglobin is used simultaneously for oxyhemoglobin and deoxyhemoglobin, unless the context dictates otherwise. The terms oxyhemoglobin/deoxyhemoglobin do not particularly require a specific quantity of hydrogen cations being bound to the oxyhemoglobin/deoxyhemoglobin protein. The quantity of hydrogen cations being bound is, however, typically correlated with the oxygenation state (see Haldane effect and Bohr effect).

$pCO_2$ refers to the partial pressure of carbon dioxide ($CO_2$) in a fluid, e.g. in blood plasma or dialysis liquid.

$pO_2$ refers to the partial pressure of oxygen ($O_2$) in a fluid, e.g. in blood plasma or dialysis liquid.

Peripheral tissue refers herein to any non-lung tissue (non-gill tissue) of a vertebrate, particularly to non-lung tissue of a mammal.

Plasma refers herein to blood plasma, i.e. the extracellular intravascular liquid fraction of the blood.

pH or pH value refers to the negative of the logarithm to base 10 of the activity of the hydrogen ion. Solutions with a pH less than 7 are acidic and solutions with a pH greater than 7 are alkaline or basic.

pKa is an index to express the acidity of weak acids, where pKa is defined as follows. In general, weak acids are present partially dissociated in aqueous solution according to the following equilibrium:

$$Ka = \frac{[A^-][H^+]}{[AH]}.$$

This equilibrium defines the pKa value as follows:

$pKa = -\log_{10} Ka.$

In general, the smaller the pKa value, the stronger the acid.

Sodium bicarbonate or sodium hydrogen carbonate refer interchangeably to the (water-soluble) chemical compound with the formula $NaHCO_3$ (also known as baking soda or soda or bicarbonate of soda) in any form, e.g. crystalline (e.g. anhydrous or any hydrate), or dissolved in solution, e.g. aqueous solution.

Sodium carbonate refers to the (water-soluble) disodium salt of carbonic acid ($Na_2CO_3$, also known as washing soda or soda ash) in any form, e.g. crystalline (e.g. anhydrous or any hydrate such as heptahydrate or decahydrate), or dissolved in solution, e.g. aqueous solution.

Solvate refers to a solute being surrounded or complexed by solvent molecules. Solvation is an interaction of a solute (e.g. an ion such as hydrogen cation ($H^+$), hydrogen carbonate ($HCO_3^-$)) with the solvent (e.g. water). In the solvated state, the solvate is typically stabilized (as opposed to a non-solvated state). Unless the context dictates otherwise, solvate preferably refers herein to a solute being solvated in water.

Subject or patient refers to an individual human or animal, preferably human. A subject can be healthy or suffering from at least one medical condition, disease or illness. A patient is a subject suffering from at least one medical condition, disease or illness. In the context of this specification, the term patient can designate an individual suffering from any one or more of the specific conditions disclosed herein.

BRIEF DESCRIPTION OF THE FIGURES

FIG. 2: Schematic overview of embodiments of the present invention.

Figure 1:
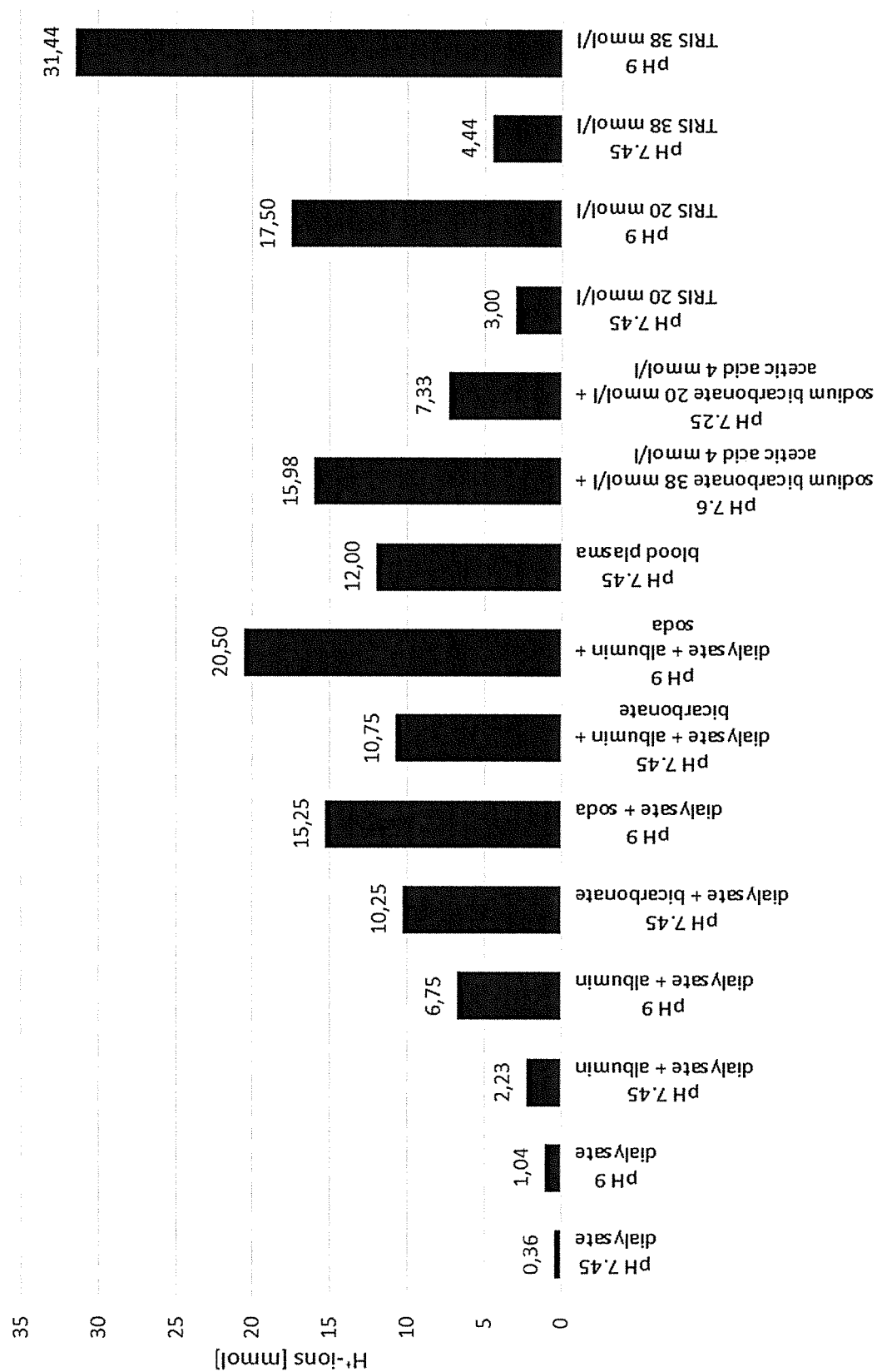
FIG. 1: Results of buffering capacity of solutions comprising bicarbonate and/or albumin (for details, see Example 1).

The numbers used in FIG. 2A to 2D have the following meanings:
1 chamber for blood (first chamber)
2 chamber for dialysis liquid (second chamber)
3 pH measuring unit
4 recirculating pump for dialysis liquid
5 blood pump in extracorporeal blood circuit
6 oxygen/oxygen enriched liquid and/or solid
7 oxygen/oxygen enriched liquid and/or solid
8 oxygen/oxygen enriched liquid and/or solid
9 $H^+$ and/or $OH^-$
10 addition of 6 to extracorporeal blood circuit
11 addition of 7 to extracorporeal blood circuit
12 addition of 8 to dialysis liquid
13 addition of 9 to dialysis liquid
14 adsorber
15 removal of $CO_2$, $HCO_3^-$, $CO_3^{2-}$ and/or liquid and/or dialysis liquid
16 dialysis liquid reprocessing unit
17 single-pass inlet (pump)
18 single-pass outlet (pump)

It is not necessary that all items 1 to 18 are realized in combination. However, the process of the present invention requires at least a chamber for blood (first chamber) and a chamber for dialysis liquid (second chamber). Specific embodiments are provided in the detailed description.

Specific illustrative and non-limiting embodiments are as follows:

In a single-pass embodiment no. 17 and 18 can be realized as pumps, valves, flow-meters, balancing chambers or a combination of the ones mentioned here as it is state of the art for single-pass balancing systems. An additional liquid removal from the dialysis circuit and/or the extracorporeal blood circuit e.g. ultrafiltrate can be realized by No. 18 or by a separate device ahead of No. 18 and following No. 2.

Integration of No. 12-15 or one of these into No. 16 may be realized. No. 12-14 can be combined by one unit or realized separately. No. 6-8 and 10-12 can be realized or just one, two or any combination of these. No. 5 can precede No. 10, positioned in between No. 10 and No. 1, in between No. 1 and No. 11 and following No. 11. No. 4 can be located in between No. 2, No. 3 and No. 12-16. No. 12 can be located ahead of or following No. 13 in the dialysis liquid flow path, but is located preferably following No. 14. No. 14 preferably follows No. 13 in the dialysis liquid flow path.

Figure 3:
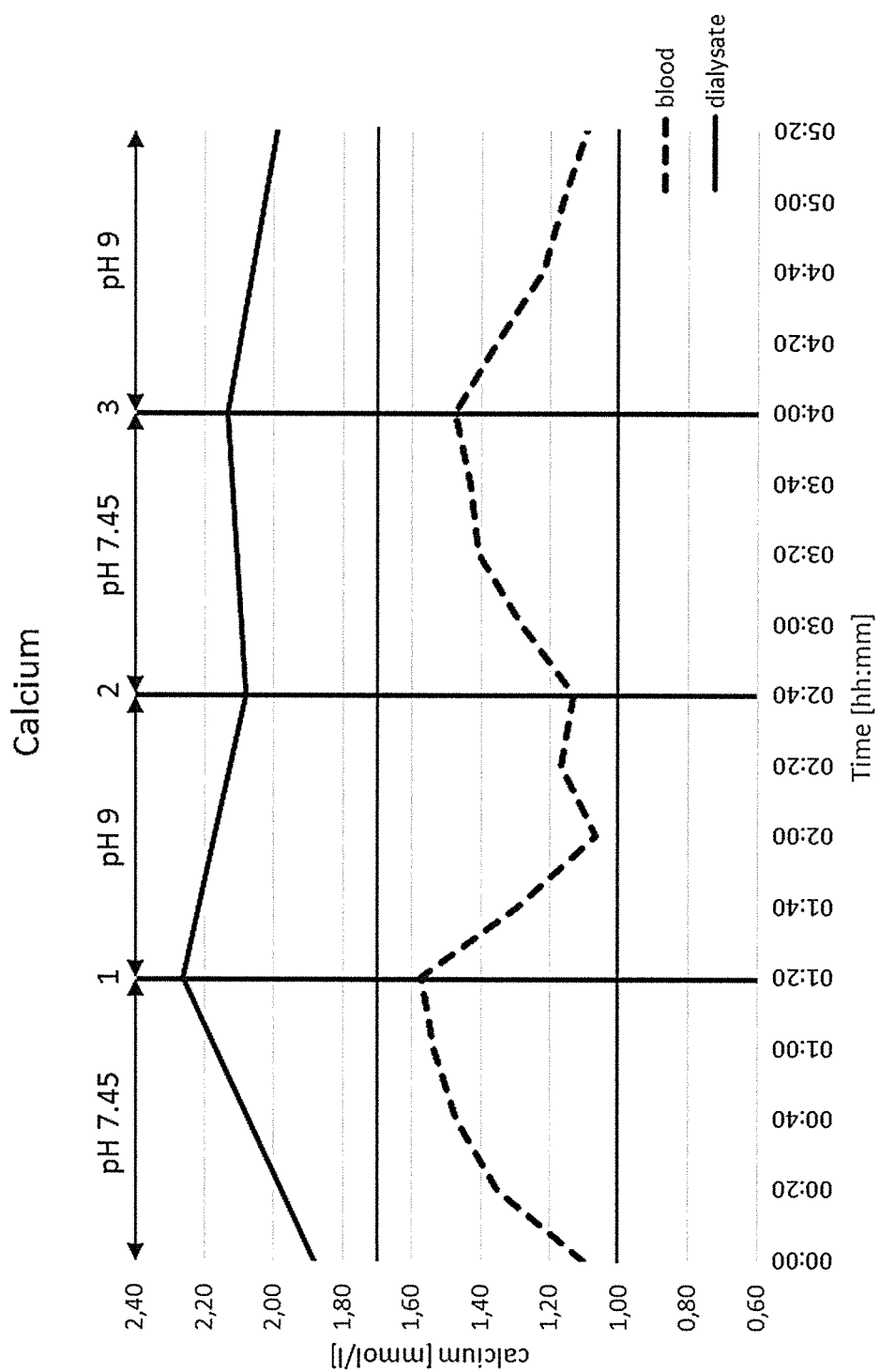
FIG. 3: Calcium levels in dialysis liquid and blood over time (for details, see Example 2).

In the embodiments shown in the panels of this figure, carbon dioxide and/or hydrogen carbonate and/or carbonate and/or hydrogen cations are removed across a semipermeable membrane that separates the first chamber and the second chamber. Oxygenation is performed directly or indirectly according to any one of the following: (B) by introduction of oxygen (e.g. an oxygen-enriched solution) into the dialysis liquid, resulting in an oxygen-enriched dialysis liquid; and/or (C) by introduction of oxygen (e.g. an oxygen-enriched solution) into blood prior to passing through the dialyzer (device for dialysis) and/or (D) by introduction of oxygen (e.g. an oxygen-enriched solution) into blood prior to passing through the dialyzer (device for dialysis). The figure also shows an embodiment wherein the used dialysis liquid is recirculated (recycled). Such recycling is an optional but preferred embodiment. Typically, the recirculation of the dialysis liquid is achieved by at least one pump, preferably with an adjustable flow rate from 10 ml/min to 11000 ml/min. FIG. 3: $Ca^{2+}$ levels in dialysis liquid and blood over time (for details, see Example 2).

Figure 4:
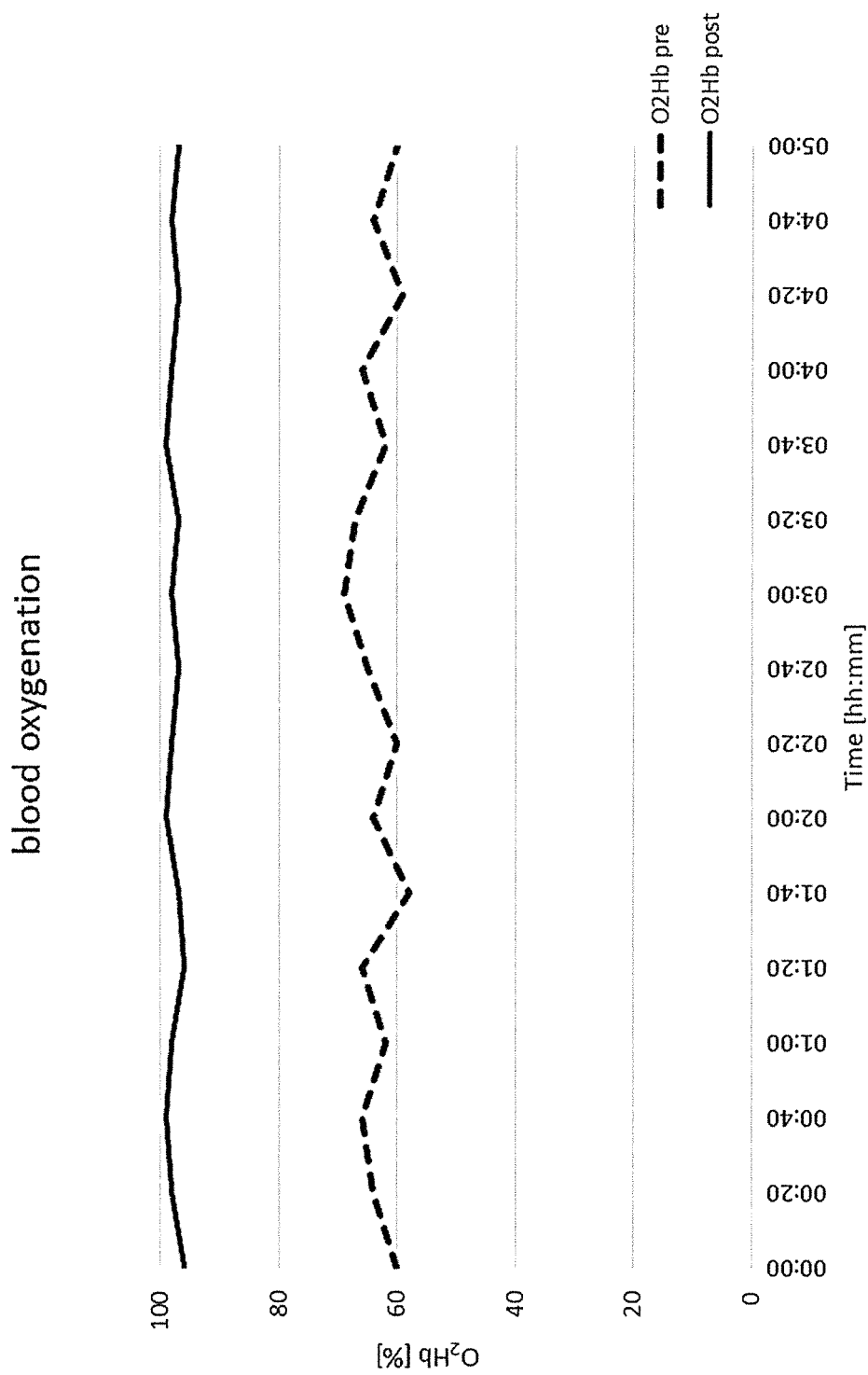
FIG. 4: Results of oxygenation (for details, see Example 3).

FIG. 4: Results of oxygenation (for details, see Example 3).

$O_2Hb$ [%]: Oxygen saturation of hemoglobin (in %)

$O_2Hb$ pre: oxygen saturation of hemoglobin, measured before entry of the blood into the first chamber.

$O_2Hb$ post: oxygen saturation of hemoglobin, measured after exit of the blood from the first chamber.

DETAILED DESCRIPTION

The objects are addressed by the process and method according to the present invention. Thereby, shortcomings of prior art methods or processes are overcome. In particular, the present inventors found that advantages over conventional methods or processes for extracorporeal lung support, which rely on a gas phase for lung support, can be achieved by using a liquid dialysis fluid (dialysis liquid) in a method for extracorporeal lung support. This method allows to effectively oxygenate blood, to remove carbon dioxide from the blood and/or to adjust the blood pH to a desired or normal value and/or to adjust (increase or decrease) the bicarbonate concentration in the blood. Therefore the method enables an efficient and versatile lung support, and can support further organs, based on the needs of individual subjects.

The inventors found that, in the liquid/liquid dialysis method of the present invention, the Haldane effect and/or the Bohr effect can be taken advantage of. The present invention is, however, not limited to a particular choice effect or to a particular theory for explaining any of these effects. More generally speaking, the invention is based inter alia on the discovery that the binding of certain substances to hemoglobin can be favorably exploited when blood is contacted with a dialysis liquid as defined herein and blood is directly or indirectly oxygenated as described herein.

The respective effect can be systematically taken advantage of outside the body, i.e. for removal of metabolites from blood in the method for blood oxygenation according to the present invention. This allows for more efficient extracorporeal lung support than conventional methods.

The Haldane effect has been described previously as a phenomenon occurring in the vertebrate body. Herein, as well as in the prior art, Haldane effect generally refers to the phenomenon that the binding affinities of hemoglobin ligands, in particular oxygen, carbon dioxide and hydrogen cation ($H^+$), to hemoglobin are not static, i.e. not identical at all conditions, so that, generally speaking, when a ligand is released from hemoglobin or becomes bound to hemoglobin, this can result in the binding affinity for another ligand being increased or decreased. In the healthy vertebrate (human or animal) body, the Haldane effect is observed in peripheral tissues, particularly in capillaries of peripheral tissues (where oxygen is released from hemoglobin), and in the lungs, (where oxygen becomes bound to hemoglobin). To further illustrate the present invention, the Haldane effect is generally explained herein by an illustrative description of phenomena occurring (1) in peripheral tissues and (2) in lungs of the healthy human or animal body, as follows:

(1) In general, in the vertebrate (human or animal) body, carbon dioxide is produced in peripheral tissues as a result of metabolic activity. In the capillaries of peripheral tissues, carbon dioxide produced in the tissues diffuses down its partial pressure gradient into the blood, mainly into the erythrocyte. As described above, carbon dioxide is present in dynamic equilibrium with carbonic acid and the pair of bicarbonate/hydrogen cation. The hydrogen cations, in turn, can bind to proteins in the blood, particularly in the erythrocyte. The major intracellular hydrogen cation acceptor, or buffer for binding of hydrogen cations is the protein hemoglobin. The hydrogen cations primarily bind to the histidine side chains of hemoglobin. When oxygen is released from the heme of hemoglobin, i.e. when oxyhemoglobin becomes deoxygenated, the affinity of hemoglobin for hydrogen cations increases. Thus, at this stage, the hemoglobin becomes a stronger base or weaker acid, making more sites available to buffer hydrogen cations. In other words, deoxyhemoglobin has a higher affinity for protons than oxyhemoglobin. Thus, hydrogen cations become bound to hemoglobin (deoxyhemoglobin) upon release of oxygen. The binding of hydrogen cations to hemoglobin, and thus the withdrawal of free hydrogen cations from the blood, causes, by Le Chatelier's principle, a shift of the reaction

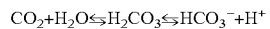

to the right. Further, deoxygenated hemoglobin favors the binding of hydrogen cations, and thus the formation of bicarbonate. The formation of bicarbonate increases the blood's capability to carry carbon dioxide.

(2) In general, in the lungs of a healthy human or animal, when oxygen becomes bound to the heme of hemoglobin (i.e. deoxyhemoglobin becomes oxygenated), the Haldane effect is responsible for a reversal of the above reactions: shortly, oxygenation of hemoglobin promotes dissociation of hydrogen cations from hemoglobin, which shifts the bicarbonate buffer equilibrium towards $CO_2$ formation; so that $CO_2$ is released from erythrocytes. In the respiratory epithelium, carbon dioxide diffuses down its partial pressure gradient from the respiratory surfaces to the environment. This diffusion and the consequent decrease in the intracellular carbon dioxide tension generate a disequilibrium for the reaction of bicarbonate and carbon dioxide, and thus bicarbonate is dehydrated to carbon dioxide (typically aided by the enzyme carboanhydrase in the erythrocytes). The hydrogen cations required for this reaction are released from hemoglobin. Thus, hydrogen cations are released from hemoglobin upon binding of oxygen. The dissociated hydrogen cation reacts with bicarbonate ($HCO_3^-$) to form carbonic acid ($H_2CO_3$), and said carbonic acid further reacts— typically aided by the enzyme carboanhydrase which is present in erythrocytes—to water and $CO_2$, the binding of oxygen to hemoglobin favors the shifting of the bicarbonate buffer equilibrium towards $CO_2$ formation. In the lungs of the healthy vertebrate (human or animal) body, $CO_2$ is then typically released from the red blood cells as a consequence of oxygenation of hemoglobin.

The fact that the binding affinity of oxygen to hemoglobin is influenced by the pH (and thus by the concentration of hydrogen cations) and by the partial pressure of carbon dioxide ($pCO_2$) is also referred to as Bohr effect.

Thus, in general, deoxyhemoglobin can bind more hydrogen cations (has a higher affinity for hydrogen cations) than oxyhemoglobin: It is widely accepted that the molecular reason for this phenomenon resides in the fact that hydrogen acceptor moieties of deoxyhemoglobin, like imidazole of histidine side chains, are more capable of binding hydrogen cations (have a higher affinity for binding hydrogen cations) than the same or equivalent hydrogen acceptor moieties of deoxyhemoglobin. Without wishing to be limited by a particular theory, it is thought that the electron structure of the globin peptide chain is altered during binding or release of oxygen, thereby causing the change in hydrogen cation affinity. This phenomenon allowing that deoxygenation of hemoglobin promotes association of hydrogen cations to hemoglobin, which shifts the bicarbonate buffer equilibrium towards bicarbonate ($HCO_3^-$) formation; so that the $CO_2$ transport capacity of blood increases, and vice versa, is called the "Haldane effect". Owing to the Haldane effect, deoxygenated hemoglobin (deoxyhemoglobin) has a higher ability to neutralize (buffer) $H^+$ ions than oxygenated hemoglobin (oxyhemoglobin). In the healthy vertebrate (human or animal) body, the Haldane effect is an important mechanism for facilitating the transport of $CO_2$ by minimizing changes in free $H^+$ or blood pH.

In the present invention, the Haldane effect can be taken advantage of, so that oxygenation and carbon dioxide removal influence each other in a positive way. However, the present invention uses the benefits of the Haldane effect outside the human or animal body. The method of the invention for an extracorporeal lung support comprises both functions, the carbon dioxide removal and the blood oxygenation, which are necessary for a complete lung support. Yet, the carbon dioxide removal unit and the blood oxygenation unit are spatially separated in the process of the invention.

The present invention allows to remove at least one undesired substance from blood, wherein the undesired substance is selected from the group consisting of carbon dioxide ($CO_2$), hydrogen cation ($H^+$), hydrogen carbonate ($HCO_3^-$). For removing at least one undesired substance from blood, the process of the invention does not require a gas exchange membrane (i.e. a membrane having on at least one side blood and on the other side a gas phase). Instead, the removal of the undesired substance occurs across a semipermeable membrane having a liquid on both sides of the semipermeable membrane, i.e. blood on one side and a dialysis liquid on the respective other side. The present invention enables separate regulation and control of the oxygenation and of removal of the at least one undesired substance. Furthermore, the present invention enables to adjust a specific carbon dioxide removal rate, oxygenation or (over)oxygenation rate of the blood and to adjust the blood pH to a desired level.

The present invention also allows to stabilize the blood pH, or to adjust the blood pH to a desired or normal value. Typically, a desired or normal value of blood pH lies in the range of pH 7.35 to 7.45, preferably 7.36 to 7.44, more preferably 7.37 to 7.43, more preferably 7.38 to 7.42, more preferably 7.39 to 7.41, and most preferably about 7.40. More generally, the blood pH range of 20 pH 6.8 to pH 8.0 may be acceptable.

In its broadest sense, the present invention thus provides (i) a process oxygenating blood, comprising the step of exposing blood to a dialysis liquid separated by a semipermeable membrane, wherein the dialysis liquid has the properties or preferred properties defined herein; and (b) a process oxygenating blood, comprising the steps: (i) introducing blood into a first chamber of a device, said device comprising a first chamber and a second chamber, wherein the first chamber and the second chamber are separated by a semipermeable membrane, (ii) introducing a dialysis liquid into a second chamber of said device, wherein the dialysis liquid being introduced into the second chamber. In this specification, the term first chamber is generally used to refer to a chamber configured or suitable to receive blood, and the term second chamber is generally used to refer to a chamber configured or suitable to receive a dialysis liquid; typically, the first and second chamber are separated from each other by a semipermeable membrane as defined herein. Typically, no direct connection (tubing or the like) exists for the first chamber and the second chamber. Thus, only those substances which are capable of traversing the semipermeable membrane can migrate from the first chamber into the second chamber and/or from the second chamber into the first chamber.

Blood and the dialysis liquid are aqueous fluids. The term aqueous is generally used herein to refer to water or water-containing fluids, particularly but without limitation to the liquid state thereof. The term aqueous is used herein to refer to fluids, particularly liquids or liquid phases, comprising water. Typically, aqueous liquids comprise more than 50% (vol./vol.) water, and are hydrophilic. Blood and the dialysis liquid are such aqueous liquids.

In particular, a process for extracorporeal lung support, allowing extracorporeal oxygenation of blood, is provided herein, which is characterized by the following steps:
(i) introducing oxygen into blood and/or into a dialysis liquid,
wherein the dialysis liquid is characterized by a pH the range from pH 6.8 to pH 11; and wherein the dialysis liquid comprises albumin, preferably 10 to 60 g/l albumin;
thereby generating oxygen-enriched blood and/or oxygen-enriched dialysis liquid; and
(ii) exposing said blood to said dialysis liquid separated by a semipermeable membrane.

Ideally, step (i) precedes step (ii). Alternatively, it is possible, that steps (i) and (ii) are carried out simultaneously. In any case, either the blood or the dialysis liquid, or both, become oxygen-enriched in step (i). In case of oxygen-enrichment of the dialysis liquid, a net transfer of oxygen from the dialysis liquid to blood occurs across the semipermeable membrane during the step of contacting. The step of contacting further allows for the removal of undesired substances from blood directly into the dialysis liquid.

At any rate, in step (ii), the flow of blood and the flow of dialysis liquid are preferably not realized in counter-current mode; i.e. blood and dialysis liquids do not flow in opposite directions to each other. In other words, it is preferable that dialysis liquid and blood flow in the same direction through the device of the present invention (co-current). The co-current mode is particularly preferably when the blood is cooled to a temperature below 37° C.

In the event that the blood is contacted with the dialysis liquid and with oxygen at the same time, e.g. in the event that the device of the present invention comprises in addition to the first chamber for receiving blood and the second chamber for receiving dialysis liquid, a third chamber for receiving oxygen (e.g. oxygen gas, gaseous mixture comprising oxygen or oxygen-enriched liquid), so that the third chamber and the first chamber are in contact with each other via a gas-permeable membrane, then the oxygen is preferably passed through the third chamber in counter-current mode with respect to the first chamber.

It is a fundamental difference between the present invention and gas-based extracorporeal carbon dioxide removal methods of the prior art ($ECCO_2R$) that the present invention employs a dialysis liquid.

The present inventors found that the method of the present invention is particularly suitable for the purposes of oxygenating blood, extracorporeal carbon dioxide removal, and for adjustment of bicarbonate levels. These goals can be achieved in personalized medicine, i.e. depending on the needs of an individual patient. Since the present invention allows to increase or decrease the oxygen affinity of hemoglobin outside the human or animal body, it is possible to adjust the oxygen uptake to the needs of an individual patient by changing the conditions within the limits of the present invention, as described in the following. Particular, preferred and advantageous embodiments of the present invention are provided in this description and in the enclosed claims. It is also possible to adjust the blood plasma concentration of carbonate, the blood plasma concentration of bicarbonate, and the ratio of carbonate to bicarbonate in the blood plasma, (a) by using an appropriate dialysis liquid within the framework of the present invention, and (b) by oxygenating blood, thereby causing removal of an undesired substance from blood. For example, the ratio of carbonate to bicarbonate in the blood plasma is dependent on pH and can be influenced by choosing a dialysis liquid with an appropriate pH.

Blood

In the vertebrate (human or animal) body, blood is composed of blood cells and blood plasma (also referred to as "plasma"), so that the blood cells are suspended in the plasma. In the vertebrate body, the major component of plasma is water, and the major type of blood cells are erythrocytes. The methods of the present invention are suitable for being applied to all types of blood from humans or animals, preferably vertebrates, preferably mammals, and most preferably humans.

Whenever reference to blood is made herein in the context of a first chamber, or of a dialysis unit, or of a dialyzer, or in any other extracorporeal context, this need not necessarily mean pure blood, as taken from the human or animal body. In some embodiments, the term blood can refer to a mixture of blood, as taken from the human or animal body, and an acceptable additive in an acceptable amount. An additive is acceptable if the function of the blood is not significantly negatively affected. The amount of the additive is acceptable, if addition of the additive does not result in a significant volume increase of the blood, as taken from the human or animal body, so that the volume of the blood increases by not more than 50%, preferably not more than 40%, not more than 30%, not more than 20%, not more than 10%, not more than 5%.

In some embodiments, the process of the present invention relates exclusively to in vitro activities. In alternative embodiments, the process is exploited to address medical needs of a living subject, as described in detail below; in these alternative embodiments, the contacting of blood via a semipermeable membrane with a dialysis liquid also occurs in vitro, (i.e. outside the body of a human or animal), or extracorporeal. Additionally, interaction with the human or animal body occurs, as described below.

Oxygen-Enrichment of Blood and/or Dialysis Liquid

The process of the present invention comprises the step of introducing oxygen into blood and/or into the dialysis liquid according to the present invention.

If oxygen is introduced into the dialysis liquid, it is typical that the oxygen is introduced into the dialysis liquid in a step preceding or parallel to the step of exposing blood to the dialysis liquid separated by the semipermeable membrane. Thereby, a net transfer of at least a fraction of said oxygen occurs from the dialysis liquid to the blood.

The blood being subjected to oxygen-enrichment is typically blood with a low oxygen content. Such blood is referred to as deoxygenated blood. The deoxygenated blood typically originates from the vein of a human or animal subject.

The step of introducing oxygen into (said deoxygenated) blood and/or into a dialysis liquid is followed by—or concurrent with—a step of contacting blood and dialysis liquid via a semipermeable membrane, allows transfer of small molecules including oxygen across the semipermeable membrane. Either location of the oxygenation step (introduction of oxygen into the deoxygenated blood or introduction of oxygen to the dialysis liquid) may result in oxygenated blood, i.e. blood having an increased oxygen concentration. In other words, for introduction of oxygen into the deoxygenated blood, a step of "direct" oxidation of blood is provided; for introduction of oxygen into the dialysis liquid, a step of "indirect" oxidation of blood is provided. At any rate, at least one site for oxygen to be introduced is typically provided along the flow path of e.g. dialysis liquid or blood.

For indirect blood oxygenation by means of introducing oxygen into the dialysis liquid (rather than directly into blood), followed by exposing the oxygen-enriched dialysis liquid to blood separated by a semipermeable membrane, as described herein, oversaturating the blood with oxygen is not usually possible because the oxygen diffusion is driven by the concentration gradient. This is desired in many instances. In case of a convective transport of oxygen-enriched dialysis liquid oversaturating the blood with oxygen is possible.

In general, the oxygen can be introduced into the blood and/or into the dialysis liquid in many different ways. Preferred examples thereof are described in more detail below.

However, it is preferred that the oxygen introduced into the blood (i.e. in "direct" oxygenation) is not gaseous oxygen. Preferably, "gaseous" oxygen is understood to reflect oxygen in the gas phase, but not liquids or solids containing gaseous oxygen (e.g., in the dissolved state/phase). In particular, it is preferred that in step (i) of the process described herein oxygen is introduced into the blood and the oxygen introduced into the blood is not gaseous oxygen. More preferably, "gaseous" oxygen is also understood to comprise liquids containing bubbles of gaseous oxygen.

It is also preferred that oxygen is introduced into the dialysis liquid. For example, gaseous oxygen may be introduced into the dialysis liquid in order to dissolve. By those measures, a direct contact of the blood with a gas is avoided. Direct contact of the blood with a gas may result in bubbles, which can cause disturbances in the blood, such as foam formation, and which may even cause gas embolism. Furthermore, direct contact of the blood with a gas may also result in coagulation and/or inflammatory reactions. Therefore, direct contact of the blood with a gas is preferably avoided. However, in the process according to the present invention blood may be contacted with a liquid comprising gaseous oxygen. In other words, the gaseous oxygen may be dissolved in a liquid, which is in particular an oxygen-enriched liquid.

Accordingly, it is preferred that the oxygen introduced into the blood and/or into the dialysis fluid is introduced by means of liquid oxygen (as explained below, see option (2) below) or an oxygen enriched liquid (as explained below, see for example options (1) and (6) below) and/or solid (as explained below, see for example option (5) below). In particular, "oxygen-enriched" liquid may be understood to comprise a (homogenous) liquid with molecular oxygen dissolved therein, and/or a liquid containing bubbles (of gaseous nature "dissolved" therein). More preferably, "oxygen-enriched" liquid means a homogenous liquid phase with molecular oxygen dissolved therein, i.e. without bubbles (of gaseous nature "dissolved" therein). Regarding the introduction of oxygen, in either case, the introduction can be achieved by any one of the following:

(1) Introduction (preferably infusion) of a liquid comprising dissolved oxygen into blood and/or dialysis liquid, respectively. The liquid can be oxygen-saturated or oxygen-oversaturated.

(2) Introduction (preferably infusion) of liquid oxygen into blood and/or dialysis liquid, respectively; preferably into the dialysis liquid.

(3) Introduction of oxygen across an oxygen-permeable membrane into blood and/or dialysis liquid, respectively.

(4) Introduction (preferably infusion) of gaseous oxygen into blood and/or dialysis liquid, respectively. The introduction can be implemented e.g. by means of a bubble oxygenator.

(5) Introduction of oxygen-containing solids. Such solids contain fixed oxygen that can be released when the solids are introduced into a liquid. Suitable oxygen-containing solids include e.g. xerogels and lyogels, or frozen gas-enriched liquid. Such oxygen-containing solids can be introduced into blood and/or dialysis liquid.

(6) Convective transport of oxygen-enriched liquid.

Herein, infusion generally refers to the introduction of a fluid (liquid or gas, as the case may be) into another fluid, i.e. into dialysis liquid or into blood.

Some aspects of embodiments (1) to (6) will be described in the following.

For option (1), the used liquids can be water, reverse osmosis water, an aqueous NaCl solution, such as buffered saline, glucose solution, dialysis liquid, perfluorocarbons and oils. The oxygen can be either dissolved in the liquid, or present in excess of the maximum solubility in the respective liquid (which causes the liquid to be an oxygen-supersaturated liquid), or oxygen can be present bound to oxygen-binding substances which are dissolved in the liquid. For that embodiment, PFC (perfluorocarbon) are particularly suitable. Thus, a PFC-containing liquid having oxygen bound to the PFC can be introduced.

When oxygenating by introduction of any such liquid, particularly into blood, favorable contact of hemoglobin and oxygen is achieved, and the risk of gas embolism can be avoided. In general, solubility of oxygen in liquids depends on the pressure, temperature and salinity (Weiss (1970), Deep Sea Res. Oceanogr. Abstr., vol. 17, no. 4, pp. 721-735). By variation of these parameters, oxygen-enriched liquid of a desired degree of oxygenation can be prepared and provided. Said liquid can subsequently be used for oxygenating blood and/or dialysis liquid. It is possible to use an oxygen-super-saturated or oxygen-over-saturated liquid, having increased oxygen partial pressure. Such liquid is prepared at high pressure, typically significantly higher than normal atmospheric pressure. To that end, to avoid bubble formation during release of such oxygen supersaturated liquid at a lower pressure, e.g. atmospheric pressure, oxygen super-saturated liquid can be passed through one or more capillaries. Suitable capillaries have an inner diameter (ID) of 0.012-1000 µm and a length of 0.1 mm-1100 mm. Typically, there is a high pressure at one end of the capillary and lower pressure at the other end of the capillary. As any capillary has its specific flow rate of oxygen supersaturated liquid, as a function of its inner diameter, length, pressure difference and the liquid, the total flow rate can be increased by using several capillaries in parallel. Flow rate, and thus oxygenation, can preferably be adjusted by varying the pressure of the oxygen-enriched liquid. This influences concentration of dissolved oxygen in the respective liquid. The oxygen solubility in a liquid is preferably increased by increasing the gas pressure, increasing or decreasing the temperature, decreasing the ion concentration and ionization of the used gas. Further, for option (1), particularly if the oxygen-enriched liquid is introduced directly into blood, the volume of extracorporeal blood typically increases. It is typically not desired to increase the total amount of blood of a human or animal that is being treated. Therefore, subsequent reduction of blood volume is desired under such circumstances. Thus, reduction of the blood volume at any stage before re-introducing blood into the subject is typically implemented under such circumstances. Reduction of blood volume can be achieved e.g. by filtration. Thereby, it is possible to not enrich the human or animal subject with liquid, i.e. not to hyper-hydrate or not to overwater the human or animal subject. This is particularly important during long term treatment.

For option (2), liquid oxygen is preferably directly introduced into the dialysis liquid. It is conceivable that such introduction contributes to cooling of the dialysis liquid. This can be preferred for such embodiments. The oxygen can be passed through one or more fine tubes or capillaries.

For option (3), i.e. introduction of oxygen via an oxygen-permeable membrane, oxygen is typically in gaseous form. Thereby, oversaturating blood with oxygen is usually not envisaged because oxygen gas diffusion is driven by the concentration gradient.

For option (4), it is also possible to oxygenate blood by directly introducing oxygen into the blood. Oxygen is introduced either as pure oxygen, or as oxygen-comprising gas mixture, e.g. air. Such a mode of blood oxygenation is typically realized by a bubble oxygenator. It is also possible to enrich and/or (super)saturate the respective liquids with oxygen by introducing/and or generating oxygen fine bubbles (micro/nano bubbles). Such fine bubbles may be preferably generated by a porous material. Since oxygen binds to hemoglobin, $H^+$ ions are released from hemoglobin, and react with bicarbonate to form carbon dioxide. Such carbon dioxide may be removed by the step of contacting blood with the dialysis liquid via the semipermeable membrane. Direct oxygenation preferably precedes said contacting step under such circumstances. Alternatively or additionally, a bubble trap can be foreseen to remove undesired carbon dioxide gas bubbles from the oxygenated blood. However, this may be less preferred, since the bubbles, prior to their removal, can cause disturbances in the blood, such as foam formation; left-over gas bubbles, when introduced into a human or animal subject, may even cause gas embolism.

Options (3) and (6) can be realized in combination. Thus, blood or dialysis liquid can be oxygen-enriched by passing oxygen-enriched liquid across a membrane by convective transport. It is possible that the oxygen-enriched liquid is dialysate, and that the step of passing across the membrane is carried out simultaneously with the step of contacting blood and dialysis liquid by the semipermeable membrane.

Whenever oxygenation of blood via a membrane—including option (3), introduction of oxygen into blood or oxygenating blood by means of a pre-oxygenated dialysis liquid across the semipermeable membrane in step (ii) of the process of the present invention is carried out, oxygen concentration or oxygen partial pressure of the oxygen-rich fluid (e.g. dialysis liquid) being in contact with the blood via the respective membrane is preferably known. The oxygen-concentration of the dialysis liquid is preferably adjustable to a concentration from 0 and 0.42 mol/kg. To that end, it is preferably possible to increase the oxygen partial pressure. The concentration of oxygen can be determined depending on the oxygen partial pressure and on the fluid properties, e.g. temperature and salinity/ion-concentration of the fluid. At any rate, the oxygen concentration of the dialysis liquid and/or of any oxygen-enriched liquid (e.g. blood plasma) other than blood, which is brought into contact with blood in the process of the present invention, is preferably at least as high as the desired oxygen concentration of the blood plasma. Thereby, net re-diffusion of oxygen from the blood to the respective other liquid is avoided.

For all embodiments (i.e. any of (1) to (6)), introduction of oxygen is preferably realized prior to the step of contacting the dialysis liquid with blood via the semipermeable membrane, i.e. before the dialysis liquid is passed through the device for dialysis. Alternatively or additionally, introduction of oxygen is realized in parallel to the step of contacting the dialysis liquid with blood via the semipermeable membrane. In that case, introduction of oxygen across an oxygen-permeable membrane according to (3) above is most preferred. For such an embodiment, a separate (third) chamber may preferably be provided in the device for dialysis. That third chamber is separated from the second chamber (dialysis liquid chamber) and/or from the first chamber (blood chamber) by at least one semipermeable membrane. For parallel contacting, the device of the present invention preferably comprises—in addition to the first chamber for receiving blood and the second chamber for receiving dialysis liquid—a third chamber for receiving oxygen (e.g. oxygen gas, gaseous mixture comprising oxygen, oxygen-enriched liquid or oxygen dissolved in a liquid). Thereby, the third chamber and the first chamber are in contact with each other via a gas-permeable membrane.

In general, when the oxygen saturation of the blood is known, it is possible to oxygenate the blood to a desired saturation level. Oversaturation of blood with gaseous oxygen should preferably be avoided.

Preferably, the total oxygen content of the blood [ml/dl] and/or the amount of hemoglobin-bound oxygen and/or the oxygen saturation of blood, is measured, once the blood has been removed from the vein of a human or animal subject.

Blood hemoglobin concentration is usually given in gram per deciliter [g/dl]. By measuring the blood hemoglobin concentration [g/dl], the oxyhemoglobin saturation level [%] and the oxygen partial pressure [mmHg] of the blood in the extracorporeal blood circuit before a device for adding oxygen or entering the device for dialysis the total oxygen content of the blood [ml/dl] can be calculated according to the following formula:

$$cO_2 = (Hb \cdot 1.34) \cdot (O_2Hb/100) + (pO_2 \cdot 0.003)$$

Preferably, the total oxygen content of the blood [ml/dl] is measured before blood is re-introduced into the human or animal subject. Such process allows to double-check the performance of the process of the present invention and to ensure that the subject is provided with oxygenated blood.

It is also possible to measure the total oxygen content of the dialysis liquid [ml/dl] before and/or after the dialysis liquid is brought in contact with blood via the semipermeable membrane.

To facilitate a regulation which achieves the target oxygen level of the blood [ml/dl], the introduction of oxygen into the extracorporeal blood should be adjusted, i.e. preferably adjusted to the extracorporeal blood flow rate. If the oxygen is introduced into the dialysis liquid, the dialysis liquid flow rate and the amount of oxygen introduced should be adjusted, i.e. preferably adjusted to the extracorporeal blood flow rate.

As an alternative or in addition to any of the above, it is also possible to introduce oxygen into blood by any means as described in (1) to (6) above, in a step after the step of contacting blood and dialysis liquid via the semipermeable membrane. However, oxygen introduced at that stage will not come into contact with the dialysis liquid: therefore, it cannot lead to exploitation of the Haldane effect in an extracorporeal setting. Therefore, introduction of oxygen in a step preceding the step of contacting blood and dialysis liquid via the semipermeable membrane is strongly preferred. Therefore, the introduction of oxygen into blood in a step after (i.e. later than) the step of contacting blood and dialysis liquid via the semipermeable membrane, is typically not foreseen at all, or foreseen only as an additional measure, i.e. in addition to introduction foreseen in addition to in a step before the step of contacting blood and dialysis liquid via the semipermeable membrane. In that additional embodiment, oxygen is introduced in at least two sites, i.e. one preceding the step of blood/dialysis liquid contact, and one following the step of blood/dialysis liquid contact.

As described in detail below, at least one undesired substance is typically removed from blood in the step of contacting blood with the dialysis liquid via the semipermeable membrane. The presence of added oxygen in either the dialysis liquid or the blood, or both, contributes to efficient transfer of the undesired substance from the blood to the dialysis liquid, due to the Haldane effect.

The positions at which oxidation of the blood or of the dialysis liquid is possible in embodiments of the present invention are illustrated in FIG. 2. Shortly, an oxygen-enriched dialysis liquid can be prepared prior to contacting of blood via the semipermeable membrane (introduction of oxygen at position no. 10 in FIG. 2, see also Example 3), or oxygen-enriched blood can be prepared prior to contacting of dialysis liquid via the semipermeable membrane (introduction of oxygen at position no. 12 in FIG. 2). As described above, the introduction of oxygen after said contacting step is possible, but preferably not as the only site of oxygenation.

Preferably, no gas bubbles (e.g. no oxygen bubbles) are present during the step of contacting blood with the dialysis liquid via the semipermeable membrane. The molecular reason for this preference is that the exchange of membrane-permeable substances across the membrane is typically more efficient in the absence of any gas bubbles. For introducing oxygen into the dialysis liquid, it is preferable that the dialysis liquid is passed through or passed along at least one bubble trap upon said step of introducing oxygen, but preceding the step of contacting blood and dialysis liquid via the semipermeable membrane. In that case, the bubble trap is suitably localized at a position in the extracorporeal blood flow path, which is behind (after) the place where oxygen is introduced into the dialysis liquid, but ahead of (before) the device for dialysis. On the other hand, for introducing oxygen into blood, a bubble trap may be dispensable because, typically, oxygen dissolves sufficiently well or sufficiently quickly in the blood.

Alternatively or additionally, the blood is preferably passed through or passed along at least one bubble trap before the blood is reintroduced into the patient. Under such circumstances, the bubble trap is suitably localized at a site of the extracorporeal blood flow path, which follows the device for dialysis and is also localized past (after) the site where oxygen is introduced.

Preferably, in step (i) oxygen is introduced into the dialysis liquid (i.e. "indirect" oxygenation is preferred). More preferably, in step (i) oxygen is not introduced into the blood.

Accordingly, in a further aspect the present invention provides a process for oxygenating a dialysis liquid comprising a step (i) of
(i) introducing oxygen into a dialysis liquid,
wherein the dialysis liquid has a pH in the range from pH 6.8 to pH 11 and wherein the dialysis liquid comprises albumin, preferably 10 to 60 g/l albumin;
thereby generating oxygen-enriched dialysis liquid.

Various preferred options of introducing oxygen into a dialysis liquid are described above. For example, it is preferred that the oxygen is introduced into the dialysis fluid by means of liquid oxygen (as explained above, see option (2) above) or an oxygen enriched liquid (as explained above, see for example options (1) and (6) above) and/or solid (as explained above, see for example option (5) above).

Preferably, such a process for oxygenating a dialysis liquid according to the present invention further comprises a step (ii) following after step (i), wherein in step (ii) the oxygenated dialysis liquid flows through a second chamber, thereby entering, passing through and exiting the second chamber, which second chamber is separated from a first chamber by a semipermeable membrane. The semipermeable membrane, the first chamber and the second chamber and preferred embodiments thereof will be described in more detail below (in particular in the paragraphs referring to the "semipermeable membrane" and to the "device comprising a semipermeable membrane"). Preferably, the first chamber, the semipermeable membrane and the second chamber are comprised by one device, which is a dialysis unit or a dialyzer. Again, the dialyzing unit or the dialyzer and preferred embodiments thereof will be described in more detail below (in particular in the paragraphs referring to the "device comprising a semipermeable membrane"). Preferably, step (i) is performed at a site outside the device and prior to entering of the dialysis liquid into said device, so that the dialysis liquid enters into the device in oxygen-enriched form. This means in particular, that the dialysis liquid is oxygenated outside the device as described above (e.g., a dialyzer). Preferably, the dialysis fluid, which enters the device as described above (e.g., a dialyzer) is oxygenated.

As described above, also in the context of the process for oxygenating a dialysis liquid according to the present invention it is preferred that in step (i) oxygen is introduced into said dialysis liquid by any one or more of the following:
(1) infusion of an oxygen-enriched (preferably oxygen-saturated or oxygen-oversaturated) liquid (cf. option (1) described above);
(2) infusion of liquid oxygen (cf. option (2) described above);
(3) introduction of oxygen across an oxygen-permeable membrane (cf. option (3) described above);
(4) infusion of gaseous oxygen (cf. option (4) described above);
(5) introduction of oxygen-containing solids, e.g. xerogels and lyogels or frozen oxygen-enriched liquid (cf. option (5) described above); and
(6) convective transport of oxygen-enriched liquid (cf. option (6) described above).

Preferably, said dialysis liquid comprises, in addition to albumin, one or more buffering agent(s), which is/are characterized by at least one pKa value in the range from 7.0 to 11.0, as described in more detail below, and wherein said one or more buffering agent(s) is/are preferably selected from the group consisting of: Tris(hydroxymethyl)aminomethane (Tris, THAM) and carbonate/bicarbonate, as described in more detail below.

Preferably, the dialysis liquid has a buffering capacity of 12 mmol/l or more for $H^+$ ions, as described in more detail below.

It is also preferred that the dialysis liquid is characterized by a pH the range from pH 8.0 to pH 9.0, as described in more detail below.

Preferably, the dialysis liquid comprises 2,3-diphosphoglycerate (2,3-DPG), as described in more detail below. It is also preferred that the dialysis liquid comprises 10 to 40 mmol/l carbonate/bicarbonate (total amount of carbonate and bicarbonate concentration), as described in more detail below. Preferably, the dialysis liquid comprises 5 to 20 mmol/l Tris, as described in more detail below.

Preferably, in the process for oxygenating a dialysis liquid according to the present invention the dialysis liquid exiting the second chamber, is subjected to at least one treatment step (iii). If the process comprises step (ii) as described above, treatment step (iii) preferably follows after step (ii). Such a "treatment step" is described in more detail below. For example, such a "treatment step" may comprise one or more, preferably all, of the following sub-steps:
(a') separating a flow of the dialysis liquid into a first flow and a second flow;
(b') adding an acidic fluid to the first flow of dialysis liquid;
(c') removing toxins by filtrating, dialysing, precipitating or diafiltrating the acidified first flow of the dialysis liquid;
(d') adding an alkaline fluid to the second flow of the dialysis liquid;
(e') removing toxins by filtrating, dialysing, precipitating or diafiltrating the alkalized second flow of the dialysis liquid; and
(f') merging the first and the second flow of the dialysis liquid.

Exemplary embodiments illustrating such treatment steps are comprised by FIGS. 2A-2D.

Preferably, following step (iii) the dialysis liquid re-enters (is recycled to) the second chamber.

It is also preferred that at least one treatment step (iii) is selected from (1) exposure to an adsorber; (2) contact with a (preferably semipermeable) membrane, preferably for removal of carbon dioxide; and/or (3) acidic pH and/or basic pH exposure, as described in more detail below.

Preferably, said treatment step (iii) includes acidification of the dialysis liquid to acidic pH for formation of carbon dioxide and, optionally, removal of carbon dioxide.

Furthermore, it is also preferred that the process for oxygenating a dialysis liquid according to the present invention additionally comprises a step of measuring at least one parameter of the dialysis liquid, the parameter being selected from one or more of pH, carbon dioxide, partial pressure, oxygen partial pressure, bicarbonate ($HCO_3^-$) concentration, buffering capacity, deoxyhemoglobin concentration or saturation (HHb) and oxyhemoglobin saturation ($O_2Hb$), as described in more detail below. More preferably, the process for oxygenating a dialysis liquid according to the present invention additionally comprises a step of measuring at least one parameter of the dialysis liquid, the parameter being selected from one or more of pH, carbon dioxide, partial pressure, oxygen partial pressure, bicarbonate ($HCO_3^-$) concentration, buffering capacity, and deoxyhemoglobin, as described in more detail below.

Preferably, the albumin comprised by the dialysis liquid is selected from human serum albumin and/or bovine serum albumin, as described in more detail below.

It is also preferred that the dialysis liquid comprises more than 1.7 mmol/l calcium ($Ca^{2+}$) ions, preferably 2 to 4 mmol/l calcium ($Ca^{2+}$) ions, more preferably 2.4-2.6 mmol/l calcium ions, as described in more detail below.

Preferably, the pH and/or buffering capacity of the dialysis liquid is adjusted prior to re-introducing the dialysis liquid into the second chamber, as described in more detail below.

Preferably, the process for oxygenating a dialysis liquid according to the present invention further comprises the following steps:
(a) separating a flow of the dialysis liquid into a first flow and a second flow;
(b) adding an acidic fluid to the first flow of dialysis liquid;
(c) removing toxins by filtrating, dialysing, precipitating or diafiltrating the acidified first flow of the dialysis liquid;
(d) adding an alkaline fluid to the second flow of the dialysis liquid;
(e) removing toxins by filtrating, dialysing, precipitating or diafiltrating the alkalized second flow of the dialysis liquid; and
(f) merging the first and the second flow of the dialysis liquid.

Those further steps are described in more detail below, in particular in the paragraphs referring to "recycling" and "acid/base treatment". Accordingly, preferred embodiments thereof are described below, in particular in the paragraphs referring to "recycling" and "acid/base treatment". In addition, said steps (a)-(f) and preferred embodiments thereof are also described in WO 2009/071103 A1.

Preferably, steps (a)-(f) are performed before step (i). In other words, the dialysis liquid is preferably oxygenated after the treatment with the acidic and alkaline fluid.

It is also preferred that steps (a)-(f) are performed after step (ii), i.e. after the dialysis liquid passed through the dialyzer. In a preferred example, the dialysis fluid is recycled/regenerated and, thus, can pass the dialyzer multiple times (so-called multiple-pass dialysis). In this case, it is preferred that after steps (a)-(f), which are performed to recycle/regenerate the dialysis fluid, step (i) is performed, i.e. the dialysis liquid is oxygenated after recycling/regeneration. Thereafter, the recycled and oxygenated dialysis fluid passes the dialyzer (step (ii)).

As described above, steps (a)-(f) are preferably performed as substeps of a treatment step (iii), however, they may in particular also be performed independently from a treatment step (iii).

Moreover, it is also preferred that the process according to the present invention further comprises periodically switching a plurality of switching valves such that the flow of acidified dialysis liquid is alternatingly supplied to a first detoxification unit and to a second detoxification unit, whereas the flow of alkalized dialysis liquid is alternatingly supplied to the second detoxification unit and to the first detoxification unit. A detailed description and preferred embodiments thereof are provided in WO 2009/071103 A1.

It is also preferred that the process further comprises one or more of the following:
regulating the temperature of the acidified dialysate;
removing toxins by precipitation due to the acidification;
regulating the temperature of the alkalized dialysate; and
removing toxins by precipitation due to the alkalization,
for example as described below and/or in WO 2009/071103 A1.

Dialysis Liquid

The dialysis liquid of the present invention is an aqueous liquid, i.e. a liquid comprising water.

The dialysis liquid suitable for the present invention is characterized by a pH the range from pH 6.8 to pH 11.0 and by the presence of albumin. A suitable concentration of albumin is 10 to 60 g/l (i.e. 1 to 6 g/100 ml). In this specification, g/l, and g/100 ml, refers to the grams per volume (final volume of the albumin-containing liquid).

These conditions are also referred to as "framework conditions" herein. Within the framework, more specific conditions may be appropriately selected, as described below.

As defined above, the dialysis liquid is characterized by a pH the range from pH 6.8 to pH 11; and comprises albumin, preferably 10 to 60 g/l albumin. In general, albumin has the capacity to buffer aqueous liquids, and it is thought that certain amino acid residues of albumin (e.g. imidazole group of histidine, thiol group of cysteine) are important (Caironi et al., Blood Transfus., 2009; 7(4): 259-267), and at more elevated pH values, the amino groups of lysine side chains and of the N-termini may contribute to buffering. However, the buffering capacity of albumin has traditionally been exploited in blood (where it occurs naturally in the human or animal body), and the suitability of albumin-containing liquids for extracorporeal lung support has not been recognized or exploited in the art.

In the present invention, albumin is preferably serum albumin of a human or animal, such as human serum albumin, animal albumin (e.g. bovine serum albumin), or alternatively genetically engineered albumin, or mixtures of any one or more of these. Mixtures containing albumin and at least one further carrier substance are also possible. In any case, the albumin concentration specified herein refers to the total concentration of albumin, no matter if one single type of albumin (e.g. human serum albumin) or a mixture of various types of albumin is being employed. The dialysis liquid used in the present invention comprises 10 to 60 g/l albumin, preferably 10 to 40 g/l albumin, preferably 15 to 30 g/l albumin, preferably 20 to 25 g/l albumin, and most preferably 30 or about 30 g/l albumin. The concentration of albumin can also be indicated as % value; i.e. 2 g/100 ml albumin corresponds to 2% albumin (wt./vol). Albumin is a second buffering agent in the dialysis liquid according to the present invention. The albumin in the dialysis liquid contributes to its buffering capacity, and binds carbonate in the form of carbamino groups. The pH range in which albumin can suitably buffer liquids, such as blood, is well known in the art, e.g. from biochemistry textbooks. The presence of albumin in the dialysis liquid facilitates the removal of protein-bound substances from blood. In view of its property to adsorb or bind compounds such as hydrogen cations, carbon dioxide and toxins, albumin can also be more generally referred to as an adsorber, or adsorber molecule.

In addition to albumin's suitability for binding an undesired substance of the type described above, and thus its suitability in methods for extracorporeal lung support and of blood pH adjustment, the presence of albumin in the dialysis liquid, as in the present invention, further enables or enhances the removal of the protein-bound toxins. For this purpose it is possible to exploit a capacity of the albumin present in the dialysis liquid: in general, albumin is known to bind to the unbound toxins, and this property can be taken advantage of when albumin is present in the dialysis liquid, thus enabling the binding of toxins traversing the semipermeable membrane from blood into the dialysis liquid. This method is called "albumin dialysis" (see e.g. WO 2009/071103 A1, incorporated herein by reference in its entirety).

It is generally preferable that the dialysis liquid is in an oxygen-enriched state at the step of being contacted with blood. Oxygen-enrichment of a dialysis liquid can be achieved by any of the means described herein.

The dialysis liquid typically comprises water. Typically more than 50% (vol./vol.), more than more than 60% (vol./vol.), more than 70% (vol./vol.), more than 80% (vol./vol.), or more than 90% (vol./vol.), of the dialysis liquid is water. Other water-miscible liquids can also be comprised in the dialysis liquid.

The present invention not only provides a process for removing an undesired substance, but also a dialysis liquid as such, which is suitable for said purpose. Any and all specific dialysis liquid described herein is a subject of the present invention.

Buffering Agent Comprised in the Dialysis Liquid

The present inventors found that the use of a dialysis liquid (as opposed to a sweep gas as in conventional $CO_2$ removal systems) is suitable for maintaining the pH of the dialysis liquid at acceptable pH levels.

Preferably, albumin is not the only buffering agent present in the dialysis liquid. Suitably, the dialysis liquid comprises at least one additional buffering agent, wherein the buffering agent is characterized by at least one pKa value in the range from 7.0 to 11.0. The use of a buffered dialysis liquid in general, and of the specific dialysis liquid of the present invention in particular, allows to perform carbon dioxide removal in a pH range which is not detrimental to blood, while the actual capacity of the dialysis liquid for ions is much higher than it would be if the buffering agent(s) were not contained. Said at least one buffering agent(s) provides, or contributes to, the buffer capacity of the dialysis liquid.

Suitable buffering agents to be comprised in the dialysis liquid include in particular any one or more of the following: Tris(hydroxymethyl)aminomethane (Tris, THAM) and carbonate/bicarbonate.

Bicarbonate is characterized by an acidity (pKa) of 10.3 (conjugate base carbonate). Thus, in an aqueous solution containing bicarbonate, carbonate may be present as well, depending on the pH of the solution. For matters of convenience, the expression "carbonate/bicarbonate" is used herein to refer to both bicarbonate and its corresponding base carbonate. "carbonate/bicarbonate concentration" or "(combined) carbonate/bicarbonate concentration", or the like, refers herein to the total concentration of carbonate and bicarbonate. For example, "20 mM carbonate/bicarbonate" refers to a composition having a 20 mM total concentration of bicarbonate and its corresponding base carbonate. The ratio of bicarbonate to carbonate will typically be dictated by the pH of the composition.

Carbonate/bicarbonate is a suitable additional buffering agent. The carbonate/bicarbonate pair is known to provide physiological pH buffering system. Bicarbonate-containing dialysis liquids, without albumin, have been previously described in the art.

Bicarbonate and hydrogen cations, as well as other small molecules, including ions or substances which can influence the pH of an aqueous liquid, can traverse the semipermeable membrane during the process of the present invention. Therefore, in a precise sense, the (combined) carbonate/bicarbonate concentration of the dialysis liquid, as defined in this specification, is preferably defined for the dialysis liquid at the stage immediately preceding the contacting of blood, e.g. at the stage wherein the dialysis liquid enters the second chamber of a dialysis unit as described herein. A suitable total concentration of carbonate/bicarbonate (combined concentration of both substances together) is 0 to 40 mmol/l. The presence of carbonate/bicarbonate in the dialysis liquid contributes to buffering capacity of the dialysis liquid. However, the lower the concentration of carbonate/bicarbonate, the better the removal of $CO_2$ from the blood. Therefore, it can be desired to use a dialysis liquid devoid of carbonate/bicarbonate, or without addition of carbonate/bicarbonate. The pH range in which bicarbonate can suitably buffer liquids, such as blood is well known in the art, e.g. from biochemistry textbooks. When the dialysis liquid of the present invention is prepared, bicarbonate can be added in the form of any of its salts, such as sodium bicarbonate, potassium bicarbonate, and others, or alternatively be added indirectly by introducing carbon dioxide, optionally in the presence of carbonic anhydrase, and adjusting the pH as required by addition of a suitable base, such as sodium hydroxide or potassium hydroxide, sodium hydroxide being strongly preferred. In case of addition in the form of a salt, sodium bicarbonate or sodium carbonate is strongly preferred. Alternatively, potassium salts, or mixtures of sodium and potassium salts, can be used. Salts, particularly useful to be added to dialysis liquid at high pH (e.g. up to pH 11), are sodium carbonate or potassium carbonate. In general, preferred (combined) carbonate/bicarbonate concentrations in the dialysis liquid, with reference to the stage of entering the second chamber in the process of the present invention, lie in the range from more than 0 (e.g. 1) to 40 mmol/l, preferably 10 to 35 mmol/l, more preferably 15 to 30 mmol/l, and most preferably at or about 20 to 30 mmol/l. It is important to note that these are general preferred ranges and subranges. For specific purposes, such as for treating blood from a specific patient subgroup, alternative, different or partially diverging ranges may be preferable, as described below. Alternative suitable (combined) carbonate/bicarbonate concentrations lie in the range from 0 to 40 mmol/l, or more than 0 to 40 mmol/l, preferably 5 to 35 mmol/l, preferably 10 to 30 mmol/l, more preferably 15 to 25 mmol/l, and most preferably at or about 25 mmol/l. When the dialysis liquid is recycled, the (combined) carbonate/bicarbonate concentration is determined, and adjusted if required, prior to entering of the dialysis liquid into the second chamber. In general, (combined) carbonate/bicarbonate concentrations above 40 mmol/l are not desired in view of possible side effects.

Tris(hydroxymethyl)aminomethane, usually called "Tris". Tris(hydroxymethyl)aminomethane is also known as "THAM". Tris is an organic compound with the formula $(HOCH_2)_3CNH_2$. The acidity (pKa) of Tris is 8.07. Tris is non-toxic and has previously been used to treat acidosis in vivo (e.g. Kallet et al., Am. J. of Resp. and Crit. Care Med. 161: 1149-1153; Hoste et al., J. Nephrol. 18: 303-7.). In an aqueous solution comprising Tris, the corresponding base may be present as well, depending on the pH of the solution. For matters of convenience, the expression "Tris" is used herein to refer to both Tris(hydroxymethyl)aminomethane and its corresponding base, unless the context dictates otherwise. For example, "20 mM Tris" refers to a composition having a 20 mM total concentration of Tris and its corresponding base. The ratio of Tris(hydroxymethyl)aminomethane to its corresponding base will be dictated by the pH of the composition. Tris and its conjugate base, as well as other small molecules, including ions or substances which can influence the pH of an aqueous liquid, can traverse the semipermeable membrane during the process of the present invention. Therefore, in a precise sense, the Tris concentration of the dialysis liquid, as defined in this specification, is preferably defined for the dialysis liquid at the stage immediately preceding the contacting of blood, e.g. at the stage wherein the dialysis liquid enters the second chamber of a dialysis unit as described herein. Suitable Tris concentrations are in the range from 0 to 40 mmol/l, or more than 0 to 30 mmol/l, preferably 5 to 25 mmol/l, preferably 10 to 20 mmol/l, more preferably about 15 mmol/l. Alternative suitable Tris concentrations are in the range from 0-38 mmol/l, or 0-20 mmol/l.

A water-soluble protein, in addition to albumin, is suitable for the purposes of the present invention if it has at least one imidazole (histidine side) chain and/or at least one amino group (lysine) side chain or at least one sulfhydryl (cysteine) side chain. These side chains typically have pKa values in the range from 7.0 to 11.0. A protein falls under the definition water-soluble if at least 10 g/l of the protein is soluble in aqueous solution having a pH within the range of the dialysis liquid of the present invention, e.g. pH 8.0. A strongly preferred water-soluble protein in the context of the present invention is albumin, as defined in the following. Preferably, either carbonate/bicarbonate or Tris is present in addition to albumin. A preferred dialysis liquid according to the present invention comprises both (i) carbonate/bicarbonate and (ii) albumin; or both (i) Tris and (ii) albumin. Particularly, when no carbonate/bicarbonate is added to the dialysis liquid (i.e. the carbonate/bicarbonate concentration in the dialysis liquid is 0 mmol/l or near 0 mmol/l), then it is preferable that both Tris and albumin are present in the dialysis liquid. Alternatively, Tris is the only buffering agent comprised in the dialysis liquid.

All the above ranges and concentrations of Tris, carbonate/bicarbonate and albumin are combinable in the present invention. A preferred dialysis liquid according to the present invention comprises both (i) carbonate/bicarbonate and (ii) albumin; or both (i) Tris and (ii) albumin. An alternative preferred dialysis liquid comprises Tris as the only buffering agent, i.e. does not contain added carbonate/bicarbonate or albumin.

The present invention is advantageous compared to previous uses of carbonate-containing dialysis liquids, inter alia because the buffering capacity albumin can be taken advantage of.

A first particular dialysis liquid useful in the present invention comprises 0 to 40 mmol/l carbonate/bicarbonate (preferably 10 to 40 mmol/l carbonate/bicarbonate), 10 to 60 g/l albumin (i.e. 1 to 6 g/100 ml albumin), and has a pH the range from pH 7.75 to pH 11.0, preferably pH 8.0 to pH 10.0, and more preferably pH 8.0 to pH 9.0. Preferred carbonate/bicarbonate concentrations are as specified above.

A second particular dialysis liquid useful in the present invention comprises 0 to 40 mmol/l Tris (preferably 1 to 20 mmol/l Tris), 10 to 60 g/l albumin (i.e. 1 to 6 g/100 ml albumin), and has a pH the range from pH 7.75 to pH 11.0, preferably pH 8.0 to pH 10.0, and more preferably pH 8.0 to pH 9.0. Preferred Tris concentrations are as specified above.

Optionally, other inorganic or organic buffering agents are present. Preferably, such buffering agents have at least one pKa value in the range from 7.0 to 9.0. More preferably, two or three of such buffering agents may be employed, each having a pKa value in the range of 7.0 to 9.0. Suitable additional organic buffering agents include proteins, particularly water-soluble proteins, or amino acids, or Tris; and suitable additional inorganic buffering molecules include $HPO_4^{2-}/H_2PO_4^-$.

Buffering Capacity for $H^+$ Ions

Suitably, the dialysis liquid used in the present invention has a high buffering capacity for $H^+$ ions, e.g. a buffering capacity for $H^+$ ions which is 12 mmol/l $H^+$ ions or more. A buffering capacity for $H^+$ ions which is 12 mmol/l $H^+$ ions or more is typically a buffering capacity which exceeds the buffering of blood plasma (pH 7.45; see Example 1). Thus, in the present invention, the buffering capacity of the dialysis liquid typically exceeds the buffering of blood plasma (pH 7.45). In other words, the buffering capacity of the dialysis liquid is typically a buffering capacity for 12 mmol/l or more $H^+$ ions.

In the context of the present invention, the term "buffering capacity for $H^+$ ions" or simply "buffering capacity" is an abstract value expressing the capacity of a given liquid to buffer the addition of $H^+$ ions. The term "buffering capacity for $H^+$ ions" is an inherent property of a respective liquid (aqueous solution). Also blood plasma is such a liquid. The determination of buffering capacity of blood plasma requires a step of centrifugation; the centrifugation results in pelleting of blood cells including platelets, and the supernatant is termed plasma. Such centrifugation is described in example 1. Suitable conditions for centrifugation of blood, and thus for the preparation of blood plasma are known in the art.

Precisely, the term "buffering capacity for $H^+$ ions" refers to the capacity to buffer a certain amount of $H^+$ ions, without reaching a pH lower than 6.5. "Without reaching a pH lower than 6.5" means that the pH of a properly mixed liquid does not reach a value of lower than pH 6.5. Thus, adequate mixing is important in practical assessment of the buffering capacity. Thus, as used herein, in the context of the dialysis liquid of the present invention, the term "buffering capacity for $H^+$ ions" can be used solely for liquids having a pH of 6.5 or more. As defined herein, a solution having a pH of 6.5 would have a buffering capacity for $H^+$ ions of zero mmol/l (0 mmol/l). The dialysis liquids of the present invention typically have a pH higher than 6.5, i.e. as defined herein; and therefore, they do have a buffering capacity for $H^+$ ions. Preferably the buffering capacity is 12 mmol/l $H^+$ ions or more. Even more preferred are buffering capacities higher than that, i.e. buffering capacities for $H^+$ ions of 12 mmol/l or more, 14 mmol/l or more, 16 mmol/l or more, 18 mmol/l or more, 20 mmol/l or more, 22 mmol/l or more, 24 mmol/l or more, 26 mmol/l or more, 28 mmol/l or more, 30 mmol/l or more, 32 mmol/l or more, 34 mmol/l or more, 36 mmol/l or more, 38 mmol/l or more, 40 mmol/l or more, 42 mmol/l or more, 44 mmol/l or more, 46 mmol/l or more, 48 mmol/l or more, 50 mmol/l or more. Thus, the dialysis liquid according to the present invention typically has a buffering capacity for $H^+$ ions of 12 or more mmol/l, such as more than 12 mmol/l. Preferred buffering capacities lie in the range from 12 to 50 mmol/l, more than 12 to 40 mmol/l, 13 to 30 mmol/l, 14 to 25 mmol/l, 15 to 24 mmol/l, 16 to 23 mmol/l, 17 to 22 mmol/l, 18 to 21 mmol/l, 19 to 20 mmol/l.

The buffering capacity is not solely dependent on the pH of the respective liquid, but influenced by the composition of the liquid (presence and concentration of buffering compounds in the said liquid).

Buffering capacity for H⁺ ions is indicated as a number value, with the unit "mmol/l". According to the present invention, the buffering capacity for H⁺ ions (buffering capacity in mmol/l) is determined by the following four-step assay:

1. As an introductory comment, the assay is suitable for determining the buffering capacity for H⁺ ions of a given liquid (dialysis liquid or candidate dialysis liquid) that has a pH in the pH range of the dialysis liquids of the present invention, i.e. pH 6.8 to pH 11.0, or subrange thereof. Thus, in a first step, it is tested whether the given liquid has a pH within that range. If that is not the case, the given liquid is not a dialysis liquid according to the present invention (no further testing necessary). If that is, however, the case, then the buffering capacity of the given liquid is determined by means of the following steps 2 and 3:
2. The liquid is subjected to titration with HCl. In particular, 0.1 M HCl is added, the solutions are agitated to ensure mixing, the pH is continuously monitored, and titration is terminated exactly when the pH of the liquid subject to titration reaches a final value of pH 6.5. In other words, titration is stopped when the pH reaches a value of 6.5. Based on the amount of HCl added until pH 6.5 is reached, the buffering capacity (H⁺ ion in mmol/l) is calculated. This is possible because HCl is a strong acid which, according to the common general knowledge, dissolves completely in aqueous solution. Thus, 0.1 M HCl (0.1 mol/l) contains 0.1 mol/l dissolved Cl⁻ ions and 0.1 mol/l dissolved H⁺ ions. Based on the volume of HCl required for a given liquid to reach a pH of 6.5 upon titration, the amount of H⁺ ions can be calculated that is buffered by said volume of dialysis liquid. If the amount of the given liquid used in the assay is 1 liter, the amount of H⁺ ions that is buffered by 1 l dialysis liquid (buffering capacity in mmol/l) is directly obtained. If the amount of the given liquid used in the assay is a defined amount which is more than 1 liter or less than 1 liter, the amount of H⁺ ions that can be buffered by 1 l dialysis liquid (buffering capacity in mmol/l) is obtainable by simple mathematical calculation.
3. The buffering capacity as determined in step 2 (mmol/l) is compared to a reference value. Suitable reference values are 10 mmol/l; 11 mmol/l, 12 mmol/l, 13 mmol/l, 14 mmol/l; whereby 12 mmol/l is strongly preferred. Alternatively, the reference value is represented by the buffering capacity of human or animal (pork, mouse) blood; in that case, the buffering capacity of blood plasma is determined as described in above step 2.
4. If the buffering capacity of the given solution (mmol/l) exceeds the reference value (mmol/l), the given solution is determined to have a buffering capacity according to the present invention.

In the assay for determining buffering capacity, all pH measurements, as well as the titration, is performed at room temperature (temperature of all solutions and equipment; surrounding temperature). The above assay is straightforward and can be performed by the skilled person with minimal effort, based on the guidance herein and on the common general knowledge. Thereby, the buffering capacity of a given liquid can be readily and reliably determined without undue burden.

An example of determination of buffering capacity, as defined in the present invention, is given below in Example 1. As shown by that example, blood plasma having pH 7.45 typically has a buffering capacity of 12 mmol/l.

However, it is conceivable that blood plasma from other sources (other species and/or other individuals) has a different buffering capacity. Other conceivable blood plasma buffering capacities lie in the range of 3 to 30 mmol/l, preferably 4 to 25 mmol/l, preferably 5 to 20 mmol/l, preferably 6 to 19 mmol/l, preferably 7 to 18 mmol/l, preferably 8 to 17 mmol/l, preferably 9 to 16 mmol/l, preferably 10 to 15 mmol/l, preferably 11 to 14 mmol/l, preferably 12 to 13 mmol/l.

It is preferable that the dialysis liquid according to the present invention typically has a buffering capacity which exceeds the buffering capacity of blood plasma. When blood of an individual, e.g. a patient, is treated in the process or method of the present invention, then the buffering capacity for H⁺ ions is preferably selected such that it exceeds the buffering capacity of blood of that individual, e.g. that patient.

pH of the Dialysis Liquid

Preferred pH ranges of the dialysis liquid include pH 8.0 to pH 10.5, pH 8.0 to pH 10.0, pH 8.0 to pH 9.5, and preferably pH 8.0 to pH 9.0. At such ph values it is possible to remove H⁺ (protons) without destabilizing the albumin comprised by the dialysis liquid.

Thus, the at least one pKa value of the at least one buffering agent present in the dialysis liquid is in the range from pH 7.0 to pH 11.0; pH 8.0 to 10.5, 8.0 to 10.0, 8.0 to 9.5, and preferably 8.0 to 9.0. If more than one buffering agent is present, it is preferably that each of them has a pKa value in the above range or subrange. If the at least one buffering agent has more than one pKa value, at least one said pKa value, preferably more than one said pKa values, lie(s) is in the above range or subrange. Any buffering agent having at least one pKa value in the range from 7.0 to 11.0 is theoretically suitable for buffering in the desired pH range. However, in the context of the present invention, the buffering agent must be selected such that it is not toxic or does not cause undesired side effects in the human or animal being that is subject to dialysis. Particularly suitable buffering agents are the carbonate/bicarbonate system, Tris, and water-soluble proteins (preferably albumin), all as defined herein above. Another suitable pH value of the dialysis liquid is the range from pH 7.75 to pH 9.0. In general, preferred pH values lie in the range from pH 7.75 to pH 9.0, preferably from pH 8.0 to pH 9.0, preferably from pH 8.1 to pH 8.9, preferably from pH 8.2 to pH 8.8, preferably from pH 8.3 to pH 8.7, more preferably from pH 8.4 to pH 8.6, and most preferably at or around pH 8.5. It is important to note that these are general preferred ranges and subranges. For specific purposes, such as for treating blood from a specific patient subgroup, alternative, different or partially diverging ranges may be preferable, as described below. The pH can be adjusted by the amount or concentration of buffering substances, such as bicarbonate and hemoglobin, within the ranges contemplated herein, and/or adjusted by addition of an acid or base, such as hydrochloric acid or sodium hydroxide.

Bicarbonate and hydrogen cations, as well as other small molecules, including ions or substances which can influence the pH of an aqueous liquid, can traverse the semipermeable membrane during the process of the present invention. Therefore, the pH of the dialysis liquid does not necessarily remain constant throughout the process step of contacting blood with the dialysis liquid. Therefore, in a precise sense, the pH of the dialysis liquid, as defined in this specification, is preferably defined for the dialysis liquid at the stage immediately preceding the contacting of blood, e.g. at the stage wherein the dialysis liquid enters the second chamber of a dialysis unit as described herein.

It is not necessary to maintain the dialysis liquid at the pH desired upon beginning of exposure to blood (entry into the second chamber) at all times. Particularly when the dialysis liquid is being recycled, as described below, pH and (combined) carbonate/bicarbonate concentration may vary over time. However, at the stage of entering into the second chamber, the dialysis liquid is adjusted to comply with the specified pH and bicarbonate/albumin concentrations. For example, the pH can be measured by at least one pH measuring device before the dialysis liquid enters the second chamber. Optionally, the pH can additionally be measured by at least one pH measuring device.

Further Constituents of the Dialysis Liquid

In general, and in addition to the aspects described above, a dialysis liquid suitable for the physiological purposes of the present invention preferably comprises the desired electrolytes, nutrients and buffers in adequate concentrations, so that their levels in the patient's blood can be adjusted, e.g. brought to normal physiological values, or to any otherwise desired or indicated values. Optional constituents of the dialysis liquid according to the present invention include electrolytes, preferably selected from sugars and/or salts (anions/cations/zwitterions). Typical cations include calcium, magnesium, potassium and sodium ions; typical anions include chloride, $HCO_3^-$, $H_2CO_3$, $HPO_4^{2-}$, $H_2PO_4^-$; typical zwitterions include amino acids (e.g. histidine) and peptides or salts of organic acids.

Preferably, the dialysis liquid contains no added acetic acid and no added acetate. Preferably, the combined concentration of acetic acid in the dialysis liquid is less than 4 mmol/l, less than 3 mmol/l, less than 2 mmol/l, less than 1 mmol/l, most preferably 0 mmol/l.

The dialysis liquid can also comprise other membrane-permeable small molecules for transfer to blood, if desired, e.g. glucose.

It is also generally preferable that the dialysis liquid has low or negligible contents of dissolved carbon dioxide and nitrogen.

Preferably, the dialysis liquid comprises calcium ($Ca^{2+}$) ions. In contrast to prior art dialysis liquid, which contains only free calcium ions, the dialysis liquid of the present invention is typically characterized in that the calcium ions are at least partially bound to albumin. In general, at higher pH values, more calcium is bound to albumin, and less is available for exchange with the blood. Therefore the total calcium in the albumin-containing dialysis liquid according to the present invention contains higher calcium concentrations that known from dialysis liquids according to the state of the art. In particular, the calcium ion concentration of albumin-containing dialysis liquid is 1.7 mmol/l or higher. This is desired in order to have enough free calcium available, i.e. to not decrease the free calcium ion concentration in the blood (see Example 2).

Preferably the dialysis liquid comprises 2 to 4 mmol/l calcium ($Ca^{2+}$) ions, more preferably 2.4-2.6 mmol/l calcium ions. Calcium ions can be added in the form of any suitable salt, e.g. calcium chloride. Addition of calcium into the dialysis liquid is beneficial because blood also comprises calcium; the presence of calcium in the dialysis liquid prevents undesired net flux (leaking) of calcium ions from the blood into the dialysis liquid. It is known that calcium ions can precipitate at very basic pH. The presence of calcium is not incompatible with the present invention in view of the maximum pH value of 9.0 of the dialysis liquid when being brought into contact with blood via the semi-permeable membrane. Whenever the dialysis liquid has a pH higher than 10, some ions such as calcium ions (and others) become usually insoluble. Therefore, if the dialysis liquid has a pH of more than 9, it is preferable that no calcium ions (and other insoluble ions) are present. In order not to deplete a patient of such ions, they should be infused directly into the blood of the patient, if the dialysis liquid has a pH of that range.

Preferably, the dialysis liquid is characterized by an osmolarity which is substantially identical to the osmolarity of blood being dialyzed.

In addition to the above, the enzyme carbonic anhydrase may be added to the dialysis liquid, or may be present in the dialysis liquid. Carbonic anhydrases are enzymes which promote the reversible reaction from carbon dioxide to bicarbonate ($HCO_3^-$) and $H^+$ ions. Carbonic anhydrases can be added to the extracorporeal blood circuit. It is also possible to coat the inside surface of the first or second chamber with carbonic anhydrases.

Optionally, the dialysis liquid comprises 2,3-diphosphoglycerate (2,3-DPG or also known as 2,3-bisphosphoglyceric acid, 2,3-BPG). 2,3-DPG is known to interact with deoxygenated hemoglobin beta subunits by decreasing their affinity for oxygen, so it allosterically promotes the release of the remaining oxygen molecules bound to the hemoglobin, thus enhancing the ability of RBCs to release oxygen near tissues that need it most. 2,3-DPG is thus an allosteric effector. The concentration of 2,3-DPG in the erythrocytes is usually about 4-5 mmol/l. In the dialysis liquid of the present invention, the concentration of 2,3-DPG can be 0 to 4 mmol/l; 4 to 5 mmol/l, or more than 5 mmol/l, depending on the purpose. One reason why 2,3-DPG may be added to dialysis liquid is to avoid a net loss of 2,3-DPG from blood, i.e. to prevent that 2,3-DPG diffuses from the blood into the dialysis liquid. The treatment of acidosis patients typically requires addition of 2,3-DPG.

Undesired Substance(s) Comprised in the Blood: Removal of the Undesired Substance(s)

The process of the present invention allows for removal of at least one undesired substance from blood. In the broadest sense, the at least one undesired substance to be removed is a substance resulting from metabolic activity. Preferably, the at least one undesired substance is selected from the group consisting of carbon dioxide ($CO_2$), hydrogen cation ($H^+$), hydrogen carbonate ($HCO_3^-$), carbonic acid ($H_2CO_3$), and solvates of any one thereof, and any combinations of these. It is known that, in aqueous environment (e.g. aqueous solution or aqueous suspension, such as e.g. blood or dialysis liquid), these undesired substances relate to each other as expressed by the following equilibrium equation:

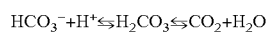
$$HCO_3^- + H^+ \leftrightarrows H_2CO_3 \leftrightarrows CO_2 + H_2O$$

The reactants (educts and products) of this reaction are present in dynamic equilibrium—as qualitatively indicated by the arrows ($\leftrightarrows$) in the above equation. The dissociation of carbonic acid ($H_2CO_3 \leftrightarrows CO_2 + H_2O$) is typically catalyzed or aided by the enzyme carboanhydrase which is present in erythrocytes. In accordance with the general principles of a dynamic equilibrium, the removal of one reactant causes, by Le Chatelier's principle, a shift of the reaction. $ECCO_2R$ systems of the prior art rely on the use of a gas exchange membrane, across which one reactant, carbon dioxide, diffuses from the extracorporeal blood into a gas chamber. In contrast, the present invention enables the removal of at least one undesired substance from one liquid (blood) directly into another liquid (dialysis liquid). Therefore, the present invention is not limited to the removal of gaseous undesired substances (such as $CO_2$), and does not require the transfer of undesired substances to the gas phase. It is thus contemplated that carbon dioxide is not transferred to the gas phase in the process of the present invention.

In general, one of the forms in which $CO_2$ is transported in the blood is in the form of carbamino groups, wherein carbon dioxide is attached to the terminal amine groups of proteins in the blood, primarily hemoglobin (then termed carbaminohemoglobin). In general, it is understood that the formation of carbamino groups is rapid and reversible and does not require catalysis by any enzyme. Thus, carbon dioxide in the carbamino form is also rapidly released from the amino group of blood proteins such as hemoglobin when the carbon dioxide concentration decreases in its surrounding as a result of diffusion into the dialysis liquid, so that, in accordance with Le Chatelier's principle, a new equilibrium is established. As described above, carbaminohemoglobin and dissolved carbon dioxide are also in equilibrium with the bicarbonate ($HCO_3^-$)/$H^+$ ion pair, but rapid conversion via $H_2CO_3$ requires the enzyme carbonic anhydrase. Carbonic anhydrase is naturally present in erythrocytes.

Therefore, in the present invention, all three major forms of carbonate present in blood, (i) protein (hemoglobin)-bound $CO_2$ in the form of carbaminohemoglobin, (ii) free $CO_2$, and (iii) bicarbonate ($HCO_3^-$)/$H^+$, can be removed, directly or indirectly, across the semipermeable membrane. While free $CO_2$ and bicarbonate ions can cross the semipermeable membrane along the concentration gradient into the dialysis liquid, hemoglobin-bound $CO_2$ becomes preferentially released from hemoglobin when e.g. the concentration of free $CO_2$ decreases as a result of diffusion into the dialysis liquid, so that, in accordance with Le Chatelier's principle, a new equilibrium of the three major forms of carbonate present in blood (transportation forms) is established. Importantly, in the present invention the different transportation forms of carbon dioxide do not have to be transferred to the gas phase to be removed. Thus, blood-gas contact is not required, and preferably not foreseen. The present invention enables removing all major transportation forms of carbon dioxide from the blood completely in a liquid medium. Depending on the bicarbonate ($HCO_3^-$) concentration of the dialysis liquid and of the blood, bicarbonate can be removed from the blood along the concentration gradient of the dialysis liquid on the one side and blood on the other side of the semipermeable membrane.

In the context of the present invention, these undesired substances can be removed directly by transfer to the dialysis liquid along the concentration gradient (direct removal). Alternatively or additionally, the undesired substances can be removed indirectly by reaction with substances transferred from the dialysis liquid to the blood, which also results in a net removal of the undesired substance from the blood (indirect removal): for example, hydrogen cations can be indirectly removed from the blood by transferring $OH^-$ ions from the dialysis liquid to the blood, which is achieved because the pH of the dialysis liquid used in the present invention is typically more alkaline than the pH of the blood to be treated. Also other undesired substances, such as carbonic acid, carbonate, hydrogen carbonate, can be removed indirectly by transferring substances from the dialysis liquid to the blood, and their influence on the bicarbonate equilibrium.

In contrast to prior art systems which remove carbon dioxide in the gas phase, the present invention enables the removal of substances which are soluble in liquids. These substances include ions of any type, as long as they are soluble in water, and hydrogen cations and bicarbonate anions in particular. The present invention therefore allows for more complete, and thus more efficient, removal of metabolites from the blood than the $ECCO_2R$ methods of the state of the art. The mechanism of carbon dioxide removal according to the present invention allows that the dissolved gas diffuses from one liquid phase to another liquid phase.

A dialysis unit or device comprising two chambers, as described in detail below, can suitably be used in the process of the present invention. The first chamber is suitable for receiving the blood. The first chamber suitably has an inlet (for entering blood) and an outlet (for exiting blood).

It is desired that the blood, when a dialysis unit used in the process of the present invention, exits the first chamber (outlet) when its pH lies in the range of pH 7.35 to 7.45, preferably 7.36 to 7.44, more preferably 7.37 to 7.43, more preferably 7.38 to 7.42, more preferably 7.39 to 7.41, and most preferably about 7.40.

Preferably, the blood is returned into the human or animal body after exiting the first chamber (outlet). Suitable tubing and connections are known in the art and can be employed in the context of the present invention.

Optionally, it is foreseen to remove bubbles (if any), from the blood, i.e. at a stage after exit from the first chamber (outlet), and prior to reintroduction of the blood into the human or animal body. For this purpose, one or at least one bubble trap can be placed behind the first chamber. This is particularly suitable if blood is also exposed to a gas or to a gas-saturated or gas-supersaturated liquid, during at least part of the process.

Aspects of Removal of Carbon Dioxide from Blood

Carbon dioxide removal is indicated not only as a substitution of lung support, but also to maintain the blood essentially bubble-free. In theory, introduction of dissolved oxygen into blood, but without carbon dioxide removal, would increase the likelihood of formation of carbon dioxide gas bubbles and/or an increased concentration of dissolved carbon dioxide in the blood and/or a decrease in the blood pH. In the process of the present invention, carbon dioxide removal is foreseen together with oxygenation; thereby, such undesired side effects are avoided.

An increase in the $pCO_2$ decreases the oxygen affinity of hemoglobin so a carbon dioxide removal from the blood as it is possible in the invented dialysis circuit increases the oxygen affinity of hemoglobin. But the effects of a $pCO_2$ change are not that big as a $pCO_2$ change of 40 mmHg just shifts the $P_{50}$ by about 10 mmHg $pO_2$. A far greater impact has a $H^+$ ion change which is reflected in a pH change. A pH increase in the blood results in an increase of the total binding capacity of hemoglobin to oxygen. An increased blood pH is achieved in the present invention by introducing $OH^-$-ions into the dialysis liquid or into the blood.

Aspects of Removal of Hydrogen Cations from Blood

Owing to the pH and buffering capacity of the dialysis liquid, $H^+$ ions can be removed from blood during the step of contacting. Owing to removal of free $H^+$ ions from blood, further $H^+$ ions will dissociate from hemoglobin, and will also be removed. Further, owing to the Haldane effect, which is exploited in the step of contacting blood and dialysis liquid via the semipermeable membrane, the removal of the hemoglobin-bound $H^+$ ions leads to an increased affinity for binding oxygen to the hemoglobin.

To that end, the introduction of oxygen enriched liquid into blood and/or into the dialysis liquid at step prior to—or concurrent with—the contacting step is advantageous. The presence of oxygen improves the release of the hemoglobin-bound $H^+$ ions, which facilitates their removal from the blood. The ratio of oxyhemoglobin ($O_2Hb$) and the $H^+$ bound deoxyhemoglobin (HHb) is not only related to the concentration of oxygen or $H^+$ ions but also depends on the pH. Accordingly an introduced pH shift of the blood can influence $H^+$ ion binding to hemoglobin. The pH of the blood can in turn be influenced at the step of contacting blood with the dialysis liquid; this is suitably achieved by adjusting the pH and buffering capacity of the dialysis liquid, within the framework of the present invention.

Adaptation of the Dialysis Liquid with the Goal of Adjusting Blood to a Certain pH Besides the function in extracorporeal lung support, including removal of $CO_2$ and/or bicarbonate ions from the blood, and oxygenation of the blood, the process of the present invention also allows for adjusting the pH of the blood to a desired level. This is suitable e.g. for the treatment of acidic blood, e.g. blood from acidosis patients. It is desired that the blood pH is adjusted to a predetermined value or a predetermined range within the range of pH 6.8 to pH 8.5. Blood pH values outside that range are not desired in view of undesired side effects, such as denaturation of blood proteins and/or precipitation of blood components. In general, adjusting the blood pH value or range means that the blood is characterized by said adjusted value or range at the stage of exit from the first chamber.

Given that physiological blood of a healthy human subject typically has a pH in the range of 7.35 to 7.45, i.e. around 7.40, it is in some embodiments desired to adjust the blood pH to a range or value encompassing that range, i.e. 7 to 8.5 7.0 to 7.8, 7.2 to 7.6, or 7.3 to 7.5. In preferred embodiments, when it is intended to bring the blood pH to a value near the value of physiological blood of a healthy human subject, it is desired to adjust the blood pH to a value or range within the range of pH 7.35 to 7.45, preferably 7.36 to 7.44, more preferably 7.37 to 7.43, more preferably 7.38 to 7.42, more preferably 7.39 to 7.41, and most preferably about 7.40.

As described in detail below, the present invention is also particularly suitable for treating subjects suffering from acidosis (acidosis patients), i.e. subjects suffering from metabolic and/or respiratory acidosis. In embodiments of the present invention directed at, or suitable for, treating blood from acidosis patients, it can be desired to adjust the blood pH to a range or value that is more alkaline than 7.40, more than 7.40 to 8.0, 7.5 to 7.9, or 7.6 to 7.8, preferably within the range of pH 7.65 to 7.75, e.g. 7.7.

Adjustment of the blood pH in the method of the present invention is technically feasible because of the buffering capacity of the dialysis liquid used, and because of the permeability of the semipermeable membrane of $H^+$ and $OH^-$ ions. Thus, by using a buffered dialysis liquid, pH adjustment of the blood can be achieved. $H^+$ and $OH^-$ ions can cross the semipermeable membrane, and will do so along the respective concentration gradient.

Without wishing to be bound by any particular theory, it is understood that $H^+$ ions are eliminated from the blood mainly in view of the excellent buffering capacity of the dialysis liquid of the present invention. In addition to that, it is thought that minor amounts of $H^+$ ions are removed by reacting with $OH^-$ ions, which are provided by the dialysis liquid, on either side or on both sides of the semipermeable membrane. The elimination of not only carbon dioxide from the blood, but also $H^+$ ions (by reaction with $OH^-$ ions) from the blood, enables to adjust the acid-base balance of the blood. The dialysis liquid used in the present invention can be adjusted based on the needs, e.g. based on the needs of a patient being subjected to treatment by dialysis. The present invention thus allows for preferential removal of carbon dioxide, or for preferential adjustment of the blood pH, or both. This versatility is provided by the possibilities to adjust the pH of the dialysis liquid and to adjust the concentration of buffering substances (particularly albumin and bicarbonate) in the dialysis liquid, each independently from each other, within the general ranges as defined herein.

Adaptation of the Dialysis Liquid with the Goal of Oxygenating Blood to a Certain Value Since the oxygen affinity of hemoglobin is dependent on temperature, $pCO_2$, pH and the concentration of 2,3-diphosphoglycerate (2,3-DPG or also known as 2,3-bisphosphoglyceric acid, 2,3-BPG), any one or more of these parameters can be modified to achieve a desired degree of oxygenation according to the present invention. Each of these four parameters can be adjusted independently. This also enables to foster the oxygen uptake or delivery which can be necessary for subjects in intensive care units (ICU). For example, at standard blood conditions (pH 7.4, 37° C., 2,3-DPG 13 µmol/g Hb, $pCO_2$ 40 mmHg), the $P_{50}$ (meaning 50% hemoglobin saturation) is achieved at a $pO_2$ of 27 mmHg.

The temperature of the blood, as it passes through the first chamber, is not particularly limited, as long as the blood constituents are not denatured and the blood remains liquid. A suitable temperature lies in the range of 1.2° C. to 45° C., e.g. 37° C. Preferably, the blood temperature is decreased. This can be achieved preferably by cooling the dialysis liquid in the device for dialysis, and/or by another external and/or internal cooling unit in the extracorporeal blood circuit and/or by introduction a solution with a temperature from 1.2 to less than 37° C. into the extracorporeal blood circuit. It is known that a temperature shift of the blood by 20° C. (20 Kelvin) can change the $P_{50}$ by 30 mmHg $pO_2$.

At higher temperatures (e.g. 37° C.), the oxygen affinity of hemoglobin is relatively low. In general, a temperature shift of the blood by 20° C. can change the $P_{50}$ by 30 mmHg $pO_2$. To achieve an increased oxygen affinity of hemoglobin, at the extracorporeal step of introducing oxygen according to the present invention, the blood temperature can be decreased, either directly, or indirectly. In a preferred embodiment, the process of the present invention is carried out such that at least part of the process is performed at a temperature of less than 37° C., preferably 4° C. to 20° C. Indirect decrease of the temperature can be achieved e.g. by decreasing the temperature of the dialysis liquid, or by an external and/or internal cooling unit in the extracorporeal blood circuit and/or by introduction a solution with a temperature from 1.2 to less than 37° C. into the blood or into the dialysis liquid. Suitably, the blood temperature at the step of being in contact with the dialysis liquid via the semipermeable membrane is from 1.2 to 37° C., such as from 5 to 35° C., from 10 to 30° C., from 15 to 25° C., or about 17° C. or about 20° C. Preferably, the cooling is carried out as follows:

(a) step (i) is characterized in that oxygen-enriched liquid having less than 37° C., or liquid oxygen, is infused into blood; and (b) step (ii) is characterized in that the dialysis liquid being contacted with blood has a temperature of less than 30° C., e.g less than 28° C., preferably less than 26° C., less than 24° C., less than 22° C., or less than 20° C.

In the present invention, 2,3-DPG may be comprised at a concentration equal or higher to the concentration in blood of the subject being treated. Thereby, the oxygen affinity of hemoglobin can be adjusted. Alternatively, the dialysis liquid according to the present invention comprises a 2,3-DPG concentration lower than that, i.e. lower than blood.

Thereby, 2,3-DPG can be removed from the blood, which leads to a left shift of the oxygen dissociation curve and lowers the $P_{50}$ to a $pO_2$ of 18 mmHg.

In view of the general versatility of the dialysis liquid employed in the present invention, i.e. the suitability for adjusting the blood pH as well as the suitability for lung support, as well as combinations thereof, the dialysis liquid may be chosen to specifically or primarily address a particular goal. For example, the dialysis liquid may be chosen to the goal of adjusting the blood pH, or to the goal of providing a lung support. In this context, the terms design and adaptation of the dialysis liquid are used interchangeably and refer to the dialysis liquid immediately prior to exposure to blood via the semipermeable membrane, i.e. at the stage of entering the second chamber.

For example, when the subject being treated suffers not only from low blood oxygenation, but also from respiratory acidosis, then it will typically be desired to adjust the blood pH, which can be achieved in the present invention by removing carbon dioxide, directly or indirectly. This further increases the oxygen binding of haemoglobin, by virtue of the Haldane effect. The dialysis liquid used in the present invention can be adapted to such purposes, within the general framework of the dialysis liquid as described herein.

Depending on the bicarbonate ($HCO_3^-$) concentration of the dialysis liquid and of the blood, bicarbonate can be removed from the blood along the concentration gradient of the dialysis liquid on the one side and blood on the other side of the semipermeable membrane. In other words, as long as the (combined) carbonate/bicarbonate concentration in the dialysis liquid is lower than the (combined) carbonate/bicarbonate concentration in the blood, bicarbonate will be removed from the blood into the dialysis liquid along the concentration gradient. If removal of bicarbonate from the blood is not desired or not indicated, the (combined) carbonate/bicarbonate concentration of the dialysis liquid is selected such that it is not lower than the (combined) carbonate/bicarbonate concentration of the blood. "not lower", in this context, means equal or higher, such as slightly higher, but typically means roughly equal or equal.

Generally speaking, a dialysis liquid adjusted for treating blood from a subject suffering from respiratory acidosis comprises bicarbonate preferably in the concentration range from 0 to 40 mmol/l, or alternatively 5 to 40 mmol/l or 10 to 40 mmol/l. Preferred embodiments of the (combined) carbonate/bicarbonate concentration for such purposes include the range from 15 to 35 mmol/l, from 20 to 30 mmol/l, or (about) 25 mmol/l.

Semipermeable Membrane

In the present invention, the transfer of the at least one undesired substance from the blood to the dialysis liquid occurs across a semipermeable membrane. The membrane separating blood from dialysis liquid in the contacting step of the process of the present invention is suitable to be permeable to oxygen, carbon dioxide and liquids. The membrane forms a separation surface or contacting surface, across which the transfer of compounds is possible. The membrane is permeable to liquids, particularly water and aqueous solutions. The membrane is ideally permeable to oxygen, carbon dioxide, bicarbonate, $H^+$ ions and liquids. In a device comprising a first chamber for receiving blood and a second chamber for receiving dialysis liquid, the semipermeable membrane is located such that it separates the first chamber and the second chamber. This enables the transfer of membrane-permeable substances across from the first chamber to the second chamber or from the second chamber to the first chamber. Typically, such substances, as long as they are membrane permeable, will preferentially migrate along their concentration gradient.

The semipermeable membrane is not permeable for proteins of the size or properties of albumin. However, bicarbonate and hydrogen cations, as well as other small molecules, including ions or substances which can influence the pH of an aqueous liquid, can traverse the semipermeable membrane during the process of the present invention. Therefore, the pH of the dialysis liquid does not necessarily remain constant throughout the process step of contacting blood with the dialysis liquid. Therefore, in a precise sense, the pH and the (combined) carbonate/bicarbonate concentration of the dialysis liquid, as defined in this specification, are preferably defined for the dialysis liquid at the stage immediately preceding said contacting, i.e. the stage wherein the dialysis liquid enters the second chamber. In other words, the dialysis liquid, when entering the second chamber, has a pH the range from pH 6.8 to pH 11.0 (or any preferred value or subrange thereof, as defined in this specification).

While the transfer of substances across the semipermeable membrane is passive, i.e. along the concentration gradient, the blood/and/or the dialysis liquid are preferentially moved, e.g. by a constant flow of these liquids through the respective chamber, and optionally by stirring, shaking, pressure gradient (causing convection) or other suitable mechanical activity. Such mechanical activity is believed to contribute to efficient exposure of the substances to the surface of the semipermeable membrane, and thus to the efficiency of migration across the membrane.

Device Comprising Semipermeable Membrane and Two Chambers

A device suitable for the present invention comprises a first chamber, suitable for receiving blood, and a second chamber, suitable for receiving the dialysis liquid. The first chamber and the second chamber are separated by at least one semipermeable membrane.

Suitably, the first chamber is divided into a multitude of first chambers. A multitude refers to any integer more than one. Thus, typically, a multitude of first chamber is present in the device. Preferably each first chamber is in contact with the second chamber via a semipermeable membrane. Said first chambers are preferably present in the form of capillaries. This enables that the blood flows through the capillaries while being in contact with the dialysis liquid via the semipermeable membrane.

Optionally, a multitude of second chamber is present in the device. Preferably, each second chamber is in contact with the first chamber via a semipermeable membrane.

In the device, the ratio of total volume of the (multitude of) second chambers to total volume of the (multitude of) first chambers can be in the range of 10:1 to 1:10. Preferably, the total volume of the (multitude of) second chambers is larger than the total volume of the (multitude of) first chambers. A preferred ratio is about 2:1.

Typically, in a device suitable for the present invention, the exposed surface area of the semipermeable membrane can be in the range from 0.01 m$^2$ to 6 m$^2$. A (combined) surface area of up to 6 m$^2$ is typically present when two dialysis units are being used in parallel. Such parallel use of two dialysis units is contemplated in one embodiment of the present invention. Typically, the exposed surface area of any one dialysis unit is in the range from 0.01 m$^2$ to 3 m$^2$, such as from 0.1 m$^2$ to 2.2 m$^2$. In general, surface areas in the lower part of these ranges are particularly suitable for the treatment of children. Exposed surface area refers to the area of the semipermeable membrane exposed to the first chamber on the one side, and simultaneously exposed to the second chamber on the other side. Any additional sections of the membrane, which are not exposed to both chambers simultaneously, but e.g. fixed in a fixation means or otherwise not exposed, are not considered to be part of the exposed surface area. It is also possible that the process of the present invention uses more than one such membrane, either in the same dialysis unit, or in more than one dialysis unit. If more than one dialysis unit is used, such more than one dialysis units can be present in a row, or in parallel, from the perspective of the extracorporeal blood flow path. Preferably, there are two devices for dialysis, each with an exposed surface area as disclosed above.

The process of the present invention thus allows for a transfer of carbon dioxide and other compounds, such as hydrogen cation and bicarbonate, to pass (through the dialysis membrane) to the dialysis liquid. Hence, the process of the present invention is suitable for $CO_2$ removal. This allows for more efficient removal of metabolites, such as $CO_2$, from the blood than conventional methods.

While carbaminohemoglobin and dissolved carbon dioxide are in equilibrium with the bicarbonate ($HCO_3^-$)/$H^+$ ion pair, the rapid conversion requires the enzyme carbonic anhydrase. Optionally, the semipermeable membrane contains carbonic anhydrase activity. This can be achieved by coating the membrane, on the blood-facing side and/or on the side facing the dialysis liquid, with carbonic anhydrase.

Suitably, one chamber is provided on either side of the semipermeable membrane, i.e. a first chamber on one side of the semipermeable membrane, and a second chamber on the other side of the semipermeable membrane. In other words, a device is suitably used which comprises two compartments, separated by a semipermeable membrane. Preferably, the first chamber, the semipermeable membrane and the second chamber are comprised by one device. Thus, blood is present in the first chamber, and the dialysis liquid is present in the second chamber, the chambers being separated by said semipermeable membrane. It is also possible to coat the semipermeable membrane with the enzyme carbonic anhydrase.

Suitably, multiple first chambers are present, each in contact with the second chamber via a semipermeable membrane. Such multiple first chambers can have the form of capillaries; thus, in the process of that embodiment, blood flows through capillaries.

It is not impossible to employ the process of the present invention in a static system. Under such circumstances, the blood is steadily present in the first chamber, i.e. without flowing (entering, passing through and exiting) that chamber. The dialysis liquid is also steadily present in the second chamber, i.e. without flowing (entering, passing through and exiting that chamber). Semi-static and non-static embodiments are, however, preferred. In non-static embodiments, blood flows through the first chamber, so that it enters, passes through and exits the first chamber, and the dialysis liquid flows through the second chamber, so that it enters, passes through and exits the second chamber. Embodiments in which only one of these liquids flows through its respective chamber, while the other one is steadily present in its respective other chamber, i.e. without flowing (entering, passing through and exiting) of the respective other liquid through that respective other chamber, are termed semi-static. Thus, preferably, in the process of the present invention, the blood flows through the first chamber and the dialysis liquid simultaneously flows through the second chamber. Thus, it is preferred that blood is passed through the blood compartment (first chamber) and that the dialysis liquid is passed through the dialysis liquid compartment (second chamber).

The process of the present invention makes it possible to efficiently remove one or more undesired substance as defined above, including $CO_2$, without requiring a gas stream (sweep gas) as in the prior art. In particular, it is neither desired nor required to bring the undesired $CO_2$ into the gas phase. Typically, the dialysis unit used in the present invention does not comprise a chamber having gas (sweep gas) in contact with blood via a membrane (e.g. gas exchange membrane).

Suitably, the device comprising the first chamber, second chamber and the semipermeable membrane is a dialysis unit, optionally comprised in a dialyzer. A dialysis unit is a unit comprising a first chamber as defined herein, a second chamber as defined herein, and a semipermeable membrane, as well as means for entering and removing a fluid (e.g. blood) into and from the first chamber (inlet and outlet), and means for entering and removing a fluid (e.g. dialysis liquid) into and from the second chamber (inlet and outlet). Thus, the first chamber comprises an inlet and an outlet, and the second chamber comprises an inlet and an outlet. Thus, in the present invention, the dialysis unit comprises a biological fluid compartment (first chamber) that is part of the biological fluid circuit, a dialysis liquid compartment (second chamber) that is part of the dialysis liquid circuit, and a semipermeable membrane separating the biological fluid compartment and the dialysis liquid compartment. When a dialysis unit is used, the blood passes through the first chamber, and the dialysis liquid passes through the second chamber.

Alternatively, the device is a device for dialysis, filtration or diafiltration.

Preferably, during the process of the present invention, the second chamber does substantially not comprise any gas phase, i.e. is filled substantially solely with dialysis liquid in the liquid phase. Thus, gas contact of the blood may be entirely excluded, or limited to a minimum, required under the circumstances, e.g. a bubble catcher or a similar device.

The semipermeable membrane used in the present invention is not particularly limited, as long as it is permeable for water and inorganic molecules solubilized in water. A suitable semipermeable membrane for the present invention allows for transfer of the at least one undesired substance across the semipermeable membrane. The membrane can e.g. be selected from conventional semipermeable membranes as currently used e.g. for hemodialysis. It is also conceivable, however, to consider membranes with larger pores than those presently used for dialysis. The diffusion through the membrane can optionally be supported by convective transport by means of filtration.

A dialyzer comprises a dialysis unit as described, and additionally tubing (inlet and outlet) connected with the respective means for entering and removing a fluid into and from said first and second chamber, respectively: the tubing connected to the first chamber (inlet and outlet) is suitable to be connected to the blood system of a human or animal. The dialyzer essentially comprises two chambers separated by a dialysis membrane, to each of which is connected a tubing system for the fluids to be used. Optionally, the tubing connected to the second chamber (inlet and outlet) is suitable to be connected to a regeneration unit. The latter setting allows for regeneration (recirculation, recycling) of the dialysis liquid, as described herein below, as well as in WO 03/094998 A1 and WO 2009/071103 A1, both incorporated herein by reference in their entirety. The dialyzers used in the present invention are not particularly limited, and can be conventional dialyzers currently used e.g. for hemodialysis. In a particular embodiment, the HepaWash® system can be used in the present invention, together with a means for oxygenating blood, as described herein.

It is possible to remove liquid from the blood, if desired. For example, it is possible to remove the same or substantially similar volume of liquids from the blood as has been introduced during steps (i) and (ii) of the process of the present invention (if any liquid has been introduced at all). Alternatively, it is possible to remove even more liquid, if desired.

Dialysis Units

Preferably, two devices for dialysis, or two dialysis units, are used in parallel. This allows for increase of the exposed membrane surface area, and thus for more efficient exchange of the one or more undesired substance across the semipermeable membrane.

Further Process Features and Parameters

The following further features and parameters are suitable for use in connection with the dialysis unit, i.e. in the device comprising the first chamber, the second chamber and the semipermeable membrane.

Conventional components of a dialyzer, such as manometers, air detectors, pumping devices like heparin pumps, blood pumps, etc., form part of the means or device according to the invention.

Single-Use

It is possible to discard the dialysis liquid after exit from the second chamber (outlet). Such embodiments are referred to as "single use" or "single pass" process. The single use embodiment requires the addition of fresh dialysis liquid (into the inlet of the second chamber) during essentially the entire duration of the process.

Single use is possible in the context of the present invention. It is, however, not as convenient as the recycling described below. Therefore, single use is less preferred in the context of the present invention.

Recycling

As opposed to single use, the dialysis liquid can also be recycled ("recycling" or "multi use" or "multi pass"). To that end, dialysis liquid ("used dialysis liquid") exiting from the second chamber (outlet) is collected and returned into the second chamber (inlet). Albumin is relatively costly. It is therefore generally desired to recycle albumin-containing dialysis liquid. In other words, the recycling can result in major cost savings.

The recycling enables also having a high dialysis liquid flow rate of up to 4000 ml/min.

Typically, recycling of the dialysis liquid requires the cleaning or regeneration of the dialysis liquid. Such cleaning or regeneration is achieved by at least one type of treatment step in order to remove undesired substances from the dialysis liquid (i.e. used dialysis liquid) prior to re-entry into the second chamber. Said step occurs outside the second chamber, i.e. at a site different from the site of blood contact. Said at least one treatment step is selected from exposure to an (i) adsorber and/or (ii) diafiltration and/or (iii) acidic pH and/or basic pH (iv) and/or exposure to a permeable or semipermeable membrane (i.e. a membrane different from the one being localized in the dialysis unit separating the first and second chamber). Said adsorber is usually an entity different from albumin; i.e. for albumin-containing dialysate, said adsorber is a further or additional adsorber. In particularly suitable embodiments, said adsorber is capable of binding sodium ions ($Na^+$) and/or chloride ions ($Cl^-$).

Any one or more of such treatment steps can be conducted in series or in parallel (i.e. upon dividing the dialysis liquid). It is possible to foresee that the dialysis liquid is subjected to treatment or purification after being exposed to the blood separated by the semipermeable membrane, i.e. after exiting from the second chamber. Suitable means for treatment or purification of the dialysis liquid include one or more adsorber unit(s), one or more pH change unit(s) and/or one or more diafiltration unit(s). Such units are not mutually exclusive and may be present in row or in parallel. In particular, the recycling of the dialysis liquid of the present invention can also require, and thus involve, an adjustment of the (combined) carbonate/bicarbonate concentration and/or of the pH, so as to ensure that the pH of the dialysis liquid, when being (re)introduced into the first chamber, complies with the properties desired in the context of the present invention, as defined herein. (re)introduced refers to the introduction after recycling.

Flow Rates

The blood is passed through the first chamber, and the dialysis liquid is passed through the second chamber. The flow rate, or speed of the blood and of the dialysis liquid may be selected from constant or varying (changing) over time.

As the both blood oxygenation and carbon dioxide removal are dependent on the blood flow rate, adaptation of the flow rate is usually desired. The following holds: the higher the blood flow rate, the better the oxygenation of the subject being treated; the lower the blood flow rate, the better the carbon dioxide removal.

The blood flow rate is typically adjusted to a range of from 50 ml/min to 7000 ml/min.

In the present invention, the flow-rate is not generally limited. For example, it is possible that the blood flows through the first chamber at a low-flow flow-rate (less than 800 ml/min; preferably 100 to 800 ml/min), at a mid-flow flow-rate (800 to 2400 ml/min), or at a high-flow flow-rate (more than 2400 ml/min). The blood flow rate is typically controlled and regulated and may be adjusted to the treatment conditions and to the dialysis liquid.

In one embodiment, low-flow is most preferred.

In an alternative embodiment, mid-flow is most preferred.

In general, a low-flow and/or mid-flow treatment is easier to handle for the operator than high-flow, and is less risky for the patient than high-flow. In addition, when the process of the present invention is carried out at mid-flow flow-rate, additional lung protective ventilation (LPV) is dispensable; this is a major advantage compared to state of the art mid-flow devices, which usually require additional LPV. The high rate of oxygenation at mid-flow flow rate according to the present invention is possible due to the transfer of undesired substances, such as carbon dioxide to the liquid phase, and due to potential introduction of excess oxygen to blood (to supersaturate blood with oxygen). In processes other than the one subject to the present invention, excess oxygen would evoke the release of hemoglobin-bound $H^+$ ions, and free carbon dioxide gas would arise. This would constitute a risk for gas embolism or, as the solubility of carbon dioxide is about 20 times higher than oxygen, of retro-transportation of dissolved carbon dioxide back into the subject being treated. In view of these considerations, mid-flow blood flow rates are advantageous in the present invention because of their safer handling. At mid-flow flow rates, the lungs can be supported in the present invention up to 100% without requiring any further ventilation device. This is a significant improvement over prior art mid-flow systems for extracorporeal lung support. Such prior art mid-flow systems are disadvantageous firstly because they usually have to be used in combination with lung protective ventilation (LPV). Mechanical ventilation methods are, however, associated with the risk of activation of platelets, inflammation, blood clotting and through so might lead to lethality (Assmann et al., Zeitschrift für Herz-, Thorax-und Gefäßchirurgie, vol. 23, no. 4, pp. 229-234, July 2009). Another disadvantage of combination of prior art systems with LPV is the limited staff and space capacity at hospitals and care providers; however, the combination of protective ventilation and extracorporeal lung support would require at least two devices in parallel. In contrast, the process of the present invention is advantageously carried out without parallel LPV. In other words, an additional lung protective ventilation (LPV), which is common for prior art mid-flow devices, is dispensable.

High-flow flow rates are also possible in the present invention. However, to obtain blood flow rates for high-flow systems a cannulation of larger vessels is necessary, which has to be conducted by a specialist and is associated with certain health risks. That is one of the reasons, why mid-flow flow-rates are considered advantageous in the present invention.

A pump may be provided to direct or control the flow rate of blood.

A pump is typically provided to direct or control the flow rate of the dialysis liquid.

In the process of the present invention, the dialysis liquid flow rate can be in the range from 10 ml/min to 11000 ml/min (i.e. 0.1667 ml/h to 183.333 ml/h). More typically, the dialysis liquid flow rate is selected from the following: slow dialysis liquid flow rates (1-2 l/h) and normal dialysis liquid flow rates (25-60 l/h)/dialyzer, as well as intermediate rates (more than 2 l/h to less than 25 l/h). The flow rate can thus be adapted as required. Higher flow rates of the dialysis liquid generally enable efficient transfer of bicarbonate/carbonate.

In general, it is preferred that the flow rate of the blood is lower than the flow rate of the dialysis liquid. Thereby, an efficient treatment of the blood can be achieved.

In the dialysis unit, i.e. in the device comprising the first chamber, the second chamber and the semipermeable membrane, the blood and the dialysis liquid are preferably not conveyed in counter-current, i.e. are preferably conveyed in co-current. However, in general it is conceivable that blood and dialysis liquid can be passed through the device for dialysis in the same direction or counter-current.

CO$_2$ Removal from the Dialysis Liquid

Figure 2A:
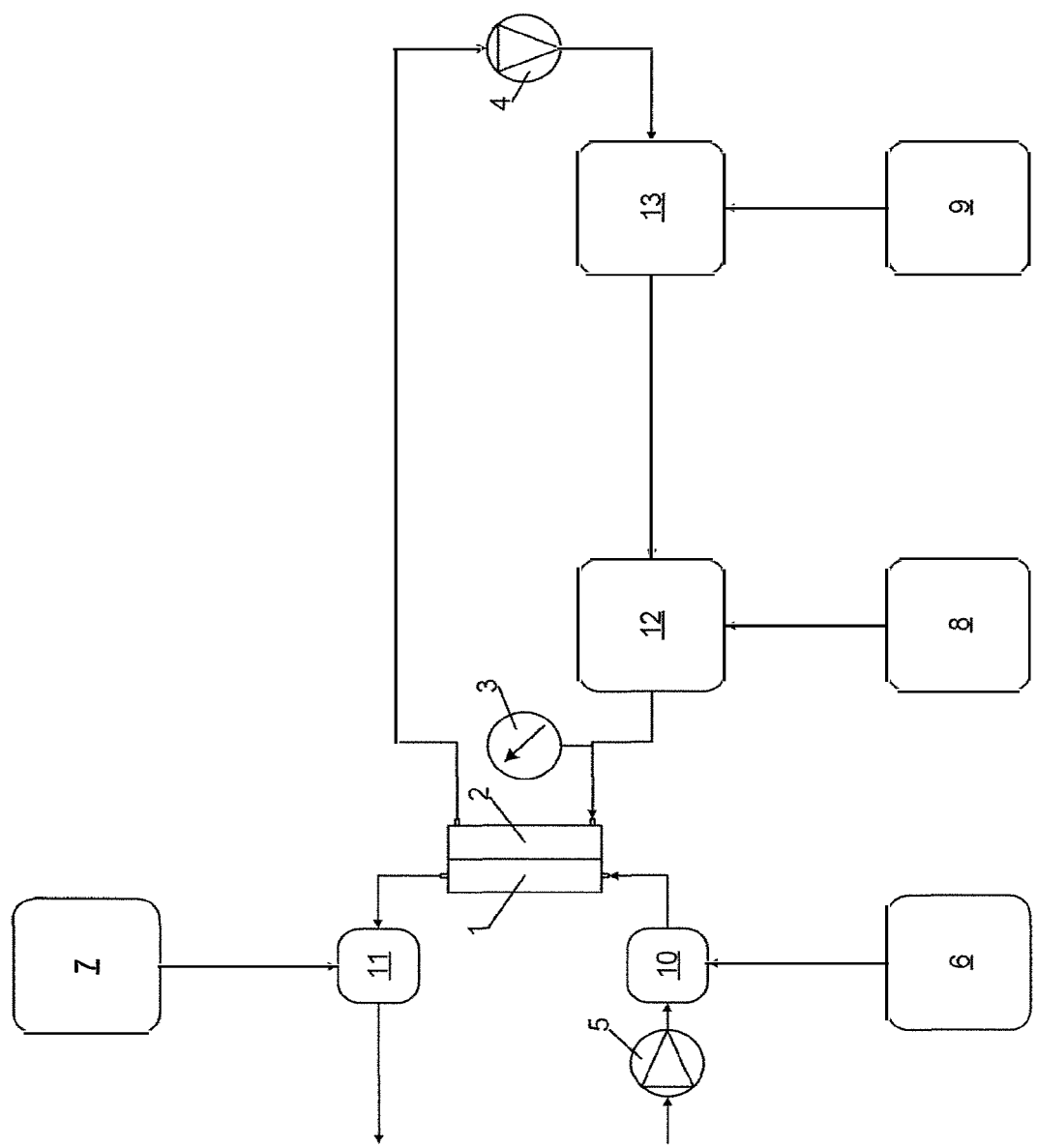
FIG. 2A: Lung support for patients with full renal function.
Figure 2B:
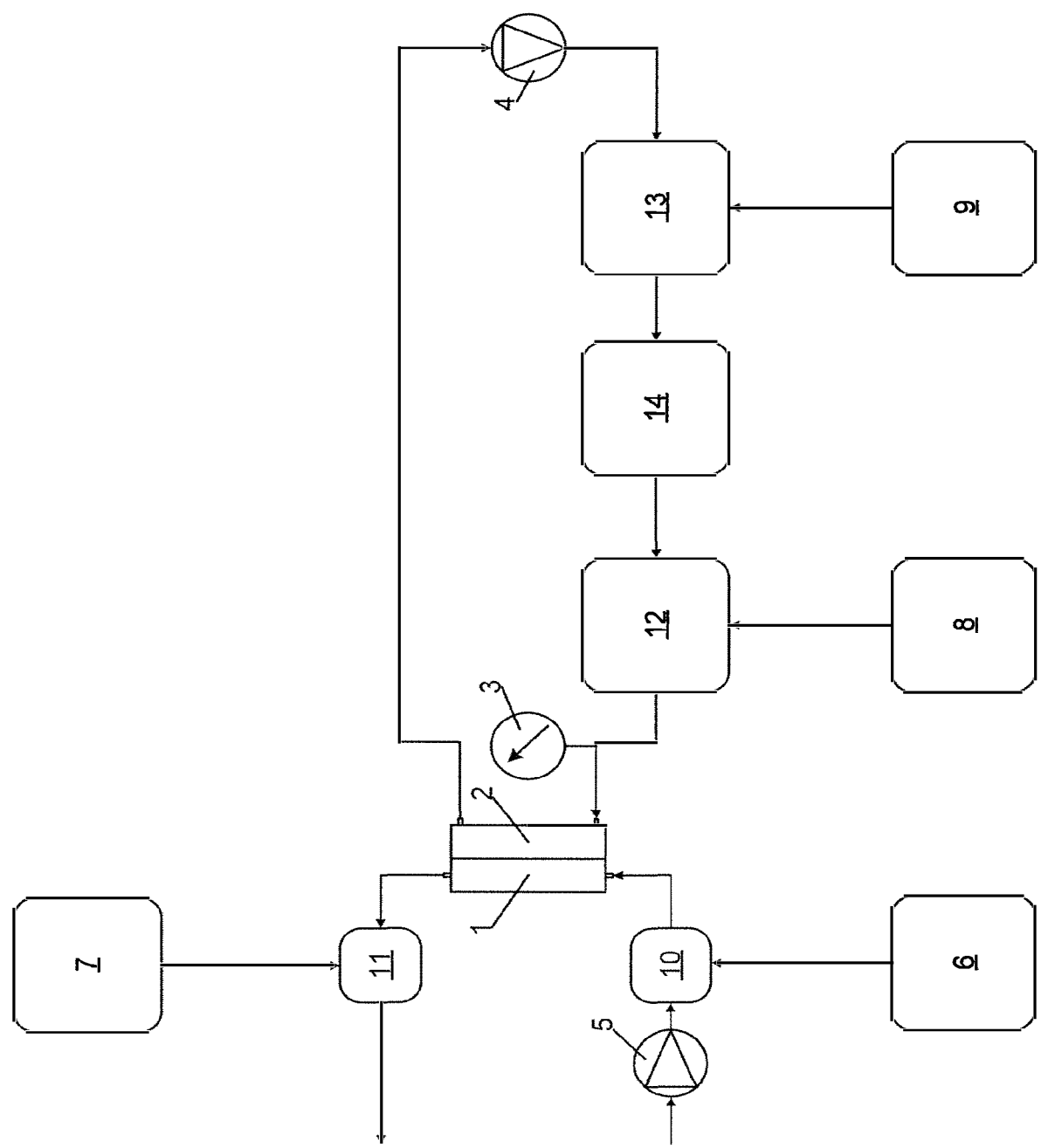
FIG. 2B: Lung support for treatment of patients suffering from kidney failure.
Figure 2C:
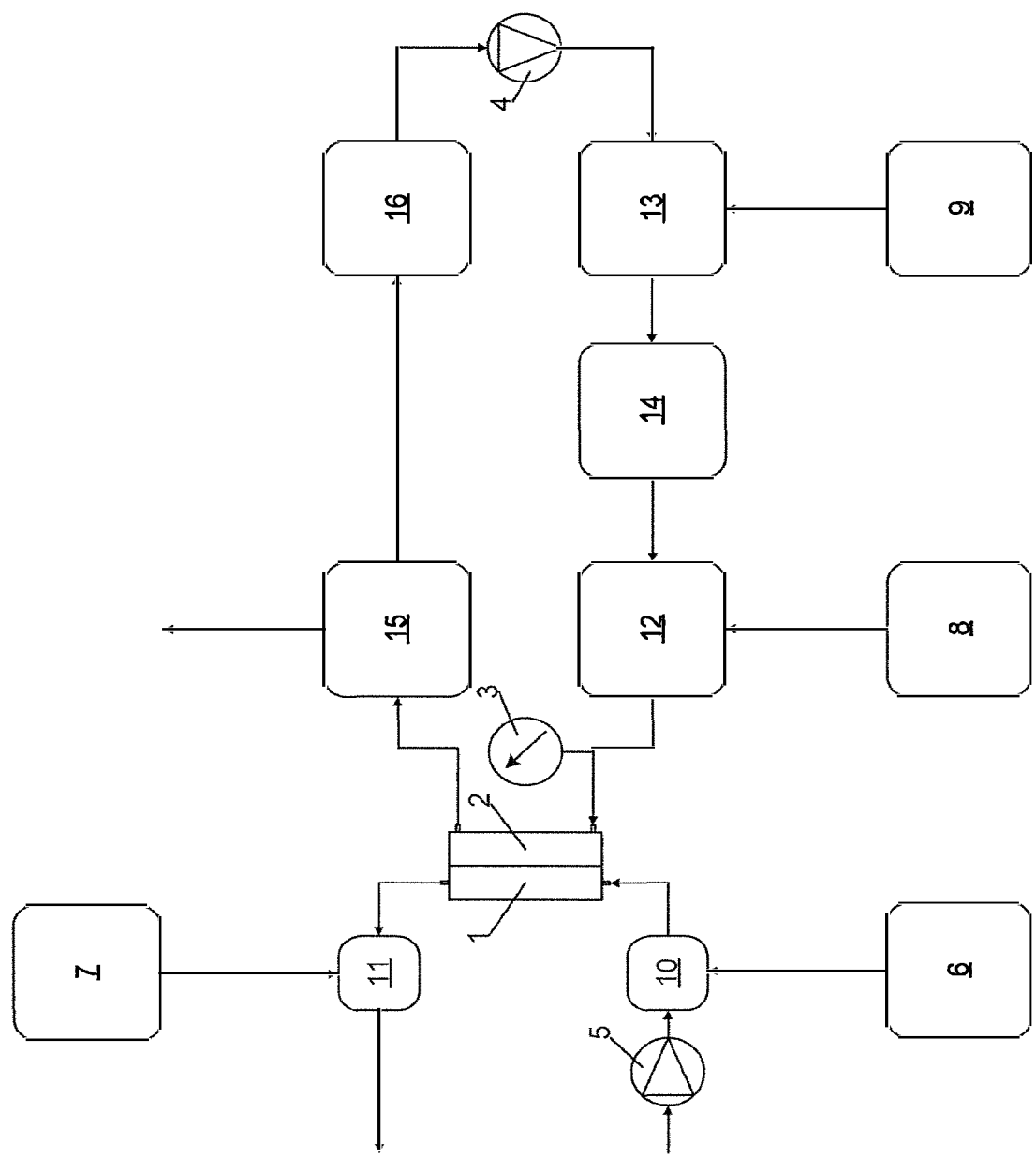
FIG. 2C: Lung support for treatment of patients suffering from kidney and liver failure (i.e. with toxin and/or liquid removal and/or electrolyte compensation).
Figure 2D:
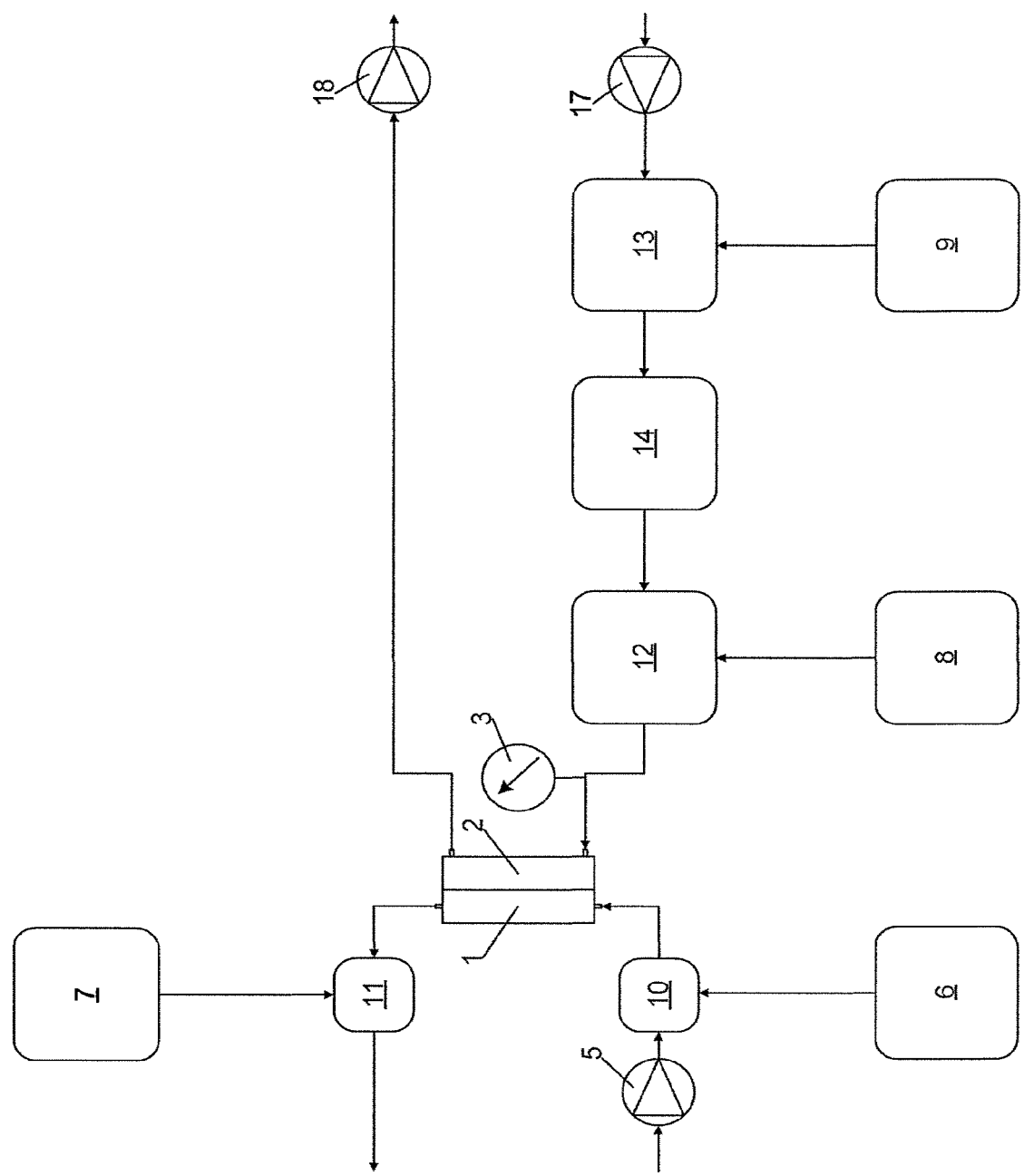
FIG. 2D: Single-pass dialysis for patients requiring lung support and/or kidney support and/or liver support and/or an electrolyte Na, K, Ca, Cl . . . compensation.

In a preferred embodiment of the process of the present invention, a possibility is foreseen to remove carbon dioxide, and/or carbonic acid and/or its dissociation products ($H^+/HCO_3^-$) from the dialysis liquid (FIG. 2C no. 15). This is ideally foreseen in a discrete step, i.e. a step after the dialysis liquid exits the second chamber (outlet). The means for these purposes are not particularly limited, as long as they are suitable. For this treatment carbon dioxide, and/or carbonic acid and/or its dissociation products ($H^+/HCO_3^-$) are suitably removed from the dialysis liquid by degasification (pressure reduction, heating or cooling, ultrasonic, membrane degasification, substitution by inert gas, addition of reductant, freeze-pump-thaw cycling, pH decrease, centrifugal force or addition of degasification additives), filtration, sorption or chemical bonding. For example, said removal can be achieved by degasification (e.g. pressure reduction, heating or cooling, ultrasonic, membrane degasification, substitution by inert gas, addition of reductant, freeze-pump-thaw cycling, pH decrease, centrifugal force or addition of degasification additives), filtration, sorption or chemical bonding and/or a combination of such measures. It is ideally possible to measure the concentration of carbon dioxide and/or carbonic acid and/or hydrogen carbonate, and/or to measure the pH, in the dialysis liquid, after exit of the dialysis liquid from the second chamber. The described removal of carbon dioxide, and/or carbonic acid and/or its dissociation products is particularly suitable in those embodiments wherein the dialysis liquid is recycled, as described herein.

In a particularly suitable embodiment, the process according to the present invention is conducted such that the recycling includes acidification of the dialysis liquid to acidic pH, for formation of carbon dioxide, and removal of carbon dioxide from the dialysis liquid across a carbon dioxide-permeable membrane by means of a bubble trap. Suitably, the membrane is gas-permeable, and carbon dioxide is removed in the gas phase.

Acid/Base Treatment

Albumin is commercially available, but relatively expensive. Therefore, albumin-based dialysis liquids can incur high process costs. In the prior art, recycling of albumin-containing dialysis liquid has been described for the case of liver dialysis, e.g. in WO 03/094998 A1, incorporated herein by reference in its entirety. As described in that patent application, albumin can be recycled based on the principle that the binding affinity of carrier proteins (such as albumin) towards bound substances, such as toxins, may be modified by certain measures, such as pH-changes. The selective decreasing and subsequent increasing (or vice versa) of the pH of a dialysis liquid comprising albumin allows for efficient removal of the bound substances, via dialysis (diffusion) or filtration (convection) or a combination of both processes, hereafter called diafiltration. In general, diafiltration is a dilution process that involves removal or separation of components (permeable molecules like salts, small proteins, solvents etc.,) of a solution based on their molecular size by using filters permeable of said components. Diafiltration-mediated removal of such components allows for subsequent recycling of the albumin. As described in the prior art, albumin can be efficiently regenerated in a dialysis regeneration unit having two parallel dialysis liquid flow paths, i.e. an acidic flow path and an alkaline flow path in parallel (WO 09/071103 A1). The process and device (e.g. dialysis liquid regeneration unit, dialysis unit) described in WO 09/071103 A1 are also suitable for recycling albumin-containing dialysis liquid in the process of the present invention; WO 09/071103 A1 is therefore incorporated herein by reference in its entirety 1.

By the step of treating (cleaning, regenerating) the dialysis liquid at an altered pH, toxins bound e.g. to albumin can be removed. For efficiently removing said toxins, the dialysis liquid regeneration unit according to embodiments of the present invention comprises two flow paths that operate in parallel. The dialysis liquid to be regenerated is divided and conveyed through the two flow paths. In the first flow path, an acidic fluid is added (from an acidic fluid supply unit) to the dialysis liquid. For toxins that are soluble in acidic solution, the concentration of free toxins in solution is increased. In a detoxification unit, which is located downstream of the acidic fluid supply unit, the free toxins are removed from the acidified dialysis liquid flowing in the first flow path. By adding an acidic fluid to the dialysis liquid, removal of acidic soluble toxins is enabled. Furthermore, by decreasing the pH, alkaline soluble toxins may e.g. be precipitated and thereby removed from the dialysis liquid fluid. In the second flow path, which extends in parallel to the first flow path, an alkaline fluid is added (from an alkaline fluid supply unit) to the dialysis liquid flowing in the second flow path. Due to the increase of the pH, the concentration of free alkaline soluble toxins is increased, and thus, removal of alkaline soluble toxins is enabled. These toxins are removed by a further detoxification unit, which is located downstream of the alkaline fluid supply unit. The further detoxification unit is adapted for removing toxins from the alkalized dialysis liquid flowing in the second flow path. Furthermore, by increasing the pH, acidic soluble toxins may e.g. be precipitated and thereby removed from the dialysis liquid fluid. By providing an acidic flow path and an alkaline flow path in parallel, both acidic soluble toxins and alkaline soluble toxins may be (more) efficiently removed from the dialysis liquid. Hence, the dialysis liquid regeneration unit according to embodiments of the present invention is capable of efficiently removing protein-binding toxins. The term "toxin" is understood very broadly herein and encompasses all protein-binding substances, even if they are usually not directly toxic (causing health issues) as such, such as drugs, electrolytes, $H^+$, hormones, fats, vitamins, gases, and metabolic degradation products like bilirubin. Downstream of the acid treatment unit and the base treatment unit, together "pH treatment units" (or detoxification units), the regenerated acidified dialysis liquid from the first flow path may be merged with the regenerated alkalized dialysis liquid from the second flow path, whereby the acidified dialysis liquid from the first flow path and the alkalized dialysis liquid from the second flow path may neutralize one another at least partially. Hence, by merging the flow of acidified dialysis liquid from the first flow path with the flow of alkalized dialysis liquid from the second flow path, a flow of regenerated dialysis liquid at a physiological pH value may be provided.

According to a preferred embodiment, the acidic fluid added by the first supply unit comprises at least one of: hydrochloric acid, sulfuric acid, and acetic acid. In a preferred embodiment, the first supply unit is adapted for adjusting the pH of the dialysis liquid in the first flow path to a pH from 1 to 7, preferably from 2.5 to 5.5.

Preferably, the alkaline fluid added by the second supply unit comprises at least one of: sodium hydroxide solution, and potassium hydroxide solution. In a preferred embodiment, the second supply unit is adapted for adjusting the pH of the dialysis liquid in the second flow path to a pH from 7 to 13, preferably from 8 to 13, more preferably from 8 to 11.

Further preferably, the acidic fluid and the alkaline fluid are chosen such that "physiological" neutralization products are generated during neutralization. For example, a certain concentration of the formed neutralization products might already be present in the respective biological fluid anyway. For example, when using aqueous hydrochloric acid and aqueous sodium hydroxide solution, amounts of NaCl occur by neutralization of the acidified flow and the alkalized flow. NaCl is typically also present in a biological fluid, like e.g. blood or blood serum.

According to a preferred embodiment, by decreasing the pH of the dialysis liquid in the first flow path, a concentration ratio of toxin-carrier-complex to free toxin and free carrier substance is shifted in favour of the free toxin for at least some of the toxins in the dialysis liquid, thereby increasing a concentration of free toxins in the dialysis liquid. By decreasing the pH of the dialysis liquid in the first flow path, the solubility of acidic soluble toxins (like e.g. magnesium or copper) is increased, whereas the binding affinity of the acidic soluble toxins to the carrier substances is reduced. Accordingly, the concentration of free toxins in solution is increased.

Further preferably, the detoxification unit is adapted for at least partially removing said free toxins. Due to the increased concentration of free toxins, said toxins may be removed at an increased rate.

Furthermore, by decreasing the pH value of the dialysis liquid in the first flow path, some of the alkaline soluble toxins may e.g. be precipitated and thereby removed from the dialysis liquid fluid.

In a preferred embodiment, by increasing the pH of the dialysis liquid in the second flow path, a concentration ratio of toxin-carrier-complex to free toxin and free carrier substance is shifted in favour of the free toxin for at least some of the toxins in the dialysis liquid, thereby increasing a concentration of free toxins in the dialysis liquid. By increasing the pH of the dialysis liquid in the second flow path, solubility of alkaline soluble substances (like e.g. bilirubin) is increased, whereas the binding affinity of the alkaline soluble toxins to the carrier substances is reduced. Accordingly, the concentration of free toxins in solution is increased.

Preferably, the further detoxification unit is adapted for at least partially removing said free toxins. Due to the increased concentration of free toxins, said toxins may be removed at an increased rate.

Furthermore, by increasing the pH value of the dialysis liquid in the second flow path, some of the acidic soluble toxins may e.g. be precipitated and thereby removed from the dialysis liquid fluid.

According to a further preferred embodiment, by increasing the temperature of the dialysis liquid, the concentration ratio of toxin-carrier-complex to free toxin and free carrier substance is shifted in favour of the free toxin for at least some of the toxins in the dialysis liquid, thereby increasing a concentration of free toxins in the dialysis liquid. Accordingly, the free toxins may be removed at an increased rate by the detoxification units.

Further aspects of the recycling of albumin-containing dialysis liquid are described in WO 2009/071103 A1, incorporated herein by reference in its entirety, including illustrations in the figures. In addition to the findings described in WO 2009/071103 A1, albumin has also contributes to the excellent buffering capacity of dialysis liquids according to the present invention.

Adsorber Treatment/Adsorption

In order to extract or remove excess or undesired substances, like electrolytes (e.g. cations such as potassium, sodium and calcium cations; or anions, such as chloride, carbonate or bicarbonate cations), an adsorber can be brought in contact with the dialysis liquid. In general, the adsorber is capable of adsorbing at least one undesired substance present in the patient's blood (e.g. urea, uric acid, electrolytes, sodium, calcium or potassium cations; chloride anions). Typically, an adsorber is present in an adsorber unit, i.e. a stationary unit through which the dialysis liquid is passed. The type or composition or material of the adsorber is not particularly limited, as long as it has the capacity to bind at least one of the substances to be removed from the dialysis liquid. Different adsorber types are known in the art. By appropriate choice of the adsorber, the process can be adjusted to the actual needs, e.g. needs of an individual patient. An adsorber is particularly useful in recycling embodiments, i.e. when it is intended to recycle the dialysis liquid.

Aspects of Regeneration of the Dialysis Liquid

Excess or undesired substances can be removed from the dialysis liquid (used dialysis liquid) across a membrane, i.e. a permeable or semipermeable membrane. For example, gases and/or solutes/ions dissolved in the dialysis liquid can be removed by such a membrane treatment. In a preferred embodiment, carbon dioxide is removed, either as a gas or in the state of being dissolved in a liquid. One particularly suitable way of removing carbon dioxide consists of bringing the dialysis liquid into contact with a membrane which is permeable for carbon dioxide. The dialysis liquid has a certain pressure $p_1$, and the pressure of the fluid (liquid or gas) on the other side of said membrane, $p_2$, is lower, i.e. $p_2 < p_1$. The object of $CO_2$ removal from the used dialysis liquid can also, or alternatively, be achieved if the partial pressure of $CO_2$ is lower in the fluid on the other side of said membrane. Similarly, it is possible to remove hydrogen carbonate along a concentration gradient, i.e. by bringing the used dialysis liquid into contact with a bicarbonate-permeable membrane, as long as the (combined) carbonate/bicarbonate concentration in the fluid (liquid) on the other side of the membrane is lower than the (combined) carbonate/bicarbonate concentration of the used dialysis liquid. In any case, the membrane used is not permeable for albumin. This can be realized by selecting a membrane with an appropriate pore size. Such membrane treatment is particularly useful for recycling embodiments.

Medical Uses

It is possible and desired to exploit the process of the present invention, as described above, for medical purposes. Any activity directed at treatment of the human or animal body by surgery or therapy, particularly those aiming at preventing or improving a condition in a living subject, i.e. serving a medical purpose, may be referred to as a medical method or medical use. In general, the terms method and process are used interchangeably herein. Sometimes, however, the term method is used to refer particularly to medical methods; the medical methods of the present invention can involve any and all aspects of the above described process for removal of an undesired substance from blood. In particular, this invention provides a method for extracorporeal treatment of blood from a patient in need of such treatment. The extracorporeal blood is subjected to dialysis process as described herein, i.e.—generally speaking—is being exposed to a dialysis liquid separated by a semipermeable membrane. For this purpose, blood is removed from a subject, subjected to the process of the present invention, and suitably returned to the subject. In general, in such methods, venous blood from a patient is removed and entered into the first chamber of the process of the present invention. This allows for treatment of the blood in the process of the present invention, in any and all aspects described herein. Subsequently, the blood ("treated blood") exits the first chamber and can be returned to the patient. The treated blood most typically is entered into a vein of the patient, but can alternatively be returned into an artery, however the latter is suitably limited to processes wherein the blood is also subjected to oxygenation. All these aspects spanning the process from removal of patient blood from the body until returning treated patient blood into the body are common to medical the methods for all indications described herein.

The findings of the present invention enable its exploitation in the treatment of the human or animal body by therapy (generally referred to as medical uses). It is possible to customize the medical uses of the present invention specifically to the actual needs of the respective patient. Although, in nature, gas-exchange is not limited to organisms having lungs, but equally occurs in organisms having gills, such as fish, the medical uses of the present invention are focused at the goal of lung support, i.e. for treating or preventing certain conditions in organisms having lungs, such as preferably mammals, and more preferably humans. Therefore, gills, and/or organisms having gills, are not discussed in detail in this specification.

Preferably, in the medical methods, the dialysis liquid is characterized by an osmolarity, which is substantially identical to the osmolarity of blood, i.e. of the blood of the species (e.g. human) being dialyzed in the dialysis unit.

Optionally, the method of the invention, typically being suitable for extracorporeal treatment of blood, does not (or at least not necessarily) comprise an invasive step and/or does not comprise a step representing a substantial physical intervention on the body and/or does not comprise a step which requires professional medical expertise to be carried out and/or does not comprise a step which entails a substantial health risk even when carried out with professional care and expertise. Preferably, the method of the invention does not comprise an invasive step representing a substantial physical intervention on the body which requires professional medical expertise to be carried out and which entails a substantial health risk even when carried out with the required professional care and expertise. For example, the method of the invention does optionally not comprise an invasive step of connecting and/or disconnecting a dialysis system with the human or animal body. In another example, the contacting of an extracorporeal device to the venous blood of the living subject, and thus the respective medical method, does not entail a substantial health risk.

The medical methods of the present invention are useful or suitable for treating at least one condition selected from respiratory acidosis, metabolic acidosis, lung failure or lung disorder, kidney failure, multi-organ failure and combinations of any one or more of these. The method can be configured to the condition to be treated, or to the individual to be treated in particular (personalized medicine). While the following sections discuss the treatment of these conditions, respective methods of prevention are equally encompassed by the present invention.

All these treatment methods involve the withdrawing venous blood from a subject, thus yielding extracorporeal blood; exposing the extracorporeal blood to contact with the dialysis liquid as described herein via a semipermeable membrane, as described in the context of the process of the present invention, thus yielding treated blood, and returning the treated blood into the same subject, preferably into the vein of the subject, and in a less preferred embodiment into the artery of the subject. Particular configurations are described in the following.

Treatment of Lung Failure or Lung Disorder

The methods of the present invention are suitable for treating patients suffering from acute or chronic respiratory failure (lung failure). Subjects suffering from lung failure, but typically not from failure of other organs, such as kidney failure or liver failure, develop respiratory acidosis, or are at risk of developing respiratory acidosis. This is because removal of carbon dioxide does not occur as efficiently as in healthy subjects, or does not occur at all. This patient group includes patients suffering from asthma, hypoventilation, lung diseases such as lung cancer, complications associated with smoking and with exposure to other air-born toxins or particles, or muscle dystrophy, or emphysema, particularly late-stage emphysema. Many patients suffering from such lung diseases have a completely working kidney (full renal function). The present invention enables extracorporeal oxygenation as well as extracorporeal removal of at least one undesired substance, such as carbon dioxide or bicarbonate or hydrogen cations. Therefore, the present invention provides a full lung support and it particularly suites for that patient group.

The dialysis liquid is either discarded, or, preferably, recycled. In the latter case it is preferable to subject the dialysis liquid to a membrane treatment. By the membrane treatment, carbon dioxide and/or bicarbonate and/or carbonate and/or carbonic acid may be removed, or partially removed. This allows for recycling of the dialysis liquid. For removal of carbon dioxide, the membrane treatment is preferably carried out at low pH, i.e. following acidification of the dialysate.

Treatment of Combined Lung Failure/Kidney Failure

Besides the lungs, the kidneys play an important role in maintaining the pH of bodily fluids. In a healthy human or animal subject, the kidneys collaborate with the lungs in the regulation of the carbonate/bicarbonate ratio and in the regulation of blood pH. Thus, in general, the kidneys play an important role in maintaining acid-base homeostasis of healthy individuals by regulating the pH of the blood plasma: main functions include reabsorption of bicarbonate from urine, and excretion of hydrogen cations into urine. These functions of the kidneys are important for maintaining acid-base balance, and can also contribute to controlling blood pH.

Renal replacement therapy (RRT) is being widely used in modern intensive care settings/intensive care unit (ICU) for treating such subjects. In subjects in the intensive care unit (ICU subjects), acute renal failure (ARF) is frequent, as a part of multiple organ dysfunction syndrome (MODS), in postoperative states and after interventional studies, in already susceptible individuals. In general, ICU subjects are in need of different organ support such as continuous renal replacement therapy (CRRT), liver dialysis and mechanical ventilation. In contrast to the state of the art, which traditionally requires at least three different devices for the treatment of kidney, liver and lung failure in such subjects (or, in addition to a device for the treatment of liver failure, a combined three-chamber device for the treatment of kidney/lung failure, PrismaLung™, DE 10 2009 008601 A1; WO 2010/091867 A1; Novalung), the present invention provides a significant improvement.

The proper functioning of the kidneys is affected in patients suffering from kidney failure. In contrast to conventional extracorporeal lung support, e.g. ECMO, which enables only gas exchange, and does not support the kidney, the present invention also enables the treatment of kidney failure, and of multi-organ failure. Thus, the present invention allows for treating subjects suffering inter alia from acute or chronic kidney (renal) insufficiency, or chronic renal failure (CRF). The present invention also allows treating of patients suffering from kidney diseases such as kidney cancer, as well as complications associated with intoxication and with exposure to certain medicaments.

For treating multi-organ failure, e.g. failure of both lungs and kidney, the present invention provides a further advantage over the prior art because, instead of two separate devices, one for treating lung failure and one for treating kidney failure, only one single device is used. The single device comprises the first and second chamber for contacting blood and dialysis liquid separated by the semipermeable membrane in the process of the present invention.

In the present invention, the conditions ((combined) carbonate/bicarbonate concentration of the dialysis liquid entering the second chamber; pH of the blood exiting the first chamber, bicarbonate concentration of blood exiting the first chamber) are suitably selected from the conditions described herein for any of respiratory or metabolic acidosis, preferably those described for metabolic acidosis. Additionally, it is preferable to include an adsorber which is suitable for binding or adsorbing at least one undesired substance present in the patient's blood (e.g. urea, uric acid, electrolytes, sodium, calcium or potassium cations; chloride anions). For example, in patients suffering from kidney failure, it is typical that the kidney fails to maintain physiological concentrations or desired concentrations of solutes including of sodium, calcium or potassium cations; and/or of chloride anions, in the blood. These deficiencies are addressed by the present invention. In particular, the dialysis liquid can be adapted specifically to in order to maintain desired levels of the respective solute(s). To that end, the dialysis liquid contains either (i) more or (ii) less of the respective solute(s) than the desired blood concentration of the respective solute(s), depending on whether it is desired to (i) increase or to (ii) decrease the concentration of the respective solute (s) in blood of the subject being treated. The present invention provides a versatile kidney support: for example, if it is desired to support the kidneys in the removal of excess bicarbonate from blood, the dialysis liquid is preferably selected such that it does not comprise added bicarbonate; preferably the (combined) concentration of carbonate and bicarbonate is below 5 mmol/l; more preferably 0 mmol/l. In a further example, if it is desired to support the kidneys in the regulation of blood pH (e.g. for treating acidosis), the dialysis liquid is preferably selected such that its pH and/or buffering capacity is/are adapted to such goal: for example, the pH may be in the range of pH 8.0 to 11.0, and/or the buffering capacity for $H^+$ ions may be 12 mmol/l or more. Further aspects of treating acidosis are described in the following.

Treatment of Combined Kidney/Liver/Lung Failure

The present invention also allows for treating subjects suffering from acute or chronic liver failure in addition to lung failure and/or kidney failure. Typical treatment in accordance with the present invention involves extracorporeal toxin removal. For the treatment of such subjects, the methods described in WO 2009/071103 A1 and/or WO 03/094998 A1, or the methods made available through the company Hepa Wash (Munich, Germany), can be modified such that the dialysis liquid complies with the framework dialysis liquid of the present invention, or with any embodiments thereof. In such methods, albumin has a dual or synergistic function: it not only binds toxins (which addresses liver insufficiency) but also buffers the dialysis liquid, together with carbonate (which addresses lung insufficiency). That means, that in addition to the functionalities described in WO 2009/071103 A1 and/or WO 03/094998 A1, it is possible to perform a lung support and/or to correct the blood pH to a physiological level or otherwise desired level. This treatment allows to combine a kidney dialysis, liver dialysis and a lung support comprising a carbon dioxide removal and blood oxygenation in one single device. Modifications or configurations described above for the treatment of kidney failure, such as presence of an adsorber, are suitably employed also in this embodiment.

Treatment of Respiratory Acidosis

The methods of the present invention are suitable for treating patients suffering from acute or chronic respiratory acidosis. Patient groups include subjects suffering from hypoventilation, lung tumors, asthma, muscular dystrophy or emphysema, particularly late-stage emphysema. For the treatment of subjects suffering from respiratory acidosis, the dialysis liquid, at the stage of entering the second chamber, suitably contains a low (combined) carbonate/bicarbonate concentration, in the range from 0 to maximally 40 mmol/l. In fact, for respiratory acidosis, the preferred (combined) carbonate/bicarbonate concentration is as low as possible, i.e. 0 mmol/l or more than 0 mmol/l. Subranges include 1 to 35 mmol/l, 2 to 30 mmol/l, 3 to 25 mmol/l, 4 to 20 mmol/l, 5 to 15 mmol/l, e.g. 10 mmol/l.

In general, a (combined) carbonate/bicarbonate concentration at the lower end of the above range or subrange allows for efficient removal of withdrawal of undesired substances, such as bicarbonate, $CO_2$ and carbonate, from the blood.

Treatment of respiratory acidosis requires adjustment of the blood pH. Therefore, the dialysis liquid for treatment of that patient group is suitably adjusted to have a buffering capacity of at least 12 mmol/l, as defined herein. The treatment of acidosis patients together with blood oxygenation typically requires addition of 2,3-DPG to the dialysis liquid, as described above. This is because acidosis patients typically produce less 2,3-DPG than healthy subjects.

When the (combined) carbonate/bicarbonate concentration in the dialysis liquid is low (e.g. 0 mmol/l or 0 to 10 mmol/l), then the desired buffering capacity is suitably mainly provided by a sufficient amount of other buffering agents in the dialysis liquid, typically albumin and optionally Tris. Particularly, when no carbonate/bicarbonate is added to the dialysis liquid (i.e. the carbonate/bicarbonate concentration in the dialysis liquid is 0 mmol/l or near 0 mmol/l), then it is preferable that both Tris and albumin are present in the dialysis liquid. The concentrations of these buffering agents are selected such that the buffering capacity exceeds the buffering capacity of blood plasma. This allows for efficient adjustment of the blood pH.

It is also possible to increase the (combined) carbonate/bicarbonate concentration over the course of treatment. This allows to adapt the treatment to the needs of an individual (personalized medicine).

Following exposure to such dialysis liquid via the semipermeable membrane, the blood typically has a pH in the range of 7.40 or more; such as higher than 7.40 but not higher than 8.0, such as pH 7.5 to 7.9, or pH 7.6 to 7.8, or pH 7.65 to 7.75, e.g. 7.7. Such blood is returned into the subject.

It is known that, in subjects suffering from respiratory acidosis (i.e. excess dissolved $CO_2$ in the body fluids due to inefficient removal in the lungs), the kidney oftentimes reacts, with some delay of e.g. 3 weeks, by production of increased amounts of bicarbonate. The present invention allows to treat subjects suffering from respiratory acidosis during the entire course of the disease, i.e. at early stages when mainly the removal of excess $CO_2$ from the body fluids is desired, as well as at later stages, when (additionally) the removal of excess bicarbonate from the body fluids is desired. Further, the removal of excess $H^+$ ions from the body fluids is possible at all stages of the disease. During the course of treatment, the physician can alter the composition and pH of the dialysis liquid based on the guidance provided herein. It is also possible to gradually increase the (combined) carbonate/bicarbonate concentration over the course of treatment, within the range of the present invention (0 to 40 mmol/l).

The oxygenation of step of the process of the present invention contributes to the release of $H^+$ ions and of $CO_2$ from hemoglobin. The molecular reason is the extracorporeal exploitation of the Haldane effect, as described above. Thus, owing to the Haldane effect, the oxygenation step renders the removal of these undesired substances from blood very efficient. This is a major improvement over prior art methods.

Treatment of Metabolic Acidosis

The present invention also includes a method of treating metabolic acidosis. Metabolic acidosis, on a molecular level, is caused by an increased amount of acidic organic molecules, caused by increased production of organic acids (e.g. lactic acid) as a result of increased metabolic activity and/or by disturbances in the ability to excrete acid via the kidneys. Metabolic acidosis in chronic renal failure (CRF) is the result of a decreased ability to excrete nonvolatile acid and the reduced renal synthesis of bicarbonate, and thus an increase in hydrogen cations in the body. Without limitation thereto, organic acids can originate for example from amino acid residues of protein catabolism or from accumulation of ketoacids (ketosis) during starvation or in diabetic acidosis. While, in many instances, the affected body attempts compensating metabolic acidosis by respiration (respiratory compensation), non-volatile metabolites are not excreted by this route, and affected subjects are at risk for exhaustion leading to respiratory failure. The present invention provides a solution: Either as a preventive measure, or as a therapeutic measure, i.e. when metabolic acidosis is severe and can no longer be compensated for adequately by the lungs, a treatment by the method of the present invention may be indicated:

A high pH of the dialysis liquid is desired, e.g. pH 8.0 to 11.0, preferably pH 8.0 to 9.0 for the treatment of subjects suffering from metabolic acidosis. The buffering capacity of the dialysis liquid is higher than the buffering capacity of blood plasma. The combination of high pH of the dialysis liquid and high buffering capacity of the dialysis liquid allows for efficient adjustment of the blood pH, and minimal net flux (addition or removal) of substances of bicarbonate, $CO_2$ and carbonate from the blood. In particular, the flux can be increased compared to standard dialysis methods.

The treatment of acidosis patients together with blood oxygenation typically requires addition of 2,3-DPG to the dialysis liquid, as described above. This is because acidosis patients typically produce less 2,3-DPG than healthy subjects. Following exposure to such dialysis liquid via the semipermeable membrane, the blood typically has a pH in the range of desired to adjust the blood pH to a range or value encompassing that range, i.e. 7.0 to 7.8, 7.2 to 7.6, or 7.3 to 7.5, 7.35 to 7.45, and most preferably exactly or about 7.40.

For the treatment of subjects suffering from acute or chronic metabolic acidosis, with normal lung function, the dialysis liquid, at the stage of entering the second chamber, suitably contains carbonate as an additional buffering agent. A suitable (combined) carbonate/bicarbonate concentration lies in the range from 20 to 40 mmol/l, preferably 25 to 35 mmol/l, more preferably exactly or about 30 mmol/l.

The present invention also allows for the treatment of a condition characterized by a combination of respiratory acidosis and metabolic acidosis. This is possible because the dialysis liquid, particularly the pH and the (combined) carbonate/bicarbonate concentration in the dialysis liquid, can be adjusted to individual needs.

However, for the treatment of a subject subgroup that is characterized by acute or chronic metabolic acidosis, but with impaired lung function, the dialysis liquid preferably does not contain any added carbonate/bicarbonate. A suitable dialysis liquid for that type of patients suitably contains a (combined) carbonate/bicarbonate concentration in the range from 0 to 5 mmol/l (preferably 0 mmol/l). The buffering capacity is provided by albumin alone; or by albumin and a further suitable non-carbonate/non-bicarbonate buffering agent, e.g. Tris, within the concentration range defined above. For example, if the (combined) carbonate/bicarbonate concentration in the dialysis liquid were identical to the (combined) carbonate/bicarbonate concentration in the patient's blood, no net transfer of carbonate/bicarbonate (i.e. removal) would be expected.

Treatment of Combined Organ Insufficiency and Treatment of Cardiovascular Diseases In many cases, subjects suffering from lung failure and/or from inefficient gas exchange in the lungs, are also affected by dysfunction of other organs. The methods of the present invention are also suitable for treating such subjects, and thus to support these organs.

In particular, in subjects suffering from cardiovascular disease, particularly impaired function of the heart and thus impaired blood flow, the blood transport to the lungs is oftentimes inefficient. Thus, suffering from such a cardiovascular condition, as a consequence of said cardiovascular condition, also suffer from impaired gas exchange in the lungs, i.e. impaired carbon dioxide release in the lungs and/or impaired blood oxygenation in the lungs.

The present invention allows to treat not only the consequence (impaired gas exchange in the lungs), but also the reason (cardiovascular disease, e.g. impaired function of the heart and thus impaired blood flow). This is achieved by removing blood from a vein of the subject to be treated, subjecting said blood to the extracorporeal lung support according to the present invention, and returning the blood into an artery of the subject, and by pumping the blood through the first chamber. For that purpose, a pump is provided either before the first chamber or after the first chamber. The pump moves the blood through the extracorporeal circuit and thus at least partially substitutes the impaired function of the heart.

In view of the above, the present invention provides in a further aspect a dialysis liquid for use in the treatment and/or prevention of a disease selected from lung failure, respiratory acidosis, metabolic acidosis, kidney failure, a cardiovascular disease or any combination thereof, wherein the dialysis liquid
(i) comprises albumin, preferably 10 to 60 g/l albumin,
(ii) has a pH the range from pH 6.8 to pH 11; and
(iii) is oxygenated.

Preferred embodiments of such a dialysis liquid for use according to the present invention correspond to preferred embodiments of the dialysis liquid as described above and to preferred embodiments of the processes and/or methods as described above. For example, such a dialysis liquid is preferably oxygenated by the process for oxygenating a dialysis fluid as described herein.

Preferably, an "oxygenated" dialysis liquid contains dissolved oxygen. More preferably, the amount of dissolved oxygen in an "oxygenated" dialysis liquid exceeds the amount of dissolved oxygen in water under normal conditions (i.e. at a temperature of 293.15 K and a pressure of 14.696 psi).

Moreover, the present invention also provides a dialysis liquid for use in a method of treating a human or animal subject by therapy,
wherein the dialysis liquid has a pH the range from pH 6.8 to pH 11; and wherein the dialysis liquid comprises albumin, preferably 10 to 60 g/l albumin;
and wherein said use preferably comprises the steps of:
(i) removing blood from a vein or artery of said subject;
(ii) subjecting blood to a process according to any one of claims 1 to 29, thereby using the dialysis liquid; and reintroducing blood into an artery or vein of said subject.
More preferably, the dialysis liquid is oxygenated.

EXAMPLES

The following examples are provided for illustrative purposes. These examples do not limit the invention.

Example 1: Buffering Capacity of Solutions Comprising One or More Buffering Agents The buffering capacity of various aqueous solutions comprising one or more buffering agents was experimentally tested. These aqueous solutions are exemplary liquids, the buffering capacity of which corresponds either to dialysis liquids (dialysates) according to the present invention or to dialysis liquids (dialysates) for comparative purposes.

1A: Preparation of Liquids

These exemplary liquids were prepared as follows:

For the preparation of exemplary dialysis liquids according to the present invention and of reference liquids, pure water (osmosis quality) was used as a basis, and one or more buffering agents according to the present invention (albumin and/or sodium bicarbonate ("soda") and/or Tris(hydroxymethyl)aminomethane (Tris/THAM)) was added. In particular, albumin (at the concentration indicated below) and/or bicarbonate (at the concentration indicated below) and/or Tris (at the concentration indicated below) was dissolved in water. Subsequently or simultaneously, the pH was adjusted to the values indicated below. If necessary, addition of albumin and adjustment of pH may be carried out simultaneously. In some instances, albumin dissolves more rapidly at or near the desired pH values as indicated in the Table below. At any rate, the pH is double-checked, and, if necessary, adjusted, once all the buffering agent(s) has/have been dissolved. Adjustment of the pH is typically done by addition of acidic concentrate (aqueous HCl) and/or by addition of basic concentrate (aqueous NaOH).

For comparative purposes, solutions were prepared to which no buffering agent (albumin, carbonate/bicarbonate, Tris) was added. The pH of these solutions was adjusted to 7.45 and 9, respectively, as indicated in the Table below.

For further comparative, two acetate-containing exemplary liquids, additionally containing sodium bicarbonate, within the range described in the prior art were prepared. For details, see the Table below.

Additionally, four exclusively Tris-containing exemplary liquids were prepared. To that end, two solutions of Tris (Tris(hydroxymethyl)-aminomethane) were prepared:
Tris 38 mmol/l: initial pH after dissolution: pH 10.45.
Tris 20 mmol/l: initial pH after dissolution: pH 10.14.
HCl (0.1 M or 0.2M) was added until the pH value indicated in the below table (pH 7.45 or pH 9.0, respectively) was reached, as indicated in the table below. Thereby, Tris-containing exemplary liquids were prepared.

When the exemplary liquids were prepared, carbonate (e.g. sodium carbonate) was not added. However, it is understood that carbonate and bicarbonate are present in dynamic equilibrium, as a function of the pH. Therefore, any exemplary liquid made by addition of a certain amount of bicarbonate (e.g. 20 mmol/l) and adjustment to a certain pH (e.g. pH 9) will comprise a combined concentration of bicarbonate and carbonate (e.g. in that case 20 mmol/l).

In detail, the following exemplary liquids were prepared:

TABLE 1

| | Buffering agent | pH | Comment (if any) |
|---|---|---|---|
| 1 | no buffering agent | pH 7.45 | Dialysis liquid without buffering agent |
| 2 | no buffering agent | pH 9.0 | Dialysis liquid without buffering agent |
| 3 | 20 g/l albumin | pH 7.45 | Dialysis liquid with buffering agent |
| 4 | 20 g/l albumin | pH 9 | Dialysis liquid with buffering agent |
| 5 | 20 mmol/l sodium bicarbonate (soda) | pH 7.45 | Dialysis liquid with buffering agent |
| 6 | 20 mmol/l sodium bicarbonate (soda) | pH 9 | Dialysis liquid with buffering agent |
| 7 | 20 mmol/l sodium bicarbonate (soda) + 20 g/l albumin | pH 7.45 | Dialysis liquid with buffering agent |
| 8 | 20 mmol/l sodium bicarbonate (soda) + 20 g/l albumin | pH 9 | Dialysis liquid with buffering agent |
| 9 | 38 mmol/l sodium bicarbonate (soda) + 4 mmol/l acetic acid | pH 7.6 | Dialysis liquid as described in the prior art |
| 10 | 20 mmol/l sodium bicarbonate + 4 mmol/l acetic acid | pH 7.25 | Dialysis liquid as described in the prior art |
| 11 | 20 mmol/l Tris | pH 7.45 | Tris solution only |
| 12 | 20 mmol/l Tris | pH 9 | Tris solution only |
| 13 | 38 mmol/l Tris | pH 7.45 | Tris solution only |
| 14 | 38 mmol/l Tris | pH 9 | Tris solution only |

In FIG. 1, all these liquids are referred to as "dialysate". The respective buffering agent(s) and pH are indicated.

As a reference (internal standard), the buffering capacity of blood plasma ("plasma") was determined. For that purpose, pig blood was tested as follows. First, the bicarbonate concentration and pH were determined, and it was found that the mean bicarbonate concentration was 24.2 mmol/l and the pH was 7.45. Second, said blood was subjected to centrifugation in order to obtain a cell free supernatant. The cell free supernatant was designated plasma.

In FIG. 1, this is referred to as "blood plasma".

1B: Determination of Buffering Capacity

The buffering capacity for $H^+$ ions of all liquids described in section 1A (liquids according to Table 1 of section 1A; plasma as described in section 1A) was experimentally tested. To that end, all liquids (reference exemplary liquids and exemplary liquids according to the present invention, and blood plasma) were subjected to titration with HCl. In particular, 0.1 M HCl was added, the pH was continuously monitored, the solutions were agitated to ensure mixing, and titration was terminated when the pH reached a final value of pH of 6.5. In other words, titration was stopped when the pH reached a value of 6.5. Based on the amount of HCl added until pH 6.5 was reached, the buffering capacity ($H^+$ ion in mmol/l) was calculated.

The buffering capacity determined by this assay is shown in FIG. 1.

The buffering capacity of blood plasma was determined to be 12.00 mmol/l $H^+$ ions.

It is preferred that exemplary liquids according to the present invention (provided in Table 1 as No. 3 to 8)) are characterized by a buffering capacity (in mmol/l) superior to the buffering capacity of blood plasma, as determined by this assay.

Thus, the dialysis liquid according to the present invention provides excellent buffering capacity, particularly in embodiments wherein the inventive dialysis liquid has a pH above the pH of normal human blood.

Example 2: Calcium Concentrations

Dialysis liquid comprising calcium ($Ca^{2+}$ ions) was used, and the pH of the dialysis liquid was altered from pH 7.45 to pH 9 (see FIG. 3). The dialysis liquid was in contact with blood via a semipermeable membrane. The calcium concentration in blood was determined. As can be taken from FIG. 3, even for a calcium concentration above 1.70 mmol/l in the dialysis liquid, the calcium ion concentration in the blood remains within the desired range of 1.00-1.70 mmol/l. This demonstrates that the calcium ion concentration in the dialysis liquid according to the present invention is suitably in a range above 1.70 mmol/l.

Example 3: Oxygenation of Blood

Five liters of heparinized pig blood were continuously pumped through a model extracorporeal blood circuit (Hepa Wash LK2001 dialysis device) at a blood flow rate of 200 ml/min. Schematically, the blood passed through the first chamber (represented by no. 1 in FIG. 2A). The blood was in contact to a dialysis liquid over a semipermeable membrane.

The blood was recycled. However, in order to mimic deoxygenated blood from a patient in need of lung support, and in order to keep the oxygen saturation of hemoglobin of the blood entering the first chamber constant, the blood was continuously deoxygenated. This ensured that the blood entering the first chamber had an oxygen saturation ($O_2Hb$ pre) of about 60 to 70% (see FIG. 4).

The dialysis liquid had a pH of 7.45. The dialysis liquid flow rate was set at 1000 ml/min. Schematically, the dialysis liquid passed through the second chamber (represented by no. 2 in FIG. 2A). The dialysis liquid entering the second chamber was composed as follows:

| | | |
|---|---|---|
| $Na^+$ | 138.00 | mmol/l |
| $K^+$ | 4.00 | mmol/l |
| $Ca^{2+}$ | 2.50 | mmol/l |
| $Mg^{2+}$ | 0.50 | mmol/l |
| $Cl^-$ | 110.00 | mmol/l |
| $HCO_3^-$ | 20.00 | mmol/l |
| Glucose | 1.00 | g/l |
| Albumin | 20.00 | g/l |

For oxygenation, oxygen-enriched osmosis water was constantly initiated into the dialysis liquid before the dialysis liquid entered the second chamber (at a position schematically represented by no. 12 in FIG. 2A). The oxygen concentration and the initiation rate were adjusted to achieve target oxyhemoglobin saturation of about 99%. Oxygen enrichment of the osmosis water can be achieved by any one of the methods described herein. In a particular case, the oxygen enrichment of the osmosis water was achieved by exposure to oxygen at increased pressure, followed by releasing the so-enriched osmosis water through capillaries into the dialysis liquid at a position schematically represented by no. 12 in FIG. 2A.

FIG. 4 shows the success of this experiment:

Oxygen saturation of hemoglobin (in %) was measured (indicated as $O_2Hb$ [%] in FIG. 4).

$O_2Hb$ pre: oxygen saturation of hemoglobin, measured before entry of the blood into the first chamber.

$O_2Hb$ post: oxygen saturation of hemoglobin, measured after exit of the blood from the first chamber.

This example shows that the method of the present invention enables very efficient and continuous oxygenation of blood. As shown in FIG. 4, the oxygen saturation of hemoglobin in blood exiting from the first chamber was constantly above 95%, typically around 99%.

The invention claimed is:

1. Process for oxygenating blood, comprising the steps
   (i) introducing oxygen into blood and/or into a dialysis liquid,
   wherein the dialysis liquid has a pH the range from pH 6.8 to pH 11; and
   wherein the dialysis liquid comprises albumin;
   thereby generating oxygen-enriched blood and/or oxygen-enriching dialysis liquid; and
   (ii) contacting said blood to said dialysis liquid via a semipermeable membrane,
   wherein the oxygen introduced into the blood and/or into the dialysis fluid is introduced by means of liquid oxygen or an oxygen enriched liquid and/or solid, wherein the oxygen-enriched liquid is a homogeneous liquid with molecular oxygen dissolved therein.

2. Process according to claim 1, wherein in step (i) oxygen introduced into the blood is not gaseous oxygen.

3. Process according to claim 1, wherein in step (i) oxygen is introduced into the dialysis liquid and into the blood.

4. Process according to claim 1, wherein in step (i) oxygen is introduced into the dialysis liquid, but not into the blood.

5. Process according to claim 1, wherein said step of exposing encompasses said blood flowing through a first chamber, thereby entering, passing through and exiting the first chamber, and said dialysis liquid flowing through a second chamber, thereby entering, passing through and exiting the second chamber, wherein the first and second chamber are separated from each other by said semipermeable membrane.

6. Process according to claim 5, wherein the first chamber, the semipermeable membrane and the second chamber are comprised by one device, which is a dialysis unit or a dialyzer.

7. Process according to claim 6, wherein step (i) is performed at a site outside the device defined in claim 6, and prior to entering of the blood or the dialysis liquid into said device, so that either the blood or the dialysis liquid, or both enter into the device in oxygen-enriched form.

8. Process according to claim 1, wherein oxygen is introduced into said blood and/or into said dialysis liquid by any one or more of the following:
   (a) infusion of an oxygen-enriched liquid, which is a homogeneous liquid with molecular oxygen dissolved therein;
   (b) infusion of liquid oxygen;
   (c) introducing of oxygen-containing solids, e.g. xerogels and lyogels or frozen oxygen-enriched liquid; and
   (d) convective transport of oxygen-enriched liquid.

9. Process according to claim 1, wherein said dialysis liquid comprises, in addition to albumin, one or more buffering agent(s), which is/are characterized by at least one pKa value in the range from 7.0 to 11.0.

10. Process according to claim 1, wherein said dialysis liquid has a buffering capacity of 12 mmol/l or more for $H^+$ ions.

11. Process according to claim 1, wherein said dialysis liquid is characterized by a pH the range from pH 8.0 to pH 9.0.

12. Process according to claim 1, wherein said dialysis liquid comprises 2,3-diphosphoglycerate (2,3-DPG).

13. Process according to claim 1, wherein at least part of the process is/are carried out at a temperature of less than 37° C.

14. Process according to claim 5, wherein the blood flows through the first chamber at a low-flow flow-rate of 100 to 800 ml/min, at a mid-flow flow-rate of 800 to 2400 ml/min, or at a high-flow flow-rate of more than 2400 ml/min.

15. Process according to claim 1, wherein the pH and the composition of the dialysis liquid are chosen for the amount of oxygen to be added to the blood and/or chosen for the amount of undesired substance to be removed from the blood.

16. Process according to claim 9, wherein the dialysis liquid comprises 10 to 40 mmol/l carbonate/bicarbonate.

17. Process according to claim 9, wherein the dialysis liquid comprises 5 to 20 mmol/l Tris.

18. Process according to claim 5, wherein the dialysis liquid exiting the second chamber, is subjected to at least one treatment step, and subsequently re-enters the second chamber.

19. Process according to claim 18, wherein said at least one treatment step is selected from exposure to an (i) adsorber and/or (ii) contact with a membrane and/or (iii) acidic pH and/or basic pH exposure.

20. Process according to claim 19, wherein said treatment step includes acidification of the dialysis liquid to acidic pH for formation of carbon dioxide and, optionally, removal of carbon dioxide.

21. Process according to claim 1, additionally comprising a step of measuring at least one parameter of the blood and/or of the dialysis liquid, the parameter being selected from one or more of pH, carbon dioxide, partial pressure, bicarbonate ($HCO_3^-$) concentration, buffering capacity, deoxyhemoglobin concentration or saturation (HHb) and oxyhemoglobin saturation ($O_2Hb$).

22. Process according to claim 1, wherein the albumin is selected from human serum albumin and/or bovine serum albumin.

23. Process according to claim 1, wherein the dialysis liquid comprises more than 1.7 mmol/l calcium ($Ca^{2+}$) ions.

24. Process according to claim 18, wherein the pH and/or buffering capacity of the dialysis liquid is adjusted prior to re-introducing the dialysis liquid into the second chamber.

25. Method for extracorporeal treatment of blood from a human or animal subject, wherein the method comprises the steps:
   (i) removing blood from a vein or artery of said subject;
   (ii) subjecting blood of step (i) to a process of claim 1; and
   (iii) reintroducing blood of step (ii) into an artery or vein of said subject.

26. Method according to claim 25, wherein the subject is selected from a subject suffering from lung failure, a subject suffering from respiratory acidosis, a subject suffering from metabolic acidosis, a subject suffering from kidney failure, a subject suffering from a cardiovascular disease, or a subject suffering from combinations of any two or more of these.

27. Process for oxygenating a dialysis liquid comprising a step
   (i) of introducing oxygen into the dialysis liquid,
   wherein the dialysis liquid has a pH in the range from pH 6.8 to pH 11 and wherein the dialysis liquid comprises albumin; thereby generating oxygen-enriched dialysis liquid,
   wherein the oxygen introduced into the dialysis fluid is introduced by means of liquid oxygen or an oxygen enriched liquid and/or solid, and
   wherein the oxygen enriched-liquid is a homogeneous liquid with molecular oxygen dissolved therein.

28. Process according to claim 27, comprising a step (ii) following step (i), wherein in step (ii) the oxygenated dialysis liquid flows through a second chamber, thereby entering, passing through and exiting the second chamber, which second chamber is separated from a first chamber by a semipermeable membrane.

29. Process according to claim 27, wherein the process further comprises the following steps:
- (a) separating a flow of the dialysis liquid into a first flow and a second flow;
- (b) adding an acidic fluid to the first flow of dialysis liquid;
- (c) removing toxins by filtrating, dialysing, precipitating or diafiltrating the acidified first flow of the dialysis liquid;
- (d) adding an alkaline fluid to the second flow of the dialysis liquid;
- (e) removing toxins by filtrating, dialysing, precipitating or diafiltrating the alkalized second flow of the dialysis liquid; and
- (f) merging the first and the second flow of the dialysis liquid.

\* \* \* \* \*